US007786074B2

(12) United States Patent
Gourdie et al.

(10) Patent No.: US 7,786,074 B2
(45) Date of Patent: Aug. 31, 2010

(54) COMPOSITION AND METHODS FOR PROMOTING WOUND HEALING AND TISSUE REGENERATION

(75) Inventors: Robert Gourdie, Charleston, SC (US); Gautam Ghatnekar, Charleston, SC (US); Jane Jourdan, Charleston, SC (US)

(73) Assignee: MUSC Foundation for Research Development Charleston, Charleston, SC (US)

( * ) Notice: Subject to any disclaimer, the term of this patent is extended or adjusted under 35 U.S.C. 154(b) by 314 days.

(21) Appl. No.: 11/721,529

(22) PCT Filed: Dec. 20, 2005

(86) PCT No.: PCT/US2005/046442

§ 371 (c)(1),
(2), (4) Date: Jun. 12, 2007

(87) PCT Pub. No.: WO2006/069181

PCT Pub. Date: Jun. 29, 2006

(65) Prior Publication Data

US 2008/0095819 A1  Apr. 24, 2008

Related U.S. Application Data

(60) Provisional application No. 60/638,366, filed on Dec. 21, 2004, provisional application No. 60/671,796, filed on Apr. 15, 2005.

(51) Int. Cl.
C07K 14/00 (2006.01)
(52) U.S. Cl. .............................. 514/2; 530/300; 530/350
(58) Field of Classification Search .................. None
See application file for complete search history.

(56) References Cited

U.S. PATENT DOCUMENTS

| 6,685,971 | B2 | 2/2004 | Xu et al. |
| 6,991,813 | B2 | 1/2006 | Xu et al. |
| 7,098,190 | B1 | 8/2006 | Becker et al. |
| 2005/0075280 | A1 | 4/2005 | Larsen et al. |

FOREIGN PATENT DOCUMENTS

| WO | WO 00/44409 | 8/2000 |
| WO | WO 00/69896 | 11/2000 |
| WO | WO 02/42422 | 5/2002 |
| WO | WO 02/094981 | 11/2002 |
| WO | WO 03/014303 | 2/2003 |
| WO | WO 03/032964 | 4/2003 |

OTHER PUBLICATIONS

Alonso L, Fuchs E. Stem cells of the skin epithelium. Proc Natl Acad Sci U S A. Sep. 30, 2003;100 Suppl 1:11830-5, 2003.

Angst, B.D., Khan, L.U., Severs, N.J., Whitely, K., Rothery, S., Thompson, R.P., Magee, A.I., and Gourdie, R.G. (1997). Dissociated spatial patterning of gap junctions and cell adhesion junctions during postnatal differentiation of ventricular myocardium. Circulation Research 80, 88-94.

Barker RJ, Gourdie RG. JNK bond regulation: why do mammalian hearts invest in connexin43? Circ Res. Oct. 4, 2002;91(7):556-8.

Barker RJ, Price RL, Gourdie RG. Increased co-localization of connexin43 and ZO-1 in dissociated adult myocytes. Cell Commun Adhes. 2001;8(4-6):205-8.

Barker, R.J., and Gourdie, R.G. (2003). Connexin Interacting Proteins. In: Heart Cell Coupling and Impulse Propagation in Health and Disease. Eds., De Mello W.C. and Janse M.J., Kluwer, Boston, pp. 25-50.

Barker, R.J., Price, R.L., and Gourdie, R.G. (2002). Increased association of ZO-1 with connexin43 during remodeling of cardiac gap junctions. Circ Res 90, 317-324.

Bucci, M. et al. Iin vivo delivery of the caveolin-1 scaffolding domain inhibits nitric oxide synthesis and reduces inflammation. Nat. Med. 6, 1362-1367 (2000).

Bukauskas, F.F., Jordan, K., Bukauskiene, A., Bennett, M.V., Lampe, P.D., Laird, D.W., and Verselis, V.K. (2000). Clustering of connexin 43-enhanced green fluorescent protein gap junction channels and functional coupling in living cells. Proc Natl Acad Sci U S A 97, 2556-2561.

Chen, L., Wright, L.R., Chen, C.H., Oliver, S.F., Wender, P.A., and Mochly-Rosen, D. (2001). Molecular transporters for peptides: delivery of a cardioprotective epsilonPKC agonist peptide into cells and intact ischemic heart using a transport system, R(7). Chem Biol 8, 1123-1129.

Chien KR. Stem cells: lost in translation. Nature. Apr. 8;428(6983):607-608 (2004).

Dang X, Doble BW, Kardami E. The carboxy-tail of connexin-43 localizes to the nucleus and inhibits cell growth. Mol Cell Biochem. Jan. 2003;242(1-2):35-8.

Defamie, N., Mograbi, B., Roger, C., Cronier, L., Malassine, A., Brucker-Davis, F., Fenichel, P., Segretain, D., and Pointis, G. (2001). Disruption of gap junctional intercellular communication by lindane is associated with aberrant localization of connexin43 and zonula occludens-1 in 42GPA9 Sertoli cells. Carcinogenesis 22, 1537-1542.

Derossi, D., Joliot, A. H., Chassaing, G. & Prochiantz, A. The third helix of Antennapedia homeodomain translocates through biological membranes. J Biol Chem. Apr. 8, 1994;269(14):10444-50.

Dev KK. Making protein interactions druggable: targeting PDZ domains. Nat Rev Drug Discov. Dec. 2004;3(12):1047-56.

Duffy, H.S., Ashton, A.W., O'Donnell, P., Coombs, W., Taffet, S.M., Delmar, M., and Spray, D.C. (2004). Regulation of connexin43 protein complexes by intracellular acidification. Circ. Res. 94, 215-222.

Duffy, H.S., Delmar, M., and Spray, D.C. (2002). Formation of the gap junction nexus: binding partners for connexins. J Physiol Paris 96, 243-249.

(Continued)

Primary Examiner—Karen Cochrane Carlson
(74) Attorney, Agent, or Firm—Cooley LLP

(57) ABSTRACT

Provided herein are compositions and methods for use in promoting wound healing and tissue regeneration following tissue injury in a subject.

34 Claims, 8 Drawing Sheets

OTHER PUBLICATIONS

Dupont, E., Matsushita, T., Kaba, R.A., Vozzi, C., Coppen, S.R., Khan, N., Kaprielian, R., Yacoub, M.H., and Severs, N.J. (2001). Altered connexin expression in human congestive heart failure. J. Mol Cell Cardiol 33, 359-371.

Elmquist, A., Lindgren, M., Bartfai, T. & Langel, U. VE-cadherin-derived cell-penetrating peptide, pVEC, with carrier functions. Exp. Cell Res. 269, 237-244 (2001).

Evans, W.H., Martin, P.E. (2002). Gap junctions: structure and function. Mol Membr Biol 19, 121-36.

Fanning, A.S., Ma, T.Y., and Anderson, J.M. (2002). Isolation and functional characterization of the actin binding region in the tight junction protein ZO-1. Faseb J 16, 1835-1837.

Fawcett JW, Asher RA. The glial scar and central nervous system repair. Brain Res. Bull. 49:377-391 (1999).

Fischer, P.M. et al. Structure-activity relationship of truncated and substituted analogues of the intracellular delivery vector Penetratin. J. Pept. Res. 55, 163-172 (2000).

Fishman, G.I., Hertzberg, E.L., Spray, D.C., and Leinwand, L.A. (1991). Expression of connexin43 in the developing rat heart. Circulation Research 68, 782-287.

Fonseca G.C., Green, C.R., and Nicholson L.F. (2002). Upregulation in astrocytic connexin 43 gap junction levels may exacerbate generalized seizures in mesial temporal lobe epilepsy. Brain Research 1, 105-116.

Frankel, A. D. & Pabo, C. O. Cellular uptake of the Tat protein from human immunodeficiency virus. Cell 55,1189-1193 (1988).

Fromaget, C., El Aoumari, A., and Gros, D. (1992). Distribution pattern of connexin 43, a gap junctional protein, during the differentiation of mouse heart myocytes, Differentiation 51, 9-20.

Fromaget, C., el Aoumari, A., Dupont, E., Briand, J.P., Gros, D. (1990). Changes in the expression of connexin 43, a cardiac gap junctional protein, during mouse heart development. J Mol Cell Cardiol. 22, 1245-58.

Fu CT, Bechberger JF, Ozog MA, Perbal B, Naus CC. CCN3 (NOV) interacts with Connexin43 in C6 glioma cells: possible mechanism of Connexin-mediated growth suppression. J Biol Chem. Aug. 27;279(35):36943-50 (2004).

Fujii N, Haresco JJ, Novak KA, Stokoe D, Kuntz ID, Guy RK. A selective irreversible inhibitor targeting a PDZ protein interaction domain. J Am Chem Soc. Oct. 8, 2003;125(40):12074-5.

Gaietta, G., Deernick, T.J., Adams, S.R., Bouwer, J., Tour, O., Laird, D.W., Sosinsky, G.E., Tsien, R.Y., and Ellisman, M.H. (2002). Multicolor and electron microscopic imaging of connexin trafficking. Science 296, 503-507.

Gao, C. et al. A cell-penetrating peptide from a novel pVII-pIX phage-displayed random peptide library. Bioorg. Med. Chem. 10, 4057-4065 (2002).

Giepmans BN, Moolenaar WH. The gap junction protein connexin43 interacts with the second PDZ domain of the zona occludens-1 protein. rr Biol. Jul. 30-Aug. 13, 1998;8(16):931-4.

Giepmans BN. Gap junctions and Connexin-interacting proteins. Cardiovasc Res. May 1;62(2):233-45 (2004).

Giepmans, B.N., Verlaan, I., Hengeveld, T., Janssen, H., Calafat, J., Falk, M.M., and Moolenaar, W.H. (2001). Gap junction protein connexin-43 interacts directly with microtubules. Curr Biol 11, 1364-1368.

Gil-Parrado, S., Assfalg-Machleidt, I., Fiorino, F., Deluca, D., Pfeiler, D., Schaschke, N., Moroder, L., and Machleidt, W. (2003). Calpastatin exon 1 B-derived peptide, a selective inhibitor of calpain: enhancing cell permeability by conjugation with penetratin. Biol Chem 384, 395-402.

Gonzalez-Mariscal, L., Betanzos, A., Nava, P., and Jaramillo, B.E. (2003). Tight junction proteins. Prog Biophys Mol Biol 81, 1-44.

Goodenough, D.A., and Paul, D.L. (2003). Beyond the gap: functions of unpaired connexon channels. Nat Rev Mol Cell Biol 4, 285-294.

Gourdie RG, Ghatnekar GS, O'Quinn M, Rhett MJ, Barker RJ, Zhu C, Jourdan J, Hunter AW. The unstoppable connexin43 carboxyl-terminus: new roles in gap junction organization and wound healing. Ann N Y Acad Sci. Oct. 2006;1080:49-62.

Gourdie, R.G., Green, C.R., and Severs, N.J. (1991). Gap junction distribution in adult mammalian myocardium revealed by an anti-peptide antibody and laser scanning confocal microscopy. Journal of Cell Science 99, 41-55.

Gourdie et al. NIH Grant 5R01HL056728, 2001.

Green, C.R., Peters, N.S., Gourdie, R.G., Rothery, S., and Severs, N.J. (1993). Validation of immunohistochemical quantification in confocal scanning laser microscopy: A comparative assessment of gap junction size with confocal and ultrastructural techniques. Journal of Histochemistry and Cytochemistry 41, 1339-1349.

Green, M. & Loewenstein, P. M. Autonomous functional domains of chemically synthesized human immunodeficiency virus tat trans-activator protein. Cell 55, 1179-1188 (1988).

Gros, D., Mocquard, J.P., Challice, C.E., and Schrevel, J. (1978). Formation and growth of gap junctions in mouse myocardium during ontogenesis: a freeze-cleave study, J Cell Sci 30, 45-61.

Gros, D.B., and Jongsma, H.J. (1996). Connexins in mammalian heart function. BioEssays 18, 719-730.

Hall, J.E., and Gourdie, R.G. (1995). Spatial organization of cardiac gap junctions can affect access resistance. Microsc Res Tech 31, 446-451.

Harris, A.L. (2001). Emerging issues of connexin channels: biophysics fills the gap. Q Rev Biophys 34, 325-472.

Hayashi T, Matesic DF, Nomata K, Kang KS, Chang CC, Trosko JE. Stimulation of cell proliferation and inhibition of gap junctional intercellular communication by linoleic acid. Cancer Lett. 112:103-111 (1997).

Hayashi T, Nomata K, Chang CC, Ruch RJ, Trosko JE. Cooperative effects of v-myc and c-Ha-ras oncogenes on gap junctional intercellular communication and tumorigenicity in rat liver epithelial cells. Cancer Lett. 128:145-154 (1998).

Hayashi T, Trosko JE, Hamada K. Inhibition of gap junctional intercellular communication in rat liver epithelial cells with trans-forming RNA. FEBS Lett. 491:200-206 (2001).

Hong, F. D. & Clayman, G. L. Isolation of a peptide for targeted drug delivery into human head and neck solid tumors. Cancer Res. 60, 6551-6556 (2000).

Hunter AW, Barker RJ, Zhu C, Gourdie RG. Zonula occludens-1 alters connexin43 gap junction size and organization by influencing channel accretion. Mol Biol Cell. Dec. 2005;16(12):5686-98. Epub Sep. 29, 2005.

Hunter AW, Jourdan J, Gourdie RG. Fusion of GFP to the carboxyl terminus of connexin43 increases gap junction size in HeLa cells. Cell Commun Adhes. Jul.-Dec. 2003;10(4-6):211-4.

Itoh, M., Nagafuchi, A., Moroi, S., and Tsukita, S. (1997). Involvement of ZO-1 in cadherin-based cell adhesion through its direct binding to alpha catenin and actin filaments. J Cell Biol 138, 181-192.

Jin, C., and Lau, A.F. (2000). Identification of connexin-interacting proteins: application of the yeast two-hybrid screen. Methods 20, 219-231.

Johnson, R.G., Meyer, R.A.. Li, X.R., Preus, D.M., Tan, I., Grunenwald, H., Paulson, A.F., Laird, D.W., Sheridan, J.D. (2002). Gap junctions assemble in the presence of cytoskeletal inhibitors, but enhanced assembly requires microtubules. Experimental Cell Research 275, 67-80.

Jordan, K., Solan, J.L., Dominguez, M., Sia, M., Hand, A., Lampe, P.D., and Laird, D.W. (1999). Trafficking, assembly, and function of a connexin43-green fluorescent protein chimera in live mammalian cells. Mol Biol Cell 10, 2033-2050.

Kajstura J, Rota M, Whang B, Cascapera S, Hosoda T, Bearzi C, Nurzynska D, Kasahara H, Zias E, Bonafe M, Nadal-Ginard B, Torella D, Nascimbene A, Quaini F, Urbanek K, Leri A, Anversa P. Bone marrow cells differentiate in cardiac cell lineages after infarction independently of cell fusion. Circ Res. Jan. 7;96(1):127-37 (2005).

Kanovsky, M., Raffo, A., Drew, L., Rosal, R., Do, T., Friedman, F.K., Rubinstein, P., Visser, J., Robinson, R., Brandt-Rauf, P.W., Michl, J., Fine, R.L., and Pincus, M.R. (2001). Peptides from the amino terminal mdm-2-binding domain of p53, designed from conformational analysis, are selectively cytotoxic to transformed cells. Proc Natl Acad Sci U S A 98, 12438-12443.

Kaprielian, R.R., Gunning, M., Dupont, E., Sheppard, M.N., Rothery, S.M., Underwood, R., Pennell, D.J., Fox, K., Pepper, J., Poole-Wilson, P.A., and Severs, N.J. (1998). Downregulation of immunodetectable connexin43 and decreased gap junction size in the pathogenesis of chronic hibernation in the human left ventricle. Circulation 97, 651-660.

Kausalya PJ, Phua DC, Hunziker W. Association of ARVCF with zonula occludens (ZO)-1 and ZO-2: binding to PDZ-domain proteins and cell-cell adhesion regulate plasma membrane and nuclear localization of ARVCF. Mol Biol Cell. Dec. 2004;15(12):5503-15. Epub Sep. 29, 2004.

Kausalya, P.J., Reichert, M., and Hunziker, W. (2001). Connexin45 directly binds to ZO-1 and localizes to the tight junction region in epithelial MDCK cells 505, 92-96.

Kumar, N.M., and Gilula, N.B. (1996). The gap junction communication channel. Cell 84, 381-388.

Kwak BR, Pepper MS, Gros DB, Meda P. Inhibition of endothelial wound repair by dominant negative connexin inhibitors. Mol Biol Cell. Apr. 2001;12(4):831-45.

Laing, J.G., Manley-Markowski, R.N., Koval, M., Civitelli, R., Steinberg, T.H. (2001). Connexin45 interacts with zonula occludens-1 and connexin43 in osteoblastic cells. J Biol Chem 276, 23051-5.

Laird, D.W., Jordan, K., and Shao, Q. (2001). Expression and imaging of connexin-GFP chimeras in live mammalian cells. Methods Mol Biol 154, 135-142.

Lampe, P.D., and Lau, A.F. (2000). Regulation of gap junctions by phosphorylation of connexins. Arch Biochem Biophys 384, 205-215.

Lauf, U., Giepmans, B.N., Lopez, P., Braconnot, S., Chen, S.C., and Falk, M.M. (2002). Dynamic trafficking and delivery of connexons to the plasma membrane and accretion to gap junctions in living cells. Proc Natl Acad Sci U S A 99, 10446-10451.

Lauf, U., Lopez, P., and Falk, M.M. (2001). Expression of fluorescently tagged connexins: a novel approach to rescue function of oligomeric DsRed-tagged proteins. FEBS Lett 498, 11-15.

Legato, M.J. (1979). Cellular Mechanisms of Normal Growth in the Mammalian Heart I. Qualitative and Quantitative Features of Ventricular Architecture in the Dog from Birth to Five Months of Age. Circulation Research 44, 250-262.

Li, X., Olson, C., Lu, S., Kamasawa, N., Yasumura, T., Rash, J.E., Nagy, J.I. Neuronal connexin36 association with zonula occludens-1 protein (ZO-1) in mouse brain and interaction with the first PDZ domain of ZO-1. (2004). Eur J Neurosci. 19, 2132-46.

Lin, Y. Z., Yao, S. Y., Veach, R. A., Torgerson, T. R. & Hawiger, J. Inhibition of nuclear translocation of transcription factor NF-κB by a synthetic peptide containing a cell membrane-permeable motif and nuclear localization sequence. J. Biol. Chem. 270, 14255-14258 (1995).

Liu, S., Taffet, S., Stoner, L., Delmar, M., Vallano, M.L., and Jalife, J. (1993). A structural basis for the unequal sensitivity of the major cardiac and liver gap junctions to intracellular acidification: the carboxyl tail length. Biophys J 64, 1422-1433.

Lo C.W. (2000). Role of gap junctions in cardiac conduction and development: insights from the connexin knockout mice. Circulation Research 87, 346-8.

Lundberg, P. et al. Cell membrane translocation of the N-terminal (1-28) part of the prion protein. Biochem. Biophys. Res. Commun. 299, 85-90 (2002).

Martin P. Wound healing—aiming for perfect skin regeneration. Science. Apr. 4, 1997;276(5309):75-81.

Matsushita M, Noguchi H, Lu YF, Tomizawa K, Michiue H, Li ST, Hirose K, Bonner-Weir S, Matsui H. Photo-acceleration of protein release from endosome in the protein transduction system. FEBS Lett. 13;572(1-3):221-6. (2004).

Merrifield, C.J., Moss, S.E., Ballestrem, C., Imhof, B.A., Giese, G., Wunderlich, I., and Almers, W. (1999). Endocytic vesicles move at the tips of actin tails in cultured mast cells. Nat Cell Biol 1, 72-74.

Chu MY, Lipsky MH, Yee LK, Epstein J, Whartenby KA, Freeman S, Chen TM, Chu E, Forman EN, Calabresi P. Predictive Sensitivity of Human Cancer Cells iin vivo Using Semipermeable Polysulfone Fibers. Pharmacology. Jun. 1998;56(6):318-26.

Mitic, L.L., and Anderson, J.M. (1998). Molecular architecture of tight junctions. Annu Rev Physiol 60, 121-142.

Moorby CD. A connexin 43 mutant lacking the carboxyl cytoplasmic domain inhibits both growth and motility of mouse 3T3 fibroblasts. Mol Carcinog. May 2000;28(1):23-30.

Morris, M. C., Depollier, J., Mery, J., Heitz, F. & Divita, G. A peptide carrier for the delivery of biologically active proteins into mammalian cells. Nature Biotechnol. 19, 1173-1176 (2001).

Murray, S.A., Williams, S.Y., Dillard, C.Y., Narayanan, S.K., and McCauley, J. (1997). Relationship of cytoskeletal filaments to annular gap junction expression in human adrenal cortical tumor cells in culture. Exp Cell Res 234, 398-404.

Musil, L.S., and Goodenough, D.A. (1991). Biochemical analysis of connexin43 intracellular transport, phosphorylation, and assembly into gap junctional plaques. J Cell Biol 115, 1357-1374.

Nielsen PA, Baruch A, Shestopalov VI, Giepmans BN, Dunia I, Benedetti EL, Kumar NM. Lens connexins alpha3Cx46 and alpha8Cx50 interact with zonula occludens protein-1 (ZO-1). Mol Biol Cell. Jun. 2003;14(6):2470-81. Epub Mar. 7, 2003.

Norenberg MD. Astrocyte responses to CNS injury. J. Neuropathol. Exp. Neurol. 53:213-220 (1994).

Oehlke, J. et al. Cellular uptake of an α-helical amphipathic model peptide with the potential to deliver polar compounds into the cell interior non-endocytically. Biochim. Biophys. Acta. 1414, 127-139 (1998).

Orlandini GC, Margaria R. Evaluation of the efficiency of a new hollow fiber plasmapheresis filter. Int J Artif Organs. Jul. 1983;6 Suppl 1:103-6.

Park, C. B., Yi, K. S., Matsuzaki, K., Kim, M. S. & Kim, S. C. Structure-activity analysis of buforin II, a histone H2A-derived antimicrobial peptide: the proline hinge is responsible for the cell-penetrating ability of buforin II. Proc. Natl Acad. Sci. USA 97, 8245-8250 (2000).

Pich A, Chiusa L, Navone R. Prognostic relevance of cell proliferation in head and neck tumors Annals of Oncology 2004 15(9):1319-1329.

Pooga, M., Hallbrink, M., Zorko, M. & Langel, U. Cell penetration by transportan. FASEB J. 12, 67-77 (1998).

Poss KD, Wilson LG, Keating MT. Heart regeneration in zebrafish. Science. Dec. 13;298(5601):2188-90 (2002).

Prochiantz, A. (1999). Homeodomain-derived peptides. In and out of the cells. Ann N Y Acad Sci 886, 172-179.

Qiu C, Coutinho P, Frank S, Franke S, Law LY, Martin P, Green CR, Becker DL. Targeting connexin43 expression accelerates the rate of wound repair. Curr Biol. Sep. 30, 2003;13(19):1697-703.

Rousselle, C. et al. New advances in the transport of doxorubicin through the blood-brain barrier by a peptide vector-mediated strategy. Mol. Pharmacol. 57(4):679-86 (2000).

Saitongdee, P., Milner, P., Becker, D.L., Knight, G.E., and Burnstock, G. (2000). Increased connexin43 gap junction protein in hamster cardiomyocytes during cold acclimatization and hibernation. Cardiovasc Res 47, 108-115.

Sawada, M., Hayes, P. & Matsuyama, S. Cytoprotective membrane-permeable peptides designed from the Bax-binding domain of Ku70. Nature Cell Biol. 5, 352-357 (2003).

Segretain, D., and Falk, M.M. (2004). Regulation of connexin biosynthesis, assembly, gap junction formation, and removal. Bioch. Bioph. Acta 1662, 3-21.

Segretain, D., Fiorini, C., Decrouy, X., Defamie, N., Prat, J.R., Pointis, G. (2004). A proposed role for ZO-1 in targeting connexin 43 gap junctions to the endocytic pathway. Biochimie. 86, 241-4.

Sepp, R., Severs, N.J., and Gourdie, R.G. (1996). Altered patterns of cardiac intercellular junction distribution in hypertrophic cardiomyopathy. Heart 76, 412-417.

Severs, N.J., Dupont, E., Coppen, S.R., Halliday, D., Inett, E., Baylis, D., Rothery, S. (2004). Remodelling of gap junctions and connexin expression in heart disease. Biochim Biophys Acta. 1662, 138-48.

Shibata, Y., Nakata, K., and Page, E. (1980). Ultrastructual changes during development of gap junctions in rabbit left ventricular myocardial cells. Journal of Ultrastructure Research 71, 258-271.

Silver J, Miller JH. Regeneration beyond the glial scar. Nat Rev Neurosci. Feb.;5(2):146-56 (2004).

Simpson, D.G., Terracio, L., Terracio, M., Price, R.L., Turner, D.C., and Borg, T.K. (1994). Modulation of cardiac myocyte phenotype in vitro by the composition and orientation of the extracellular matrix. Journal of Cellular Physiology 161, 89-105.

Smith, J.H., Green, C.R., Peters, N.S., Rothery, S., and Severs, N.J. (1991). Altered patterns of gap junction distribution in ischemic heart disease. An immunohistochemical study of human myocardium using laser scanning confocal microscopy. American Journal of Pathology 139, 801-821.

Songyang, Z. et al. Recognition of unique carboxyl-terminal motifs by distinct PDZ domains. Science 275, 73-77 (1997).

Spach, M.S. (2003). Transition from a continuous to discontinuous understanding of cardiac conduction Circ Res. Feb. 7, 2003;92(2):125-6.

Spach, M.S., Heidlage, J.F., Dolber, P.C., Barr, R.C. (2000). Electrophysiological effects of remodeling cardiac gap junctions and cell size: experimental and model studies of normal cardiac growth. Circulation Research 86, 302-11.

Stevenson, B.R., Siliciano, J.D., Mooseker, M.S., and Goodenough, D.A. (1986). Identification of ZO-1: a high molecular weight polypeptide associated with the tight junction (zonula occludens) in a variety of epithelia. J Cell Biol 103, 755-766.

Sullivan R, Lo CW. Expression of a connexin 43/beta-galactosidase fusion protein inhibits gap junctional communication in NIH3T3 cells. J Cell Biol. Jul. 1995;130(2):419-29.

Thomas, T., Jordan, K., and Laird, D.W. (2001). Role of cytoskeletal elements in the recruitment of Cx43-GFP and Cx26-YFP into gap junctions. Cell Commun Adhes 8, 231-236.

Toyofuku T, Akamatsu Y, Zhang H, Kuzuya T, Tada M, Hori M. c-Src regulates the interaction between connexin-43 and ZO-1 in cardiac myocytes. J Biol Chem. Jan. 19, 2001;276(3):1780-8. Epub Oct. 16, 2000.

Toyofuku T, Yabuki M, Otsu K, Kuzuya T, Hori M, Tada M. Direct association of the gap junction protein connexin-43 with ZO-1 in cardiac myocytes. J Biol Chem. May 22, 1998;273(21):12725-31.

Tsao MS, Smith JD, Nelson KG, Grisham JW. A diploid epithelial cell line from normal adult rat liver with phenotypic properties of 'oval' cells. Exp. Cell Res. 154:38-52 (1984).

Vigneron, J.P. et al. Guanidinium-cholesterol cationic lipids: Efficient vectors for the transfection of eukaryotic cells. Proc. Natl. Acad. Sci. USA. 93, 9682-9686 (1998).

Wadia JS, Stan RV, Dowdy SF. Transducible TAT-HA fusogenic peptide enhances escape of TAT-fusion proteins after lipid raft macropinocytosis. Nat Med. 10(3):310-5. (2004).

Wilgus TA, Vodovotz Y, Vittadini E, Clubbs EA, Oberysztn TM. Reduction of scar formation in full-thickness wounds with topical celecoxib treatment. Wound Rep Reg 2003; 11:25-34.

Yoo DS. The dielectric properties of cancerous tissues in a nude mouse xenograft model. Bioelectromagnetics. Oct. 2004;25(7):492-7.

Zhu C., Barker, R.J., Hunter, A.W., Zhang, Y., Jourdan, J., and Gourdie, R.G. (2004). Quantitative Analysis of ZO-1 Co-Localization with Cx43 Gap Junction Plaques in Cultures of Rat Neonatal Cardiomyocytes. Microsc Microanal. Jun. 2005;11(3):244-8.

Scale bars (a,b,c,d) = 10 microns
Scale bars (e,f) = 62.5 microns

Green = GFAP astrocyte marker, red = nuclei
Scale bars = 10 microns

US 7,786,074 B2

COMPOSITION AND METHODS FOR PROMOTING WOUND HEALING AND TISSUE REGENERATION

CROSS-REFERENCE TO RELATED APPLICATIONS

This application claims benefit of U.S. Provisional Application No. 60/638,366, filed Dec. 21, 2004 and U.S. Provisional Application No. 60/671,796, filed Apr. 15, 2005, which are hereby incorporated herein by reference in their entirety.

ACKNOWLEDGEMENTS

This invention was made with government support under Grant RO-1 HL56728 awarded by the National Institutes of Health. The government has certain rights in the invention.

BACKGROUND OF THE INVENTION

Your average kid knows that if a skink lizard looses a tail it will eventually grow another one. Moreover, it is well understood among children and grown-ups who make a habit of studying such things that many lower animals are capable of regenerating quite complex structures, including whole limbs and organs following injury. For example, fish are able to grow back a heart after a significant part of the old heart of the fish had been sliced away (Poss et al., 2002). This is an astounding result when one reflects on how essential the heart is to the minute-to-minute survival of most animals.

However, regeneration of tissue, limbs and organs following injury in people is not as straightforward as it is in fish. While human tissues damaged by mechanical wounding, disease processes and other causes are capable of healing, complex tissue structure and function is rarely, if ever wholly restored. Instead, recovery of nearly all tissues from injury in humans and other higher vertebrates is dominated by the formation of scar tissue. The most familiar example of this is the discolored and fibrotic scars that linger following the healing of a skin cut or graze. Less well appreciated is that formation of glial scar tissue following injury to the brain or spinal chord is one of the main obstacles to restoration of neural function following damage to the central nervous system (Silver and Miller J H, 2004). There is currently no means of treating or preventing such scarring and promoting the regeneration of complex tissue structure and function following injury.

BRIEF SUMMARY OF THE INVENTION

Provided is an isolated polypeptide comprising a carboxy-terminal amino acid sequence of an alpha Connexin (also referred to herein as an alpha Connexin carboxy-Terminal (ACT) polypeptide), or a conservative variant thereof.

Provided herein is a method of promoting wound healing following tissue injury in a subject, comprising administering to the subject one or more of the herein provided compositions (e.g., polypeptides, nucleic acids, or vectors) in a pharmaceutically acceptable carrier.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

Figure 4:
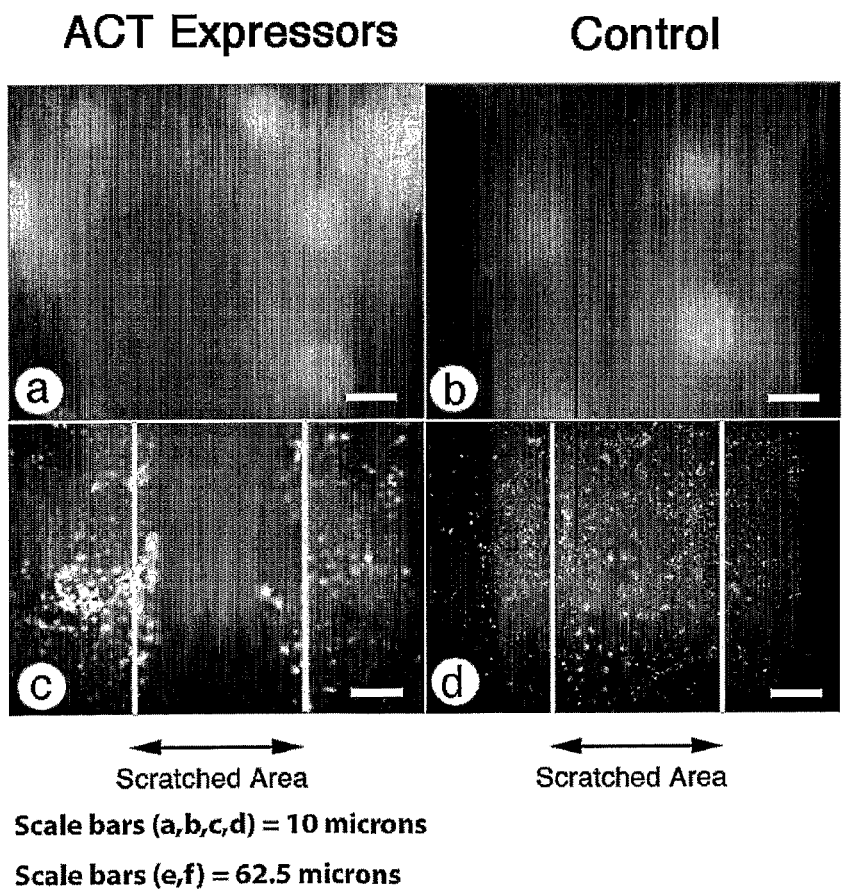

FIG. 4 shows that expression of an ACT-peptide-encoding-polynucleotide operably linked to a promoter in the epithelial cell WB-F344 inhibits migration following scratch injury in an experimental cellular model. WB-F344 cells are a transformed rat epithelial cell line derived by treatment of isolated rat liver cells with a cancer-causing agent (Tsao et al., 1984; Hayashi et al., 1997; Hayashi et al., 1998; Hayashi et al., 2001). WB-F344 cells were transfected with a cDNA expression plasmid construct and selected under antibiotic using standard protocols to generate cell lines that stably expressed an ACT-peptide-encoding-polynucleotide (SEQ ID NO:6) operably linked to a promoter sequence or a green fluorescent protein (GFP) polynucleotide operably linked to a promoter sequence as a control. The polynucleotide encoding the ACT peptide also encoded GFP. As such, expression of the ACT peptide could be assayed by standard GFP fluorescence optics on a light microscope. (a) and (b) show high magnification images of GFP fluorescence in WB-F344 cell lines expressing GFP plus the carboxy terminus ACT peptide sequence (a) or GFP alone (b). Near confluent monolayers of the WB-F344 cell lines were "scratch injured" and allowed to "heal" for 24 hours. Similar to the control cases of the NIH-3T3 cells treated with vehicle or non-active control peptide, the control epithelial cell line expressing GFP repopulated the scratch injury (d). However, in the epithelial cell line that stably expressed the ACT-peptide-encoding-polynucleotide operably linked to a promoter sequence, there was inhibited repopulation of the scratch injury (c).

Figure 5:
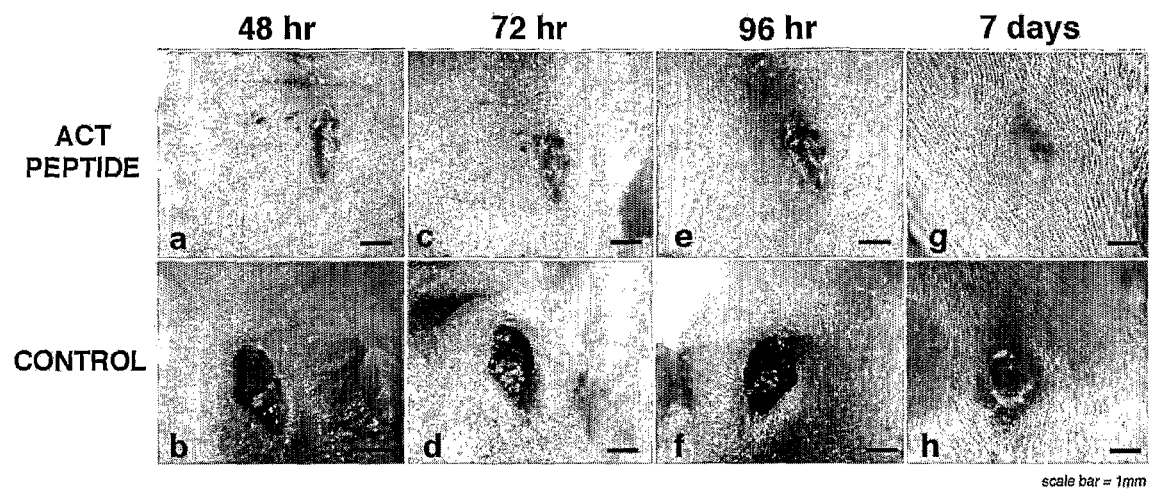

FIG. 5 shows that ACT peptide reduces inflammation, improves healing and reduces scarring following incisional skin injury in a neonatal mouse. Neonatal mouse pups were desensitized using hypothermia. A 4 mm long incisional skin injury was made using a scalpel through the entire thickness of the skin (down to the level of the underlying muscle) in the dorsal mid line between the shoulder blades. 30 µl of a solution of 20% pluronic (F-127) gel containing either no (control) or dissolved ACT 1 peptide (SEQ ID NO: 2) at a concentration of 60 µM was then applied to the incisional injuries. Control or ACT peptide containing gel was applied subsequently 24 hours after the initial application. No further application of control and ACT peptide containing gel was made after the second application. By 48 hours the ACT peptide treated injury (a) is significantly more closed, less inflamed, less swollen (note ridges at the wound edge), and generally more healed in appearance than the control injury that received no ACT peptide (b). These differences in inflammation, swelling and healing between the control and ACT peptide and control treated injury persisted at the 72 (c, d) and 96 (e, f) hour time points. At 7 days, the ACT peptide wound (g), had a smoother and less scarred appearance than the control peptide-treated injury (h). Note that images of the same injury on the same animal are shown at the different time points during the healing time course.

Figure 6:
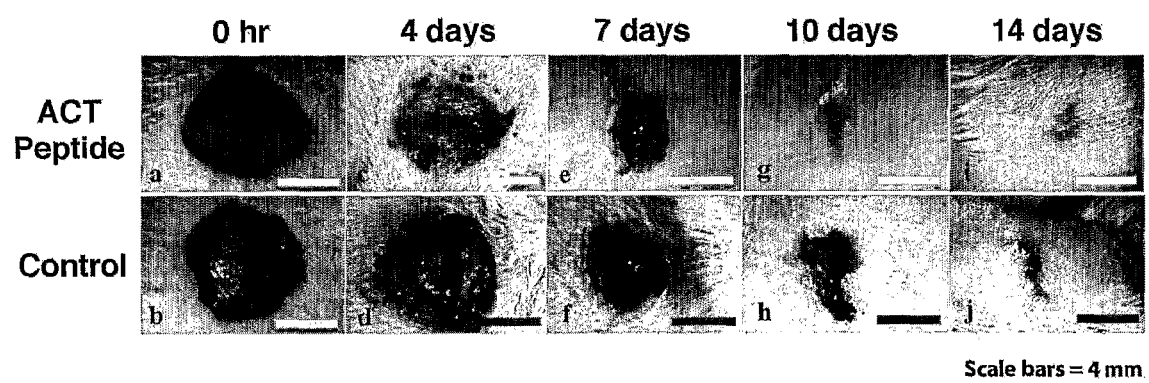

FIG. 6 shows that ACT peptide reduces inflammation, improves healing and reduces scarring following a large excisional skin injury in adult mice. Anesthetized adult mice had 8 mm wide circular excisional skin injuries made by fine surgical scissors down to the underlying muscle in the dorsal mid line between the shoulder blades (i.e., as shown in (a) an (b). The boundary of the injury was demarcated by an 8 mm wide circular template cut in a plastic sheet. 100 µl of a solution of 30% pluronic gel containing either no (control) or dissolved ACT 1 peptide (SEQ ID NO:2) at a concentration of 100 µM was then applied to the excisional injuries. Control or ACT peptide containing gel was applied subsequently 24 hours after the initial application. No further applications of control and ACT peptide containing gel were made after the second application. The ACT peptide-treated large excisional injury (a, c e, g, i) closed faster, was less inflamed in appearance, healed faster and scarred less than the control injury that received no ACT peptide (b, d, f, h, j) over the 14 day time course. Indeed, the control injury at 14 days still shows a partial scab indicating that acute healing of the injury was incomplete (j). Note that images of the same injury on the same animal are shown at the different time points during the healing time course.

Figure 7:
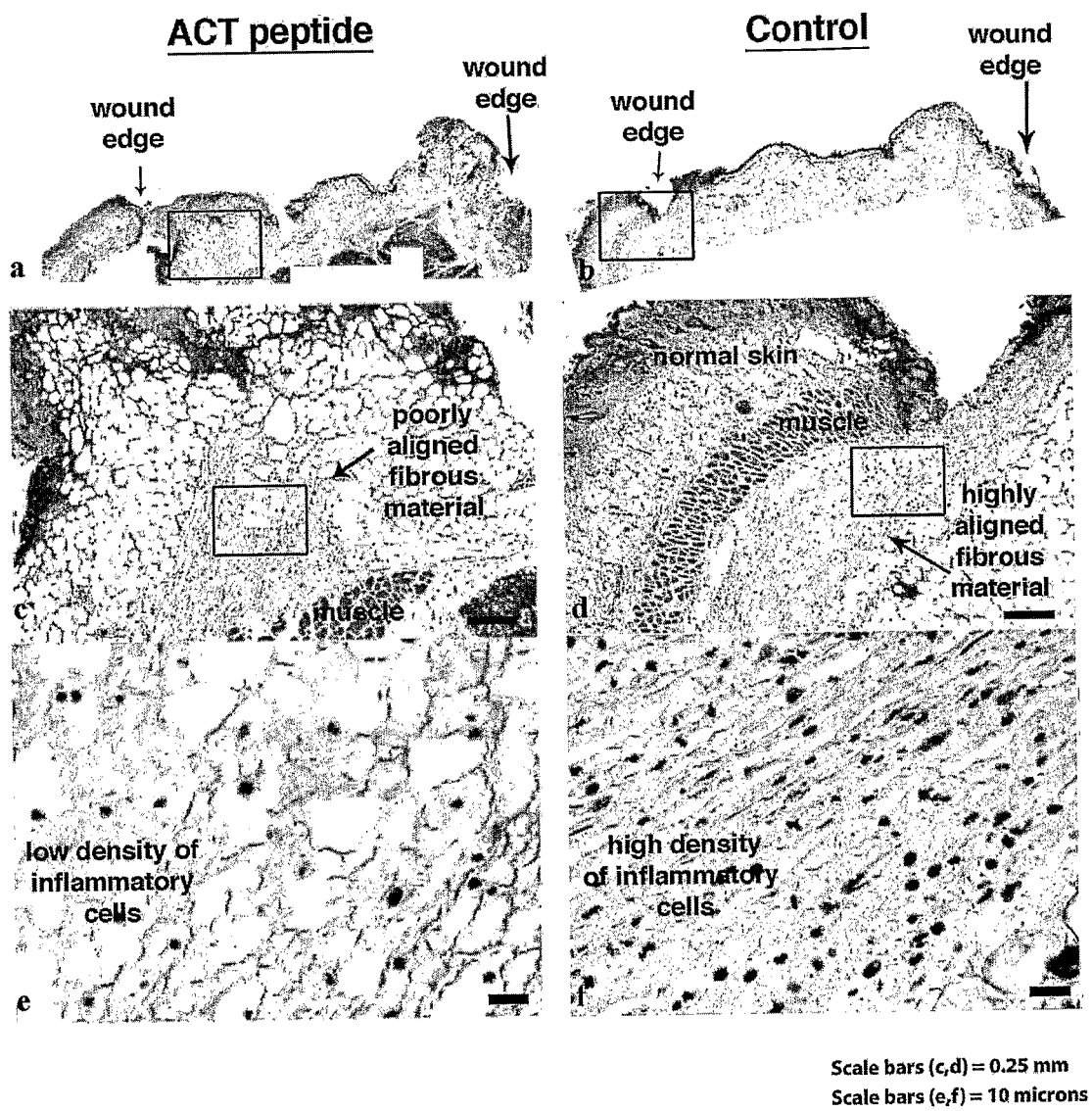

FIG. 7 shows that ACT peptide reduces the density of inflammatory cells following excisional skin injury in adult mice. Skin biopsies of the entire wound site were taken from some of the mice 24 hours following the excisional injury in the experiment described in FIG. 6. Figures (a) and (b) show low magnification survey views of cross-sections from near the center of the wound of control and ACT peptide treated injuries respectively. The wound edge (marked by the small arrows), bounded by skin of normal histological appearance, can be seen in both cases. A black rectangle is placed over the images in (a) and (b) at the left hand wound edge. The histological structures within these two rectangles are shown at higher magnification in (c) and (d) for control and ACT peptide treated tissues, respectively. Of most interest is a "collar-like" tissue of aligned fibrous material (arrowed) projecting from basal parts of the injury to or toward the wound edge and exterior surface of injury. The aligned fibrous substrate has the appearance of being much more organized in the control injury (d) than in the ACT peptide treated injury (c). Also, there is a considerably lower density of inflammatory cells studding the fibrous substrate in the ACT peptide-treated tissue. This is confirmed in (e) and (f) where regions of histological section within the black rectangles shown in (c) and (d) are respectively shown at higher magnification. The inflammatory cells studding the aligned fibrous substrate include mast cells, neutrophils and macrophages. These inflammatory cells occur at much higher density in the control injury than in the ACT peptide treated injury.

Figure 8:
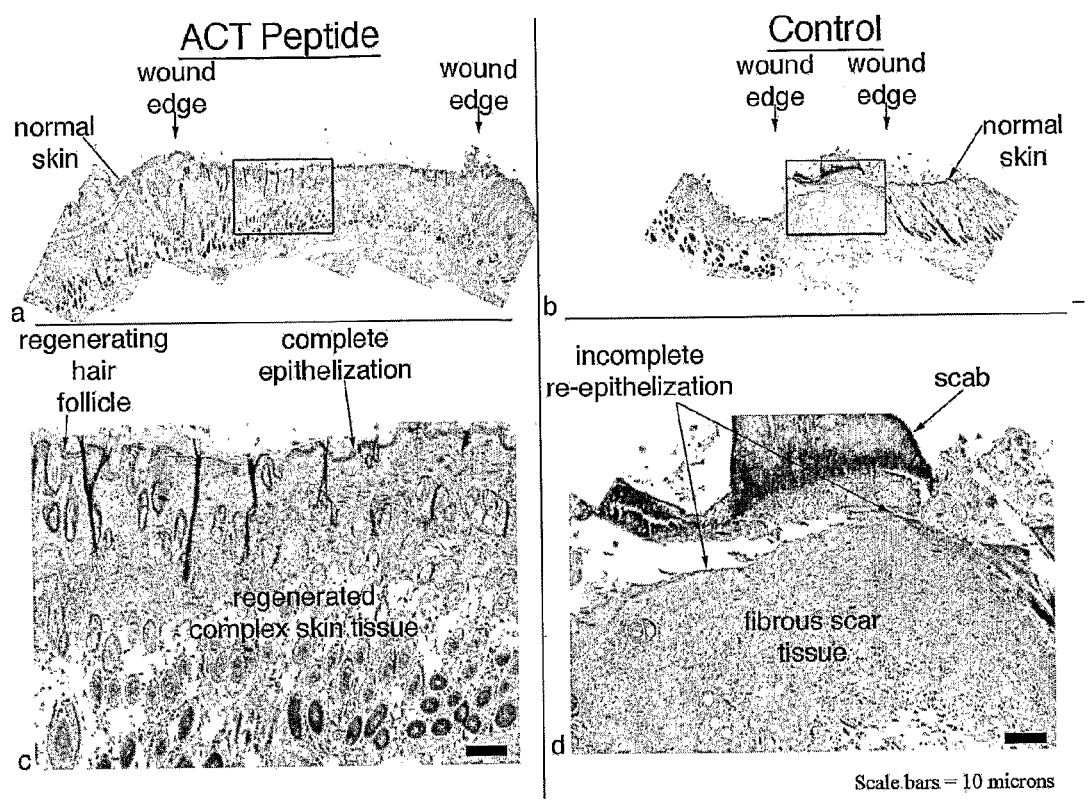
Figure 9:
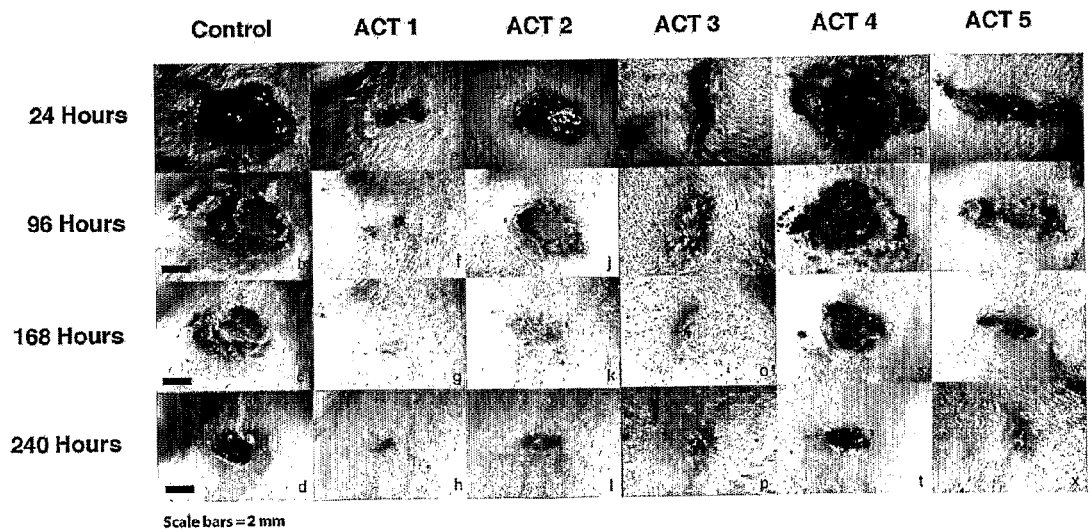

FIG. 8 shows that ACT peptide promotes healing, reduces scarring and promotes regeneration of complex tissue structure following excisional skin injury in adult mice. At the end of the 14 day period in the experiment described in FIG. 6, skin biopsies of the entire excisional injury were taken and histological sections from these skin samples were H&E histochemically stained. Figures (a) and (b) show low magnification survey views of cross-sections from near the center of the injury of ACT peptide and control respectively. The wound edge (marked by the small arrows), bounded by skin of normal histological appearance, can be seen in both cases. A black rectangle is placed over the images in (a) and (b) near the center of each injury. The histological structures within these two rectangles are shown at higher magnification in (c) and (d) for the ACT peptide and control tissues respectively. It is evident that tissue within the ACT peptide treated injury locus has considerably more complexity. At the external surface of the ACT treated wound, there is a continuous layer of epithelial cells indicating that re-epithelization of the injured surface is complete, albeit that the epithelium is as yet relatively thin near the center of the wound (c). Regenerating hair follicles can already be seen differentiating de novo from stem cells in the new epithelium covering the healed injury (c, small arrows). By comparison, re-epithelization of the injury surface is incomplete and there is no sign of regenerating hair follicles in the epithelium of the control injury (d). Beneath the reformed epithelium of the ACT peptide treated injured skin, considerable restoration of normal structural complexity is seen, with glandular structures, fibrous and connective tissues, vascular tissues, muscle and fat cells all in evidence (a, c). As with, the hair follicles this tissue complexity was regenerated by differentiation of stem cells. By contrast, in the control injury the wound tissue is completely dominated by a uniform and large plug of fibrous scar tissue (b, d), with other complexity of tissue structure not particularly in evidence within this scar tissue FIG. 9 shows that ACT peptides reduce inflammation, improve healing and reduce scarring following excisional skin injury in adult mice. Anesthetized adult mice had 2 small (5 mm diameter) excisional skin wounds made by fine surgical scissors on the neck and (upper) back. The boundaries of the injuries were demarcated by a 5 mm wide circular template cut in a plastic sheet. 50-60 µl of a solution of 20% pluronic gel containing either no (control) or one of the ACT peptides (ACT 2-SEQ ID NO: 1, ACT 1—SEQ ID NO:2, ACT 3-SEQ ID NO:3, ACT 4-SEQ ID NO:4, ACT 5-SEQ ID NO:5) dissolved at concentrations of 100 µM were then applied to the excisional injuries. Control or ACT peptide-containing gel was applied subsequently 24 hours after the initial application. No further applications of control and ACT peptide-containing gel were made after the second application. It can be noted in the case of ACT 1 (e-h), ACT 2 (i-l), ACT 3 (m-p), and ACT 5 (u-x) peptides that excisional injuries closed faster, were significantly less inflamed in appearance, healed faster and scarred less than the control injury that received no ACT peptide (a-d) over the 240 hour time course (10 days). The ACT 4 peptide (q-t) also showed modest improvement in healing over the control during the time course, although less so than other peptides. Note that the same wound on the same animal is shown at the different time points during the healing time course.

Figure 10:
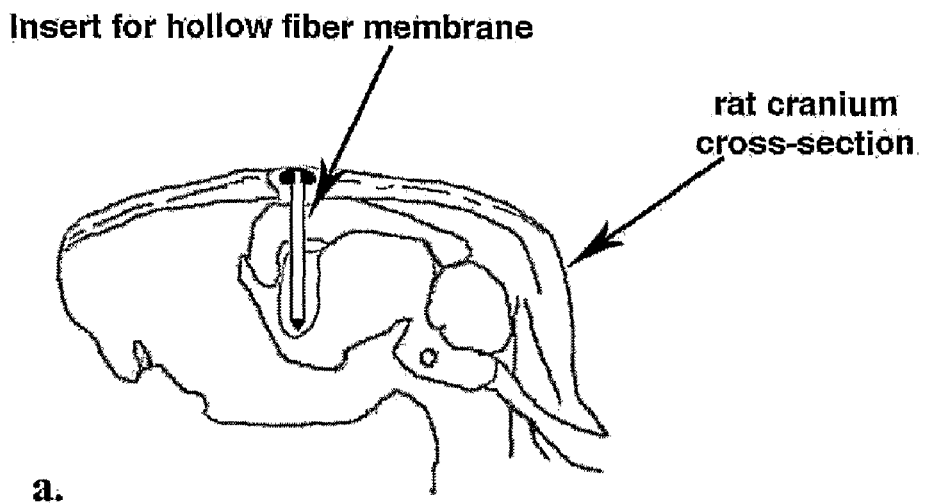
Figure 10:
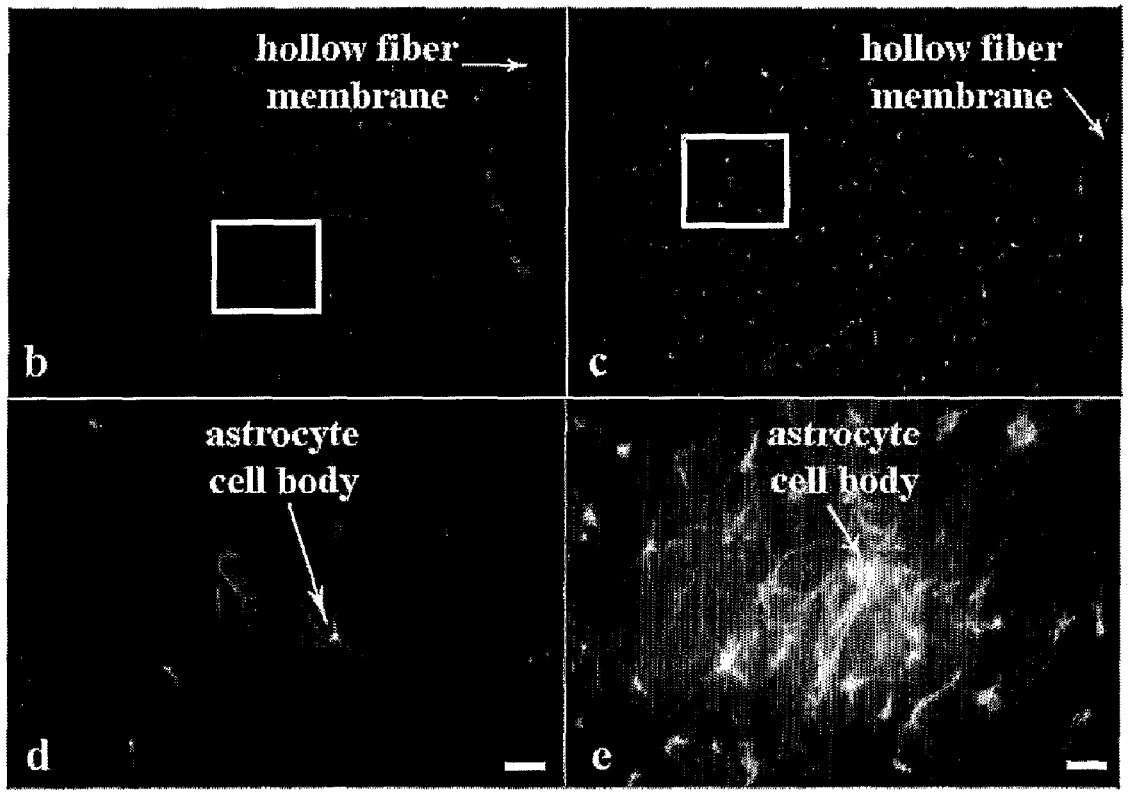

FIG. 10 shows that ACT peptide reduces the number and density of glial scar forming astrocytes following penetration injury of brain in an adult rat. (b) and (c) show low magnification survey views of sections of brain tissue (cortex) surrounding hollow fiber membrane (HFM) implants filled with ACT peptide (100 µM) plus vehicle gel (b) or collagen vehicle gel alone as control (c). In the control tissue (c), a high density of immunolabeled GFAP-positive astrocytes is observed near the site of injury caused by the HFM. The density of these cells appears to diminish slightly distal from the injury. By contrast, a much lower density of GFAP-positive astrocytes is observed adjacent the HFM filled with ACT peptide (b). Indeed, the levels of GFAP positive cells are not dissimilar to those seen in normal uninjured brain tissue. The regions of tissue within the white rectangles in figures (b) and (c) are shown at higher magnification in (d) and (e) respectively. In the brain injury treated by ACT peptide (d), it can be seen that GFAP-positive astrocytes are not only less numerous, but are also smaller than those seen in the control injury (e).

Figure 11:
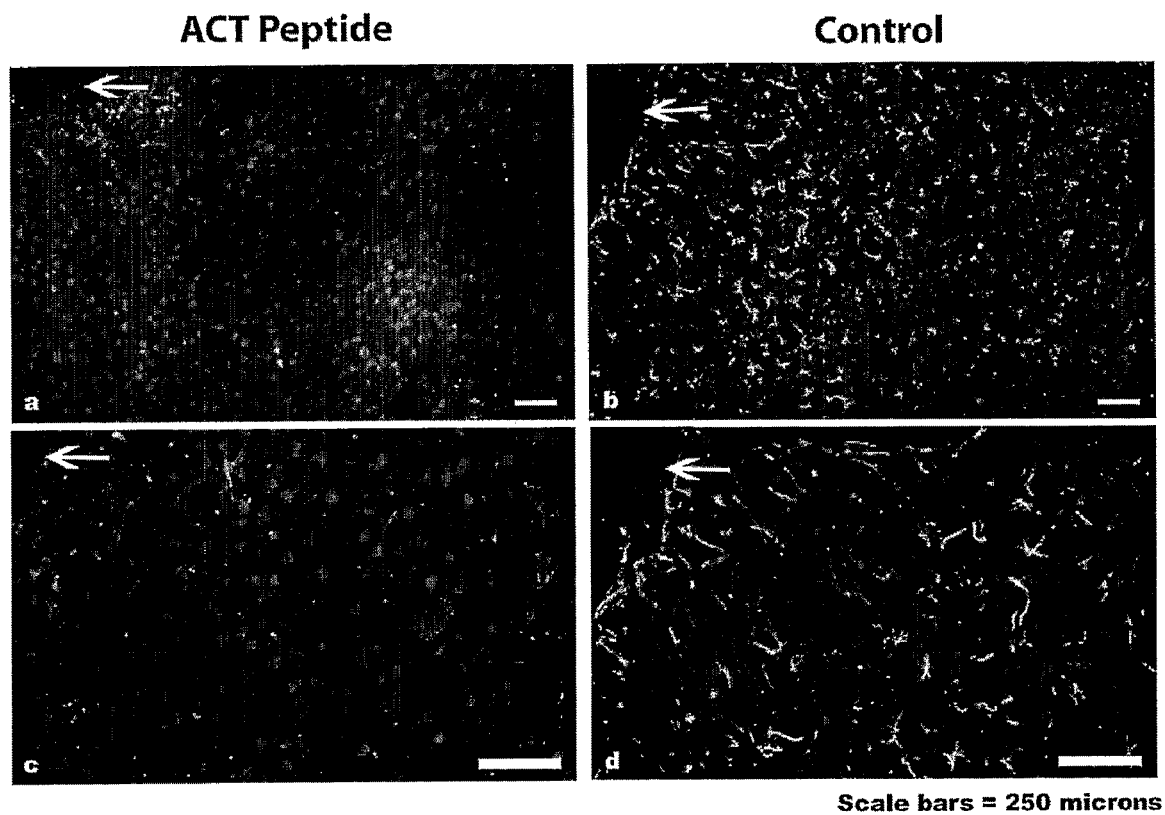

FIG. 11 shows that ACT peptide promotes neuronal maintenance and neuronal regeneration following penetration injury of brain in an adult rat. (a) and (b) show low magnification survey views of sections of brain tissue (cortex) surrounding HFM implants (implant or injury border is shown by arrows) filled with control collagen vehicle gel or ACT peptide plus vehicle gel at 1 week following brain penetration injury. In the control tissue (b), a high density of immunolabeled GFAP-positive astrocytes and a low density of NeuN immunolabeled neurons are observed near the site of injury caused by the HFM. The density of these cells appears to diminish and increase, respectively, distal from the HFM. By contrast, a much lower density of GFAP-positive astrocytes and higher numbers NeuN immunolabeled neurons are observed proximal (as well as distal) to the HFM filled with ACT peptide (a). The areas in (a) and (b) proximal to the HFMs are shown at high magnification views in (c) and (b), respectively. Again, in the control tissue (d) a striking increase in the density of GFAP-positive astrocytes and a reduced density of NeuN-positive neurons is observed compared to ACT peptide treated tissue (c). A complementary pattern is observed near the HFM containing ACT peptide, with NeuN positive neurons predominating over astrocytes (c). Interestingly, the high magnification view shown in (c) reveals a high frequency of neurons in the process of fission relative to the control (d).

DETAILED DESCRIPTION OF THE INVENTION

The disclosed method and compositions may be understood more readily by reference to the following detailed description of particular embodiments and the Examples included therein and to the Figures and their previous and following description.

Provided is an isolated polypeptide comprising a carboxy-terminal amino acid sequence of an alpha Connexin (also referred to herein as an alpha Connexin carboxy-Terminal (ACT) polypeptide), or a conservative variant thereof. In one aspect, following tissue injury, the provided ACT polypeptide reduces inflammation, promotes healing, reduces scarring, increases tensile strength, and promotes complex tissue regeneration. In another aspect, the provided polypeptide increases the extent of gap junctional channel aggregates formed from Connexins.

It is to be understood that the disclosed compositions and methods are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a vector is disclosed and discussed and a number of vector components including the promoters are discussed, each and every combination and permutation of promoters and other vector components and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A variety of sequences are provided herein and these and others can be found in Genbank at www.pubmed.gov. Those of skill in the art understand how to resolve sequence discrepancies and differences and to adjust the compositions and methods relating to a particular sequence to other related sequences. Primers and/or probes can be designed for any sequence given the information disclosed herein and known in the art.

The herein provided polypeptide can be any polypeptide comprising the carboxy-terminal most amino acids of an alpha Connexin, wherein the polypeptide does not comprise the full-length alpha Connexin protein. Thus, in one aspect, the provided polypeptide does not comprise the cytoplasmic N-terminal domain of the alpha Connexin. In another aspect, the provided polypeptide does not comprise the two extracellular domains of the alpha Connexin. In another aspect, the provided polypeptide does not comprise the four transmembrane domains of the alpha Connexin. In another aspect, the provided polypeptide does not comprise the cytoplasmic loop domain of the alpha Connexin. In another aspect, the provided polypeptide does not comprise that part of the sequence of the cytoplasmic carboxyl terminal domain of the alpha Connexin proximal to the fourth transmembrane domain. There is a conserved proline or glycine residue in alpha Connexins consistently positioned some 17 to 30 amino acids from the carboxyl terminal-most amino acid (Table 2). For example, for human Cx43 a proline residue at amino acid 363 is positioned 19 amino acids back from the carboxyl terminal most isoleucine. In another example, for chick Cx43 a proline residue at amino acid 362 is positioned 18 amino acids back from the carboxyl terminal-most isoleucine. In another example, for human Cx45 a glycine residue at amino acid 377 is positioned 19 amino acids back from the carboxyl terminal most isoleucine. In another example for rat Cx33, a proline residue at amino acid 258 is positioned 28 amino acids back from the carboxyl terminal most methionine. Thus, in another aspect, the provided polypeptide does not comprise amino acids proximal to said conserved proline or glycine residue of the alpha Connexin. Thus, the provided polypeptide can comprise the c-terminal-most 4 to 30 amino acids of the alpha Connexin, including the c-terminal most 4, 5, 6, 7, 8, 9, 10, 11, 12, 13, 14, 15, 16, 17, 18, 19, 20, 21, 22, 23, 24, 25, 26, 27, 28, 29, 30 amino acids of the alpha Connexin.

The carboxy-terminal most amino acids of an alpha Connexin in the provided peptides can be flanked by non-alpha Connexin or non-ACT peptide Connexin amino acids. Examples of the flanking non-alpha Connexin and non-ACT Connexin amino acids are provided herein. An example of non-ACT Connexin amino acids are the carboxy-terminal 20 to 120 amino acids of human Cx43 (SEQ ID NO: 72). Another example would be the carboxy-terminal 20 to 120 amino acids of chick Cx43 (SEQ ID NO: 73). Another example would be the carboxy-terminal 20 to 120 amino acids of human Cx45 (SEQ ID NO: 74). Another example would be the carboxy-terminal 20 to 120 amino acids of chick Cx45 (SEQ ID NO: 75). Another example would be the carboxy-terminal 20 to 120 amino of human Cx37 (SEQ ID NO: 76). Another example would be the carboxy-terminal 20 to 120 amino acids of rat Cx33 (SEQ ID NO: 77).

An example of a non-alpha Connexin is the 239 amino acid sequence of enhanced green fluorescent protein (ACT1 is shown functionally fused to GFP in FIG. 4; SEQ ID NO: 78). In another aspect, given that ACT1 is shown to be functional when fused to the carboxy terminus of the 239 amino acid sequence of GFP (e.g., FIG. 4), ACT peptides are expected to retain function when flanked with non-Connexin polypeptides of up to at least 239 amino acids. Indeed, as long as the ACT sequence is maintained as the free carboxy terminus of a given polypeptide, and the ACT peptide is able to access its targets. Thus, polypeptides exceeding 239 amino acids in addition to the ACT peptide can function in reducing inflammation, promoting healing, increasing tensile strength, reducing scarring and promoting tissue regeneration following injury.

Connexins are the sub-unit protein of the gap junction channel which is responsible for intercellular communication (Goodenough and Paul, 2003). Based on patterns of conservation of nucleotide sequence, the genes encoding Connexin proteins are divided into two families termed the alpha and beta Connexin genes. The carboxy-terminal-most amino acid sequences of alpha Connexins are characterized by multiple distinctive and conserved features (see Table 2). This conservation of organization is consistent with the ability of ACT peptides to form distinctive 3D structures, interact with multiple partnering proteins, mediate interactions with lipids and membranes, interact with nucleic acids including DNA, transit and/or block membrane channels and provide consensus motifs for proteolytic cleavage, protein cross-linking, ADP-ribosylation, glycosylation and phosphorylation. Thus, the provided polypeptide interacts with a domain of a protein that normally mediates the binding of said protein to the carboxy-terminus of an alpha Connexin. For example, nephroblastoma overexpressed protein (NOV) interacts with a Cx43 c-terminal domain (Fu et al., J Biol. Chem. 2004 279(35):36943-50). It is considered that this and other proteins interact with the carboxy-terminus of alpha Connexins and further interact with other proteins forming a macromolecular complex. Thus, the provided polypeptide can inhibit the operation of a molecular machine, such as, for example, one involved in regulating the aggregation of Cx43 gap junction channels.

As used herein, "inhibit," "inhibiting," and "inhibition" mean to decrease an activity, response, condition, disease, or other biological parameter. This can include, but is not limited to, the complete loss of activity, response, condition, or disease. This can also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

The ACT sequence of the provided polypeptide can be from any alpha Connexin. Thus, the alpha Connexin component of the provided polypeptide can be from a human, murine, bovine, monotrene, marsupial, primate, rodent, cetacean, mammalian, avian, reptilian, amphibian, piscine, chordate, protochordate or other alpha Connexin.

Thus, the provided polypeptide can comprise an ACT of a Connexin selected from the group consisting of mouse Connexin 47, human Connexin 47, Human Connexin 46.6, Cow Connexin 46.6, Mouse Connexin 30.2, Rat Connexin 30.2, Human Connexin 31.9, Dog Connexin 31.9, Sheep Connexin 44, Cow Connexin 44, Rat Connexin 33, Mouse Connexin 33, Human Connexin 36, mouse Connexin 36, rat Connexin 36, dog Connexin 36, chick Connexin 36, zebrafish Connexin 36, morone Connexin 35, morone Connexin 35, Cynops Connexin 35, Tetraodon Connexin 36, human Connexin 37, chimp Connexin 37, dog Connexin 37, Cricetulus Connexin 37, Mouse Connexin 37, *Mesocricetus* Connexin 37, Rat Connexin 37, mouse Connexin 39, rat Connexin 39, human Connexin 40.1, *Xenopus* Connexin 38, Zebrafish Connexin 39.9, Human Connexin 40, Chimp Connexin 40, dog Connexin 40, cow Connexin 40, mouse Connexin 40, rat Connexin 40, Cricetulus Connexin 40, Chick Connexin 40, human Connexin 43, *Cercopithecus* Connexin 43, *Oryctolagus* Connexin 43, *Spermophilus* Connexin 43, *Cricetulus* Connexin 43, *Phodopus* Connexin 43, Rat Connexin 43, Sus Connexin 43, *Mesocricetus* Connexin 43, Mouse Connexin 43, Cavia Connexin 43, Cow Connexin 43, *Erinaceus* Connexin 43, Chick Connexin 43, *Xenopus* Connexin 43, *Oryctolagus* Connexin 43, *Cyprinus* Connexin 43, Zebrafish Connexin 43, *Danio aequipinnatus* Connexin 43, Zebrafish Connexin 43.4, Zebrafish Connexin 44.2, Zebrafish Connexin 44.1, human Connexin 45, chimp Connexin 45, dog Connexin 45, mouse Connexin 45, cow Connexin 45, rat Connexin 45, chick Connexin 45, Tetraodon Connexin 45, chick Connexin 45, human Connexin 46, chimp Connexin 46, mouse Connexin 46, dog Connexin 46, rat Connexin 46, *Mesocricetus* Connexin 46, *Cricetulus* Connexin 46, Chick Connexin 56, Zebrafish Connexin 39.9 cow Connexin 49, human Connexin 50, chimp Connexin 50, rat Connexin 50, mouse Connexin 50, dog Connexin 50, sheep Connexin 49, *Mesocricetus* Connexin 50, *Cricetulus* Connexin 50, Chick Connexin 50, human Connexin 59, or other alpha Connexin. Amino acid sequences for alpha connexins are known in the art and include those identified in Table 1 by accession number.

TABLE 1

Alpha Connexins

| Protein | Accession No. |
|---|---|
| mouse Connexin 47 | NP_536702 |
| human Connexin 47 | AAH89439 |
| Human Connexin46.6 | AAB94511 |
| Cow Connexin 46.6 | XP_582393 |
| Mouse Connexin 30.2 | NP_848711 |
| Rat Connexin 30.2 | XP_343966 |
| Human Connexin 31.9 | AAM18801 |
| Dog Connexin 31.9 | XP_548134 |
| Sheep Connexin 44 | AAD56220 |
| Cow Connexin 44 | I46053 |
| Rat Connexin 33 | P28233 |
| Mouse Connexin 33 | AAR28037 |
| Human Connexin 36 | Q9UKL4 |
| mouse Connexin 36 | NP_034420 |
| rat Connexin 36 | NP_062154 |
| dog Connexin 36 | XP_544602 |
| chick Connexin 36 | NP_989913 |
| zebrafish Connexin 36 | NP_919401 |
| *morone* Connexin 35 | AAC31884 |
| *morone* Connexin 35 | AAC31885 |
| *Cynops* Connexin 35 | BAC22077 |
| *Tetraodon* Connexin 36 | CAG06428 |
| human Connexin 37 | I55593 |
| chimp Connexin 37 | XP_524658 |
| dog Connexin 37 | XP_539602 |
| *Cricetulus* Connexin 37 | AAR98615 |
| Mouse Connexin 37 | AAH56613 |
| *Mesocricetus* Connexin37 | AAS83433 |
| Rat Connexin37 | AAH86576 |
| mouse Connexin 39 | NP_694726 |
| rat Connexin 39 | AAN17801 |
| human Connexin 40.1 | NP_699199 |
| *Xenopus* Connexin38 | AAH73347 |
| Zebrafish Connexin 39.9 | NP_997991 |
| Human Connexin 40 | NP_859054 |
| Chimp Connexin 40 | XP_513754 |
| dog Connexin 40 | XP_540273 |
| cow Connexin 40 | XP_587676 |
| mouse Connexin 40 | AAH53054 |
| rat Connexin 40 | AAH70935 |
| *Cricetulus* Connexin 40 | AAP37454 |

TABLE 1-continued

Alpha Connexins

| Protein | Accession No. |
|---|---|
| Chick Connexin 40 | NP_990835 |
| human Connexin 43 | P17302 |
| *Cercopithecus* Connexin 43 | AAR33082 |
| *Oryctolagus* Connexin 43 | AAR33084 |
| *Spermophilus* Connexin 43 | AAR33086 |
| *Cricetulus* Connexin 43 | AAO61858 |
| *Phodopus* Connexin 43 | AAR33085 |
| Rat Connexin 43 | AAH81842 |
| *Sus* Connexin 43 | AAR33087 |
| *Mesocricetus* Connexin 43 | AAO61857 |
| Mouse Connexin 43 | AAH55375 |
| *Cavia* Connexin 43 | AAU06305 |
| Cow Connexin 43 | NP_776493 |
| *Erinaceus* Connexin 43 | AAR33083 |
| Chick Connexin 43 | AAA53027 |
| *Xenopus* Connexin 43 | NP_988856 |
| *Oryctolagus* Connexin 43 | AAS89649 |
| *Cyprinus* Connexin 43 | AAG17938 |
| Zebrafish Connexin 43 | CAH69066 |
| *Danio aequipinnatus* Connexin 43 | AAC19098 |
| Zebrafish Connexin 43.4 | NP_571144 |
| Zebrafish Connexin 44.2 | AAH45279 |
| Zebrafish Connexin 44.1 | NP_5718.84 |
| human Connexin45 | I38430 |
| chimp Connexin45 | XP_511557 |
| dog Connexin 45 | XP_548059 |
| mouse Connexin 45 | AAH71230 |
| cow Connexin 45 | XP_588395 |
| rat Connexin 45 | AAN17802 |
| chick Connexin45 | NP_990834 |
| *Tetraodon* Connexin 45 | CAF93782 |
| chick Connexin 45.6 | I50219 |
| human Connexin 46 | NP_068773 |
| chimp Connexin 46 | XP_522616 |
| mouse Connexin 46 | NP_058671 |
| dog Connexin 46 | XP_543178 |
| rat Connexin 46 | NP_077352 |
| *Mesocricetus* Connexin 46 | AAS83437 |
| *Cricetulus* Connexin 46 | AAS77618 |
| Chick Connexin 56 | A45338 |
| Zebrafish Connexin 39.9 | NP_997991 |
| cow Connexin 49 | XP_602360 |
| human Connexin 50 | P48165 |
| chimp Connexin 50 | XP_524857 |
| rat Connexin 50 | NP_703195 |
| mouse Connexin 50 | AAG59880 |
| dog Connexin 50 | XP_540274 |
| sheep Connexin 49 | AAP01367 |
| *Mesocricetus* Connexin 50 | AAS83438 |
| *Cricetulus* Connexin 50 | AAR98618 |
| Chick Connexin 50 | BAA05381 |
| human Connexin 59 | AAG09406 |

Thus, the provided polypeptide can comprise the amino acid sequence SEQ ID NO:1, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:43, SEQ ID NO:90 or ID NO:91 or conservative variants or fragments thereof.

The 20-30 carboxy-terminal-most amino acid sequence of alpha Connexins are characterized by a distinctive and conserved organization. This distinctive and conserved organization would include a type II PDZ binding motif ($\Phi$-x-$\Phi$; wherein x=any amino acid and $\Phi$=a Hydrophobic amino acid; e.g., Table 2, BOLD) and proximal to this motif, Proline (P) and/or Glycine (G) hinge residues; a high frequency phospho-Serine (S) and/or phospho-Threonine (T) residues; and a high frequency of positively charged Arginine (R), Lysine (K) and negatively charged Aspartic acid (D) or Glutamic acid (E) amino acids. For many alpha Connexins, the P and G residues occur in clustered motifs (e.g., Table 2, italicized) proximal to the carboxy-terminal type II PDZ binding motif. The S and T phosphor-amino acids of most alpha Connexins also are typically organized in clustered, repeat-like motifs (e.g., Table 2, underlined). This organization is particularly the case for Cx43, where 90% of 20 carboxyl terminal-most amino acids are comprised of the latter seven amino acids. In a further example of the high conservation of the sequence, ACT peptide organization of Cx43 is highly conserved from humans to fish (e.g., compare Cx43 ACT sequences for humans and zebrafish in Table 2). In another example, the ACT peptide organization of Cx45 is highly conserved from humans to birds (e.g., compare Cx45 ACT sequences for humans and chick in Table 2).). In another example, the ACT peptide organization of Cx36 is highly conserved from primates to fish (e.g., compare Cx36 ACT sequences for chimp and zebrafish in Table 2).

PDZ domains were originally identified as conserved sequence elements within the postsynaptic density protein PSD95/SAP90, the *Drosophila* tumor suppressor dlg-A, and the tight junction protein ZO-1. Although originally referred to as GLGF or DHR motifs, they are now known by an acronym representing these first three PDZ-containing proteins (PSD95/DLG/ZO-1). These 80-90 amino acid sequences have now been identified in well over 75 proteins and are characteristically expressed in multiple copies within a single protein. Thus, in one aspect, the provided polypeptide can inhibit the binding of an alpha Connexin to a protein comprising a PDZ domain. The PDZ domain is a specific type of protein-interaction module that has a structurally well-defined interaction 'pocket' that can be filled by a PDZ-binding motif, referred to herein as a "PDZ motif". PDZ motifs are consensus sequences that are normally, but not always, located at the extreme intracellular carboxyl termi-

TABLE 2

Alpha Connexin Carboxy-Terminal (ACT) Amino Acid Sequences

| Gene | Sequence | SEQ ID NO |
|---|---|---|
| Human alpha Cx43 | P SSRA SSRA SSR PRP D DLEI | (SEQ ID NO:1) |
| Chick alpha Cx43 | P S RA SSRA SSR PPR D DLEI | (SEQ ID NO:29) |
| Zebrafish alpha Cx43 | P CSRA SSRM SSRA R P D DLDV | (SEQ ID NO:90) |
| Human alpha Cx45 | G SNKS TA SSKS GDG KN SVWI | (SEQ ID NO:30) |
| Chick alpha Cx45 | G SNKSS A SSKS GDG KN SVWI | (SEQ ID NO:31) |
| Human alpha Cx46 | G RA SKAS RASS $G_{ERAR}P_{DLAI}$ | (SEQ ID NO:32) |
| Human alpha Cx46.6 | G SASS RD $G_K$ TVWI | (SEQ ID NO:33) |
| Chimp alpha Cx36 | P RVSV PNFG R TQ SSDSAYV | (SEQ ID NO:34) |
| Chick alpha Cx36 | P RMSM PNFG R TQ SSD SAYV | (SEQ ID NO:35) |
| Zebrafish alpha Cx36 | P RMSM PNFG R TQ SSD S AYV | (SEQ ID NO:91) |
| Human alpha Cx47 | P RAGSEK G SASS R DG KT TVWI | (SEQ ID NO:36) |
| Human alpha Cx40 | G HRL $P_H G_{YHSDKRRL}$ SKASS KARSD DLSV | (SEQ ID NO:37) |
| Human alpha Cx50 | P ELTTDDAR P LSRL SKASS RARSD DLTV | (SEQ ID NO:38) |
| Human alpha Cx59 | P NHVV SLTN NLI GRRVP T DLQI | (SEQ ID NO:39) |
| Rat alpha Cx33 | P S CV SSS A VLTTIC SS DQVV PVG L SS FYM | (SEQ ID NO:40) |
| Sheep alpha Cx44 | G R SSKA SKSS GG RARAA DLAI | (SEQ ID NO:41) |
| Human beta Cx26 | LC YLLIR YCSGK SKKPV | (SEQ ID NO:42) |

Thus, in one aspect, the provided polypeptide comprises one, two, three or all of the amino acid motifs selected from the group consisting of 1) a type II PDZ binding motif, 2) Proline (P) and/or Glycine (G) hinge residues; 3) clusters of phospho-Serine (S) and/or phospho-Threonine (T) residues; and 4) a high frequency of positively charged Arginine (R) and Lysine (K) and negatively charged Aspartic acid (D) and/or Glutamic acid (E) amino acids). In another aspect, the provided polypeptide comprises a type II PDZ binding motif at the carboxy-terminus, Proline (P) and/or Glycine (G) hinge residues proximal to the PDZ binding motif, and positively charged residues (K, R, D, E) proximal to the hinge residues.

nus. Four types of PDZ motifs have been classified: type I (S/T-x-Φ), type II (Φ-x-Φ), type III (Ψ-x-Φ) and type IV (D-x-V), where x is any amino acid, Φ is a hydrophobic residue (V, I, L, A, G, W, C, M, F) and Ψ is a basic, hydrophilic residue (H, R, K). (Songyang, Z., et al. 1997. Science 275, 73-77). Thus, in one aspect, the provided polypeptide comprises a type II PDZ binding motif.

It is noted that the 18 carboxy-terminal-most amino acid sequence of alpha Cx37 represents an exceptional variation on the ACT peptide theme. The Cx37 ACT-like sequence is GQKPPSRPSSSASKKQ*YV (SEQ ID NO: 43). Thus the carboxy terminal 4 amino acids of Cx37 conform only in part to a type II PDZ binding domain. Instead of a classical type II PDZ binding domain, Cx37 has a neutral Q* at position 2 where a hydrophobic amino acid would be expected. As such Cx37 comprises what might be termed a type II PDZ binding domain-like sequence. Nonetheless, Cx37 strictly maintains all other aspects of ACT peptide organization including clustered serine residues, frequent R and K residues and a P-rich sequence proximal to the PDZ binding domain-like sequence. Given this overall level of conservation of ACT-like organization in common with the other >70 alpha Connexins listed above, it is understood that the Cx37 ACT-like carboxy terminus functions in the provided capacity.

For comparison, the beta Connexin Cx26 is shown in Table 2. Cx26 has no carboxyl terminal type II PDZ binding motif; less than 30% of the carboxyl terminal most amino acids comprise S, T, R, D or E residues; it has no evidence of motifs proximal to a type II PDZ binding motif or PDZ binding like motif containing clusters of P and G hinge residues; and no evidence of clustered, repeat-like motifs of serine and threonine phospho-amino acids. Cx26 does have three Lysine (K) residues, clustered one after the other near the carboxy terminus of the sequence. However, no alpha Connexin surveyed in the >70 alpha Connexins listed above was found to display this feature of three repeated K residues domain at carboxy terminus (Cx26 is a beta connexin, thus by definition does not have an ACT domain).

As provided herein, the unique functional characteristics of this relatively short stretch of amino acids encompass unexpected roles in reducing inflammation, promoting healing, reducing scarring, increasing tensile strength, and promoting regeneration of complex tissue structure and function following injury in tissues as diverse as skin and brain. Thus, in one aspect, the provided polypeptide comprises a type II PDZ binding motif ($\Phi$-x-$\Phi$; wherein x=any amino acid and $\Phi$=a Hydrophobic amino acid). In another aspect, greater than 50%, 60%, 70%, 80%, 90% of the amino acids of the provided ACT polypeptide is comprised one or more of Proline (P), Glycine (G), phospho-Serine (S), phospho-Threonine (T), Arginine (R), Lysine (K), Aspartic acid (D), or Glutamic acid (E) amino acid residues.

The amino acids Proline (P), Glycine (G), Arginine (R), Lysine (K), Aspartic acid (D), and Glutamic acid (E) are necessary determinants of protein structure and function. Proline and Glycine residues provide for tight turns in the 3D structure of proteins, enabling the generation of folded conformations of the polypeptide required for function. Charged amino acid sequences are often located at the surface of folded proteins and are necessary for chemical interactions mediated by the polypeptide including protein-protein interactions, protein-lipid interactions, enzyme-substrate interactions and protein-nucleic acid interactions. Thus, in another aspect Proline (P) and Glycine (G) Lysine (K), Aspartic acid (D), and Glutamic acid (E) rich regions proximal to the type II PDZ binding motif provide for properties necessary to the provided actions of ACT peptides. In another aspect, the provided polypeptide comprises Proline (P) and Glycine (G) Lysine (K), Aspartic acid (D), and/or Glutamic acid (E) rich regions proximal to the type II PDZ binding motif.

Phosphorylation is the most common post-translational modification of proteins and is crucial for modulating or modifying protein structure and function. Aspects of protein structure and function modified by phosphorylation include protein conformation, protein-protein interactions, protein-lipid interactions, protein-nucleic acid interactions, channel gating, protein trafficking and protein turnover. Thus, in one aspect the phospho-Serine (S) and/or phospho-Threonine (T) rich sequences are necessary for modifying the function of ACT peptides, increasing or decreasing efficacy of the polypeptides in their provided actions. In another aspect, the provided polypeptide comprise Serine (S) and/or phospho-Threonine (T) rich sequences or motifs.

In another example, respecting definition of an ACT peptide, it is highly auspicious, in light of the high degree of tissue/organ regeneration potential in lower animals such as fish, that a methionine occurs near the amino terminus of the ACT sequence of zebrafish Cx43 (Table 2). In addition to encoding methionine, the methionine base pair triplet is an alternate translation start site. If translation initiated from this methionine, the sequence SSRARPDDLDV (SEQ ID NO:90), would be produced. This translation product maintains all the conserved and distinctive features of a canonical ACT peptide. Specifically this peptide comprises a carboxy terminal type II PDZ binding domain and has a domain enriched in P, R and D residues proximal to the PDZ binding domain. In addition, the sequence comprises a clustered S motif, with potential to modulate ACT peptide function at its amino terminal. This raises the interesting prospect that animals with high tissue/organ regeneration potential such as fish may translate ACT peptides sequences directly.

Thus, the provided polypeptide can comprise the c-terminal sequence of human Cx43. Thus, the provided polypeptide can comprise the amino acid sequence SEQ ID NO:1 or SEQ ID NO:2. The polypeptide can comprise 9 amino acids of the carboxy terminus of human Cx40. Thus, the polypeptide can comprise the amino acid sequence SEQ ID NO:5.

When specific proteins are referred to herein, variants, derivatives, and fragments are contemplated. Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known and include, for example, M13 primer mutagenesis and PCR mutagenesis. Amino acid substitutions are typically of single residues, but can occur at a number of different locations at once; insertions usually will be on the order of about from 1 to 10 amino acid residues. Deletions or insertions preferably are made in adjacent pairs, i.e., a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure unless such a change in secondary structure of the mRNA is desired. Substitutional variants are those in which at least one residue has been removed and a different residue inserted in its place. Such substitutions generally are made in accordance with the following Table 3 and are referred to as conservative substitutions.

TABLE 3

Amino Acid Substitutions

| Original Residue | Exemplary Substitutions |
|---|---|
| Ala | Ser |
| Arg | Lys |
| Asn | Gln |
| Asp | Glu |
| Cys | Ser |
| Gln | Asn |
| Glu | Asp |
| Gly | Pro |
| His | Gln |
| Ile | Leu; Val |
| Leu | Ile; Val |
| Lys | Arg; Gln |
| Met | Leu; Ile |
| Phe | Met; Leu; Tyr |
| Pro | Gly |
| Ser | Thr |
| Thr | Ser |
| Trp | Tyr |
| Tyr | Trp; Phe |
| Val | Ile; Leu |

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations shown in Table 3. Conservatively substituted variations of each explicitly disclosed sequence are included within the polypeptides provided herein.

Typically, conservative substitutions have little to no impact on the biological activity of a resulting polypeptide. In a particular example, a conservative substitution is an amino acid substitution in a peptide that does not substantially affect the biological function of the peptide. A peptide can include one or more amino acid substitutions, for example 2-10 conservative substitutions, 2-5 conservative substitutions, 4-9 conservative substitutions, such as 2, 5 or 10 conservative substitutions.

A polypeptide can be produced to contain one or more conservative substitutions by manipulating the nucleotide sequence that encodes that polypeptide using, for example, standard procedures such as site-directed mutagenesis or PCR. Alternatively, a polypeptide can be produced to contain one or more conservative substitutions by using standard peptide synthesis methods. An alanine scan can be used to identify which amino acid residues in a protein can tolerate an amino acid substitution. In one example, the biological activity of the protein is not decreased by more than 25%, for example not more than 20%, for example not more than 10%, when an alanine, or other conservative amino acid (such as those listed below), is substituted for one or more native amino acids.

Further information about conservative substitutions can be found in, among other locations, in Ben-Bassat et al., (*J. Bacteriol.* 169:751-7, 1987), O'Regan et al., (*Gene* 77:237-51, 1989), Sahin-Toth et al., (*Protein Sci.* 3:240-7, 1994), Hochuli et al., (*Bio/Technology* 6:1321-5, 1988) and in standard textbooks of genetics and molecular biology.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that there are numerous amino acid and peptide analogs which can be incorporated into the disclosed compositions. For example, there are numerous D amino acids or amino acids which have a different functional substituent than the amino acids shown in Table 3. The opposite stereoisomers of naturally occurring peptides are disclosed, as well as the stereoisomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., *Methods in Molec. Biol.* 77:43-73 (1991), Zoller, *Current Opinion in Biotechnology,* 3:348-354 (1992); Ibba, *Biotechnology & Genetic Engineering Reviews* 13:197-216 (1995), Cahill et al., *TIBS,* 14(10):400-403 (1989); Benner, *TIB Tech,* 12:158-163 (1994); Ibba and Hennecke, *Bio/technology,* 12:678-682 (1994), all of which are herein incorporated by reference at least for material related to amino acid analogs).

Molecules can be produced that resemble polypeptides, but which are not connected via a natural peptide linkage. For example, linkages for amino acids or amino acid analogs can include —$CH_2NH$—, —$CH_2S$—, —$CH_2$—$CH_2$—, —CH=CH— (cis and trans), —$COCH_2$—, —CH(OH) $CH_2$—, and —$CHH_2SO$— (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., *Int J Pept Prot Res* 14:177-185 (1979) (—$CH_2NH$—, $CH_2CH_2$—); Spatola et al. *Life Sci* 38:1243-1249 (1986) (—CH $H_2$—S); Hann J. *Chem. Soc Perkin Trans. I* 307-314 (1982) (—CH—CH—, cis and trans); Almquist et al. *J. Med. Chem.* 23:1392-1398 (1980) (—$COCH_2$—); Jennings-White et al. *Tetrahedron Lett* 23:2533 (1982) (—$COCH_2$—); Szelke et al. *European Appln,* EP 45665 CA (1982): 97:39405 (1982) (—CH(OH)$CH_2$—); Holladay et al. *Tetrahedron. Lett* 24:4401-4404 (1983) (—C (OH)$CH_2$—); and Hruby *Life Sci* 31:189-199 (1982) (—$CH_2$—S—); each of which is incorporated herein by reference. It is understood that peptide analogs can have more than one atom between the bond atoms, such as b-alanine, g-aminobutyric acid, and the like.

Amino acid analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, greater ability to cross biological barriers (e.g., gut, blood vessels, blood-brain-barrier), and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch *Ann. Rev. Biochem.* 61:387 (1992), incorporated herein by reference).

Thus, the provided polypeptide can comprise a conservative variant of the c-terminus of an alpha Connexin (ACT). As shown in Table 4, an example of a single conservative substitution within the sequence SEQ ID NO:2 is given in the sequence SEQ ID NO:3. An example of three conservative substitutions within the sequence SEQ ID NO:2 is given in the sequence SEQ ID NO:4. Thus, the provided polypeptide can comprise the amino acid SEQ ID NO:3 or SEQ ID NO:4.

TABLE 4

ACT Polypeptide Variants

| Sequence | SEQ ID NO |
|---|---|
| RPRPDDLEI | SEQ ID NO:2 |
| RPRPDDLEV | SEQ ID NO:3 |
| RPRPDDVPV | SEQ ID NO:4 |
| SSRASSRASSRPRPDDLEV | SEQ ID NO:44 |
| RPKPDDLEI | SEQ ID NO:45 |
| SSRASSRASSRPKPDDLEI | SEQ ID NO:46 |
| RPKPDDLDI | SEQ ID NO:47 |
| SSRASSRASSRPRPDDLDI | SEQ ID NO:48 |
| SSRASTRASSRPRPDDLEI | SEQ ID NO:49 |
| RPRPEDLEI | SEQ ID NO:50 |
| SSRASSRASSRPRPEDLEI | SEQ ID NO:51 |
| GDGKNSVWV | SEQ ID NO:52 |
| SKAGSNKSTASSKSGDGKNSVWV | SEQ ID NO:53 |
| GQKPP<u>SRPSSS</u>ASKKLYV | SEQ ID NO: 54 |

It is understood that one way to define any variants, modifications, or derivatives of the disclosed genes and proteins herein is through defining the variants, modification, and derivatives in terms of sequence identity (also referred to herein as homology) to specific known sequences. Specifically disclosed are variants of the nucleic acids and polypeptides herein disclosed which have at least 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent sequence identity to the stated or known sequence. Those of skill in the art readily understand how to determine the sequence identity of two proteins or nucleic acids. For example, the sequence identity can be calculated after aligning the two sequences so that the sequence identity is at its highest level.

Another way of calculating sequence identity can be performed by published algorithms. Optimal alignment of sequences for comparison may be conducted by the local sequence identity algorithm of Smith and Waterman Adv. Appl. Math. 2: 482 (1981), by the sequence identity alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection. These references are incorporated herein by reference in their entirety for the methods of calculating sequence identity.

The same types of sequence identity can be obtained for nucleic acids by, for example, the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment.

Thus, the provided polypeptide can comprise an amino acid sequence with at least 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent sequence identity to the c-terminus of an alpha Connexin (ACT). Thus, in one aspect, the provided polypeptide comprises an amino acid sequence with at least 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent sequence identity to SEQ ID NO:1, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO: 90 or SEQ ID NO:91. As an example, provided is a polypeptide (SEQ ID NO:4) having 66% sequence identity to the same stretch of 9 amino acids occurring on the carboxy-terminus of human Cx43 (SEQ ID NO:2).

The herein provided polypeptides can be added directly to a tissue injury in a subject. However, efficiency of cytoplasmic localization of the provided polypeptide is enhanced by cellular internalization transporter chemically linked in cis or trans with the polypeptide. Efficiency of cell internalization transporters are enhanced further by light or co-transduction of cells with Tat-HA peptide.

Thus, the provided polypeptide can comprise a cellular internalization transporter or sequence. The cellular internalization sequence can be any internalization sequence known or newly discovered in the art, or conservative variants thereof. Non-limiting examples of cellular internalization transporters and sequences include Antennapedia sequences, TAT, HIV-Tat, Penetratin, Antp-3A (Antp mutant), Buforin II, Transportan, MAP (model amphipathic peptide), K-FGF, Ku70, Prion, pVEC, Pep-1, SynB1, Pep-7, HN-1, BGSC (Bis-Guanidinium-Spermidine-Cholesterol, and BGTC (Bis-Guanidinium-Tren-Cholesterol) (see Table 5).

TABLE 5

Cell Internalization Transporters

| Name | Sequence | SEQ ID NO |
|---|---|---|
| Antp | RQPKIWFPNRRKPWKK | (SEQ ID NO: 7) |
| HIV-Tat | GRKKRRQRPPQ | (SEQ ID NO: 14) |
| Penetratin | RQIKIWFQNIRRMKWKK | (SEQ ID NO: 15) |
| Antp-3A | RQIAIWFQNRRMKWAA | (SEQ ID NO: 16) |
| Tat | RKKRRQRRR | (SEQ ID NO: 17) |
| Buforin II | TRSSRAGLQFPVGRVHRLLRK | (SEQ ID NO: 18) |
| Transportan | GWTLNSAGYLLGKINKALAALAKKIL | (SEQ ID NO: 19) |
| model amphipathic peptide (MAP) | KLALKLALKALKAALKLA | (SEQ ID NO: 20) |
| K-FGF | AAVALLPAVLLALLAP | (SEQ ID NO: 21) |
| Ku70 | VPMLK-PMLKE | (SEQ ID NO: 22) |
| Prion | MANLGYWLLALFVTMWTDVGLCKKRPKP | (SEQ ID NO: 23) |
| pVEC | LLIILRRRIRKQAHAHSK | (SEQ ID NO: 24) |
| Pep-1 | KETWWETWWTEWSQPKKKRKV | (SEQ ID NO: 25) |
| SynB1 | RGGRLSYSRRRFSTSTGR | (SEQ ID NO: 26) |
| Pep-7 | SDLWEMMMVSLACQY | (SEQ ID NO: 27) |
| HN-1 | TSPLNIHNGQKL | (SEQ ID NO: 28) |
| BGSC (Bis-Guanidinium-Spermidine-Cholesterol) | | |
| BGTC (Bis-Guanidinium-Tren-Cholesterol) | | |

Thus, the provided polypeptide can further comprise the amino acid sequence SEQ ID NO:7, SEQ ID NO:14 (Bucci, M. et al. 2000. Nat. Med. 6, 1362-1367), SEQ ID NO:15 (Derossi, D., et al. 1994. Biol. Chem. 269, 10444-10450), SEQ ID NO:16 (Fischer, P. M. et al 2000. J. Pept. Res. 55, 163-172), SEQ ID NO:17 (Frankel, A. D. & Pabo, C. O. 1988. Cell 55, 1189-1193; Green, M. & Loewenstein, P. M. 1988. Cell 55, 1179-1188), SEQ ID NO:18 (Park, C. B., et al. 2000. Proc. Natl. Acad. Sci. USA 97, 8245-8250), SEQ ID NO:19 (Pooga, M., et al. 1998. FASEB J. 12, 67-77), SEQ ID NO:20 (Oehlke, J. et al. 1998. Biochim. Biophys. Acta. 1414, 127-139), SEQ ID NO:21 (Lin, Y. Z., et al. 1995. J. Biol. Chem. 270, 14255-14258), SEQ ID NO:22 (Sawada, M., et al. 2003. Nature Cell Biol. 5, 352-357), SEQ ID NO:23 (Lundberg, P. et al. 2002. Biochem. Biophys. Res. Commun. 299, 85-90), SEQ ID NO:24 (Elmquist, A., et al. 2001. Exp. Cell Res. 269, 237-244), SEQ ID NO:25 (Morris, M. C., et al. 2001. Nature Biotechnol. 19, 1173-1176), SEQ ID NO:26 (Rousselle, C. et al. 2000. Mol. Pharmacol. 57, 679-686), SEQ ID NO:27 (Gao, C. et al. 2002. Bioorg. Med. Chem. 10, 4057-4065), or SEQ ID NO:28 (Hong, F. D. & Clayman, G. L. 2000. Cancer Res. 60, 6551-6556). The provided polypeptide can further comprise BGSC (Bis-Guanidinium-Spermidine-Cholesterol) or BGTC (Bis-Guanidinium-Tren-Cholesterol) (Vigneron, J. P. et al. 1998. Proc. Natl. Acad. Sci. USA. 93, 9682-9686). The preceding references are hereby incorporated herein by reference in their entirety for the teachings of cellular internalization vectors and sequences. Any other internalization sequences now known or later identified can be combined with a peptide of the invention.

The provided polypeptide can comprise any ACT sequence (e.g., any of the ACT peptides disclosed herein) in combination with any of the herein provided cell internalization sequences. Examples of said combinations are given in Table 6. Thus, the provided polypeptide can comprise an Antennapedia sequence comprising amino acid sequence SEQ ID NO:7. Thus, the provided polypeptide can comprise the amino acid sequence SEQ ID NO:8, SEQ ID NO:9, SEQ ID NO:10, SEQ ID NO:11, or SEQ ID NO:12.

TABLE 6

ACT Polypeptides with Cell Internalization Sequences (CIS)

| CIS/ ACT | Sequence | SEQ ID NO |
|---|---|---|
| Antp/ ACT 2 | RQPKIWFPNRRKPWKK PSSRASS RASSRPRPDDLEI | SEQ ID NO:8 |
| Antp/ ACT 1 | RQPKIWFPNRRKPWKK RPRPDDL EI | SEQ ID NO:9 |
| Antp/ ACT 3 | RQPKIWFPNRRKPWKK RPRPDDL EV | SEQ ID NO:10 |
| Antp/ ACT 4 | RQPKIWFPNRRKPWKK RPRPDDV PV | SEQ ID NO:11 |
| Antp/ ACT 5 | RQPKIWFPNRRKPWKK KARSDDL SV | SEQ ID NO:12 |
| HIV-Tat/ ACT 1 | GRKKRRQRPPQ RPRPDDLEI | SEQ ID NO:56 |
| Penetratin/ ACT 1 | RQIKIWFQNRRMKWKK RPRPDDL EI | SEQ ID NO:57 |
| Antp-3A/ ACT 1 | RQIAIWFQNRRMKWAA RPRPDDL EI | SEQ ID NO:58 |
| Tat/ ACT 1 | RKKRRQRRR RPRPDDLEI | SEQ ID NO:59 |
| Buforin II/ ACT 1 | TRSSRAGLQFPVGRVHRLLRK RP RPDDLEI | SEQ ID NO:60 |
| Transportan/ ACT 1 | GWTLNSAGYLLGKINKALAALAKK IL RPRPDDLEI | SEQ ID NO:61 |
| MAP/ ACT 1 | KLALKLALKALKAALKLA RPRPD DLEI | SEQ ID NO:62 |
| K-FGF/ ACT 1 | AAVALLPAVLLALLAP RPRPDDL EI | SEQ ID NO:63 |
| Ku70/ ACT 1 | VPMLKPMLKE RPRPDDLEI | SEQ ID NO:64 |
| Prion/ ACT 1 | MANLGYWLLALFVTMWTDVGLCKK RPKPRPRPDDLEI | SEQ ID NO:65 |
| pVEC/ ACT 1 | LLIILRRRIRKQAHAHSK RPRPD DLEI | SEQ ID NO:66 |
| Pep-1 ACT 1 | KETWWETWWTEWSQPKKKRKV RP RPDDLEI | SEQ ID NO:67 |
| SynB1/ ACT 1 | RGGRLSYSRRRFSTSTGR RPRPD DLEI | SEQ D NO:68 |
| Pep-7/ ACT 1 | SDLWEMMMVSLACQY RPRPDDLE I | SEQ ID NO:69 |
| HN-1 ACT 1 | TSPLNIHNGQKL RPRPDDLEI | SEQ ID NO:70 |

Also provided are isolated nucleic acids encoding the polypeptides provided herein. The disclosed nucleic acids are made up of for example, nucleotides, nucleotide analogs, or nucleotide substitutes. Non-limiting examples of these and other molecules are discussed herein. It is understood that for example, when a vector is expressed in a cell, the expressed mRNA will typically be made up of A, C, G, and U.

By "isolated nucleic acid" or "purified nucleic acid" is meant DNA that is free of the genes that, in the naturally-occurring genome of the organism from which the DNA of the invention is derived, flank the gene. The term therefore includes, for example, a recombinant DNA which is incorporated into a vector, such as an autonomously replicating plasmid or virus; or incorporated into the genomic DNA of a prokaryote or eukaryote (e.g., a transgene); or which exists as a separate molecule (e.g., a cDNA or a genomic or cDNA fragment produced by PCR, restriction endonuclease digestion, or chemical or in vitro synthesis). It also includes a recombinant DNA which is part of a hybrid gene encoding additional polypeptide sequence. The term "isolated nucleic acid" also refers to RNA, e.g., an mRNA molecule that is encoded by an isolated DNA molecule, or that is chemically synthesized, or that is separated or substantially free from at least some cellular components, e.g., other types of RNA molecules or polypeptide molecules.

Thus, provided is an isolated nucleic acid encoding a polypeptide comprising the amino acid sequence SEQ ID NO:1, SEQ ID NO:2, SEQ ID NO:3, SEQ ID NO:4, SEQ ID NO:5, SEQ ID NO:7, SEQ ID NO:8, SEQ ID NO:9, SEQ ID NO:10, SEQ ID NO:11, or SEQ ID NO:12.

Thus, the provided nucleic acid can comprise the nucleic acid sequence SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87 SEQ ID NO:88, or SEQ ID NO:89.

The herein provided nucleic acid can be operably linked to an expression control sequence. Also provided is a vector comprising one or more of the herein provided nucleic acids, wherein the nucleic acid is operably linked to an expression control sequence. There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991). Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)).

As used herein, plasmid or viral vectors are agents that transport the disclosed nucleic acids, such as SEQ ID NO:6, into the cell without degradation and include a promoter yielding expression of the gene in the cells into which it is delivered. In some embodiments the promoters are derived from either a virus or a retrovirus. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also disclosed are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. Also disclosed is a viral vector which has been engineered so as to suppress the immune response of the host organism, elicited by the viral antigens. Vectors of this type can carry coding regions for Interleukin 8 or 10.

Viral vectors can have higher transaction (ability to introduce genes) abilities than chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

A retrovirus is an animal virus belonging to the virus family of Retroviridae, including any types, subfamilies, genus, or tropisms. Retroviral vectors, in general, are described by Verma, I. M., Retroviral vectors for gene transfer. In Microbiology-1985, American Society for Microbiology, pp. 229-232, Washington, (1985), which is incorporated by reference herein. Examples of methods for using retroviral vectors for gene therapy are described in U.S. Pat. Nos. 4,868,116 and 4,980,286; PCT applications WO 90/02806 and WO 89/07136; and Mulligan, (Science 260:926-932 (1993)); the teachings of which are incorporated herein by reference.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome, contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

The construction of replication-defective adenoviruses has been described (Berkner et al., J. Virology 61:1213-1220 (1987); Massie et al., Mol. Cell. Biol. 6:2872-2883 (1986); Haj-Ahmad et al., J. Virology 57:267-274 (1986); Davidson et al., J. Virology 61:1226-1239 (1987); Zhang "Generation and identification of recombinant adenovirus by liposome-mediated transfection and PCR analysis" BioTechniques 15:868-872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, J. Clin. Invest. 92:1580-1586 (1993); Kirshenbaum, J. Clin. Invest. 92:381-387 (1993); Roessler, J. Clin. Invest. 92:1085-1092 (1993); Moullier, Nature Genetics 4:154-159 (1993); La Salle, Science 259:988-990 (1993); Gomez-Foix, J. Biol. Chem. 267:25129-25134 (1992); Rich, Human Gene Therapy 4:461-476 (1993); Zabner, Nature Genetics 6:75-83 (1994); Guzman, Circulation Research 73:1201-1207 (1993); Bout, Human Gene Therapy 5:3-10 (1994); Zabner, Cell 75:207-216 (1993); Caillaud, Eur. J. Neuroscience 5:1287-1291 (1993); and Ragot, J. Gen. Virology 74:501-507 (1993)). Recombinant adenoviruses achieve gene transduction by binding to specific cell surface receptors, after which the virus is internalized by receptor-mediated endocytosis, in the same manner as wild type or replication-defective adenovirus (Chardonnet and Dales, Virology 40:462-477 (1970); Brown and Burlingham, J. Virology 12:386-396 (1973); Svensson and Persson, J. Virology 55:442-449 (1985); Seth, et al., J. Virol. 51:650-655 (1984); Seth, et al., Mol. Cell. Biol. 4:1528-1533 (1984); Varga et al., J. Virology 65:6061-6070 (1991); Wickham et al., Cell 73:309-319 (1993)).

A viral vector can be one based on an adenovirus which has had the E1 gene removed, and these virons are generated in a cell line such as the human 293 cell line. In one aspect, both the E1 and E3 genes are removed from the adenovirus genome.

Another type of viral vector is based on an adeno-associated virus (AAV). This defective parvovirus can infect many cell types and is nonpathogenic to humans. AAV type vectors can transport about 4 to 5 kb and wild type AAV is known to stably insert into chromosome 19. As an example, this vector can be the P4.1 C vector produced by Avigen, San Francisco, Calif., which can contain the herpes simplex virus thymidine kinase gene, HSV-tk, and/or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorporated by reference for material related to the AAV vector.

The disclosed vectors thus provide DNA molecules which are capable of integration into a mammalian chromosome without substantial toxicity.

The inserted genes in viral and retroviral usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

Molecular genetic experiments with large human herpes viruses have provided a means whereby large heterologous DNA fragments can be cloned, propagated and established in cells permissive for infection with herpes viruses (Sun et al., Nature genetics 8: 33-41, 1994; Cotter and Robertson, Curr Opin Mol Ther 5: 633-644, 1999). These large DNA viruses (herpes simplex virus (HSV) and Epstein-Barr virus (EBV), have the potential to deliver fragments of human heterologous DNA >150 kb to specific cells. EBV recombinants can maintain large pieces of DNA in the infected B-cells as episomal DNA. Individual clones carried human genomic inserts up to 330 kb appeared genetically stable. The maintenance of these episomes requires a specific EBV nuclear protein, EBNA1, constitutively expressed during infection with EBV. Additionally, these vectors can be used for transfection, where large amounts of protein can be generated transiently in vitro. Herpesvirus amplicon systems are also being used to package pieces of DNA>220 kb and to infect cells that can stably maintain DNA as episomes.

Other useful systems include, for example, replicating and host-restricted non-replicating vaccinia virus vectors.

The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed polypeptides, nucleic acids or vectors, for example, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. *Am. J. Resp. Cell. Mol. Biol.* 1:95-100 (1989); Felgner et al. *Proc. Natl. Acad. Sci. USA* 84:7413-7417 (1987); U.S. Pat. No. 4,897, 355. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the disclosed nucleic acid or vector can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

Nucleic acids that are delivered to cells which are to be integrated into the host cell genome, typically contain integration sequences. These sequences are often viral related sequences, particularly when viral based systems are used. These viral integration systems can also be incorporated into nucleic acids which are to be delivered using a non-nucleic acid based system of deliver, such as a liposome, so that the nucleic acid contained in the delivery system can be come integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

The compositions can be delivered to the subject's cells in vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

Promoters controlling transcription from vectors in mammalian host cells may be obtained from various sources, for example, the genomes of viruses such as: polyoma, Simian Virus 40 (SV40), adenovirus, retroviruses, hepatitis-B virus, cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., Nature, 273: 113 (1978)). The immediate early promoter of the human cytomegalovirus is conveniently obtained as a HindIII E restriction fragment (Greenway, P. J. et al., Gene 18: 355-360 (1982)). Of course, promoters from the host cell or related species also are useful herein.

Enhancer generally refers to a sequence of DNA that functions at no fixed distance from the transcription start site and can be either 5' (Laimins, L. et al., Proc. Natl. Acad. Sci. 78: 993 (1981)) or 3' (Lusky, M. L., et al., Mol. Cell. Bio. 3: 1108 (1983)) to the transcription unit. Furthermore, enhancers can be within an intron (Banerji, J. L. et al., Cell 33: 729 (1983)) as well as within the coding sequence itself (Osborne, T. F., et al., Mol. Cell. Bio. 4: 1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, α-fetoprotein and insulin), typically one will use an enhancer from a eukaryotic cell virus for general expression. Examples are the SV40 enhancer on the late side of the replication origin (bp 100-270), the cytomegalovirus early promoter enhancer, the polyoma enhancer on the late side of the replication origin, and adenovirus enhancers.

The promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A promoter of this type is the CMV promoter (650 bases). Other such promoters are SV40 promoters, cytomegalovirus (full length promoter), and retroviral vector LTR.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. The transcription unit can also contain a polyadenylation region. One benefit of this region is that it increases the likelihood that the transcribed unit will be processed and transported like mRNA. The identification and use of polyadenylation signals in expression constructs is well established. Homologous polyadenylation signals can be used in the transgene constructs. In certain transcription units, the polyadenylation region is derived from the SV40 early polyadenylation signal and consists of about 400 bases. Transcribed units an contain other standard sequences alone or in combination with the above sequences improve expression from, or stability of, the construct.

The viral vectors can include nucleic acid sequence encoding a marker product. This marker product is used to determine if the gene has been delivered to the cell and once delivered is being expressed. Example marker genes are the E. Coli lacZ gene, which encodes β-galactosidase, and green fluorescent protein.

In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: Chinese hamster ovary (CHO) DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., J. Molec. Appl. Genet. 1:327 (1982)), mycophenolic acid, (Mulligan, R. C. and Berg, P. Science 209: 1422 (1980)) or hygromycin, (Sugden, B. et al., Mol. Cell. Biol. 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

Also provided is a cell comprising one or more of the herein provided vectors. As used herein, "cell", "cell line", and "cell culture" may be used interchangeably and all such designations include progeny. The disclosed cell can be any cell used to clone or propagate the vectors provided herein. Thus, the cell can be from any primary cell culture or established cell line. The method may be applied to any cell, including prokaryotic or eukaryotic, such as bacterial, plant, animal, and the like. The cell type can be selected by one skilled in the art based on the choice of vector and desired use.

Disclosed are animals produced by the process of transfecting a cell within the animal with any of the nucleic acid molecules or vectors disclosed herein. Disclosed are animals produced by the process of transfecting a cell within the animal any of the nucleic acid molecules or vectors disclosed herein, wherein the animal is a mammal. Also disclosed are animals produced by the process of transfecting a cell within the animal any of the nucleic acid molecules or vectors disclosed herein, wherein the mammal is mouse, rat, rabbit, cow, sheep, pig, or primate.

Provided is a composition comprising one or more of the herein provided polypeptides, nucleic acids, or vectors in a pharmaceutically acceptable carrier. Thus, provided is a composition comprising a combination of two or more of any of the herein provided ACT polypeptides in a pharmaceutically acceptable carrier. For example, provided is a composition comprising SEQ ID NO:1 and SEQ ID NO:5 in a pharmaceutically acceptable carrier.

By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The herein provide composition can further comprise any known or newly discovered substance that can be administered to a wound, tissue injury, site of inflammation or cancer. For example, the provided composition can further comprise one or more of classes of antibiotics (e.g. Aminoglycosides, Cephalosporins, Chloramphenicol, Clindamycin, Erythromycins, Fluoroquinolones, Macrolides, Azolides, Metronidazole, Penicillin's, Tetracycline's, Trimethoprim-sulfamethoxazole, Vancomycin), steroids (e.g. Andranes (e.g. Testosterone), Cholestanes (e.g. Cholesterol), Cholic acids (e.g. Cholic acid), Corticosteroids (e.g. Dexamethasone), Estraenes (e.g. Estradiol), Pregnanes (e.g. Progesterone), narcotic and non-narcotic analgesics (e.g. Morphine, Codeine, Heroin, Hydromorphone, Levorphanol, Meperidine, Methadone, Oxydone, Propoxyphene, Fentanyl, Methadone, Naloxone, Buprenorphine, Butorphanol, Nalbuphine, Pentazocine), chemotherapy (e.g. anti-cancer drugs such as but not limited to Altretamine, Asparaginase, Bleomycin, Busulfan, Carboplatin, Carrnustine, Chlorambucil, Cisplatin, Cladribine, Cyclophosphamide, Cytarabine, Dacarbazine, Diethylstilbesterol, Ethinyl estradiol, Etoposide, Floxuridine, Fludarabine, Fluorouracil, Flutamide, Goserelin, Hydroxyurea, Idarubicin, Ifosfamide, Leuprolide, Levamisole, Lomustine, Mechlorethamine, Medroxyprogesterone, Megestrol, Melphalan, Mercaptopurine, Methotrexate, Mitomycin, Mitotane, Mitoxantrone, Paclitaxel, pentastatin, Pipobroman, Plicamycin, Prednisone, Procarbazine, Streptozocin, Tamoxifen, Teniposide, Vinblastine, Vincristine), anti-inflammatory agents (e.g. Alclofenac; Alclometasone Dipropionate; Algestone Acetonide; alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Decanoate; Deflazacort; Delatestryl; Depo-Testosterone; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lomoxicam; Loteprednol Etabonate; Meclofenamate Sodium; Meclofenamic Acid; Meclorisone Dibutyrate; Mefenamic Acid; Mesalamine; Meseclazone; Mesterolone; Methandrostenolone; Methenolone; Methenolone Acetate; Methylprednisolone Suleptanate; Momiflumate; Nabumetone; Nandrolone; Naproxen; Naproxen Sodium; Naproxol; Nimazone; Olsalazine Sodium; Orgotein; Orpanoxin; Oxandrolane; Oxaprozin; Oxyphenbutazone; Oxymetholone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Stanozolol; Sudoxicam; Sulindac; Suprofen; Talmetacin; Talniflumate; Talosalate; Tebufelone; Tenidap; Tenidap Sodium; Tenoxicam; Tesicam; Tesimide; Testosterone; Testosterone Blends; Tetrydamine; Tiopinac; Tixocortol Pivalate; Tolmetin; Tolmetin Sodium; Triclonide; Triflumidate; Zidometacin; Zomepirac Sodium), or anti-histaminic agents (e.g. Ethanolamines (like diphenhydrmine carbinoxamine), Ethylenediamine (like tripelenamine pyrilamine), Alkylamine (like chlorpheniramine, dexchlorpheniramine, brompheniramine, triprolidine), other anti-histamines like astemizole, loratadine, fexofenadine, Bropheniramine, Clemastine, Acetaminophen, Pseudoephedrine, Triprolidine).

The compositions may be administered topically, orally, or parenterally. For example, the compositions can be administered extracorporeally, intracranially, intravaginally, intraanally, subcutaneously, intradermally, intracardiac, intragastric, intravenously, intramuscularly, by intraperitoneal injection, transdermally, intranasally, or by inhalant. As used herein, "intracranial administration" means the direct delivery of substances to the brain including, for example, intrathecal, intracisternal, intraventricular or trans-sphenoidal delivery via catheter or needle.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation.

The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

The materials may be in solution or suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., Bioconjugate Chem., 2:447-451, (1991); Bagshawe, K. D., Br. J. Cancer, 60:275-281, (1989); Bagshawe, et al., Br. J. Cancer, 58:700-703, (1988); Senter, et al., Bioconjugate Chem., 4:3-9, (1993); Battelli, et al., Cancer Immunol. Immunother., 35:421-425, (1992); Pietersz and McKenzie, Immunolog. Reviews, 129:57-80, (1992); and Roffler, et al., Biochem. Pharmacol, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., Cancer Research, 49:6214-6220, (1989); and Litzinger and Huang, Biochimica et Biophysica Acta, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, DNA and Cell Biology 10:6, 399-409 (1991)).

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution can be from about 5 to about 8, from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels (e.g., poloxamer gel), drops, suppositories, sprays, liquids and powders. Conventional pharmaceutical carriers, aqueous, powder or oily bases, thickeners and the like may be necessary or desirable. The disclosed compositions can be administered, for example, in a microfiber, polymer (e.g., collagen), nanosphere, aerosol, lotion, cream, fabric, plastic, tissue engineered scaffold, matrix material, tablet, implanted container, powder, oil, resin, wound dressing, bead, microbead, slow release bead, capsule, injectables, intravenous drips, pump device, silicone implants, or any bio-engineered materials.

In one aspect the provided pharmaceutically acceptable carrier is a poloxamer. Poloxamers, referred to by the trade name Pluronics®, are nonionic surfactants that form clear thermoreversible gels in water. Poloxamers are polyethylene oxide-polypropylene oxide-polyethylene oxide (PEO-PPO-PEO) tri-block copolymers. The two polyethylene oxide chains are hydrophilic but the polypropylene chain is hydrophobic. These hydrophobic and hydrophilic characteristics take charge when placed in aqueous solutions. The PEO-PPO-PEO chains take the form of small strands where the hydrophobic centers would come together to form micelles. The micelle, sequentially, tend to have gelling characteristics because they come together in groups to form solids (gels) where water is just slightly present near the hydrophilic ends. When it is chilled, it becomes liquid, but it hardens when warmed. This characteristic makes it useful in pharmaceutical compounding because it can be drawn into a syringe for accurate dose measurement when it is cold. When it warms to body temperature (when applied to skin) it thickens to a perfect consistency (especially when combined with soy lecithin/isopropyl palmitate) to facilitate proper inunction and adhesion. Pluronic® F127 (F127) is widely used because it is obtained easily and thus it is used in such pharmaceutical applications. F127 has a EO:PO:EO ratio of 100:65:100, which by weight has a PEO:PPO ratio of 2:1. Pluronic gel is an aqueous solution and typically contains 20-30% F-127. Thus, the provided compositions can be administered in F127.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Effective dosages and schedules for administering the compositions may be determined empirically, and making such determinations is within the skill in the art. The dosage ranges for the administration of the compositions are those large enough to produce the desired effect in which the symptoms disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual doctor in the event of any counterindications. Dosage can vary, and can be administered in one or more dose administrations daily, for one or several days. Guidance can be found in the literature for appropriate dosages for given classes of pharmaceutical products. The range of dosage largely depends on the application of the compositions herein, severity of condition, and its route of administration.

For example, in applications as a laboratory tool for research, the ACT peptide compositions can be used in doses as low as 0.01% w/v. The dosage can be as low as 0.02% w/v and possibly as high as 2% w/v in topical skin wound treatments. Significantly higher concentrations of the compositions by themselves or in combination with other compounds may be used in applications like cancer/tumor therapy or as an early concentrated bolus immediately following an acute tissue injury. Thus, upper limits of the provided polypeptides may be up to 2-5% w/v or v/v if given as an initial bolus delivered for example directly into a tumor mass. Recommended upper limits of dosage for parenteral routes of administration for example intramuscular, intracerebral, intracardicardiac and intraspinal could be up to 1% w/v or v/v depending on the severity of the injury. This upper dosage limit may vary by formulation, depending for example on how the polypeptide(s) is combined with other agents promoting its action or acting in concert with the polypeptide(s).

For continuous delivery of the provided polypeptides, for example, in combination with an intravenous drip, upper limits of 0.01 g/Kg body weight over time courses determined by the doctor based on improvement in the condition can be used. In another example, upper limits of concentration of the provided nucleic acids delivered topically, for example, in skin wounds would be 5-10 µg/cm$^2$ of wound depending for example on how the nucleic acid is combined with other agents promoting its action or acting in concert with the nucleic acids. This would be repeated at a frequency determined by the Doctor based on improvement. In another example, upper limits of concentration of the provided nucleic acids delivered internally for example, intramuscular, intracerebral, intracardicardiac and intraspinal would be 50-100 µg/ml of solution. Again, the frequency would be determined by the Doctor based on improvement.

Also disclosed is the pre-conditioning of an area with the provided polypeptides prior to surgery. The concentration of the polypeptides can be 10-200 µM mixed in with 10-30% pluronic gel or any such carrier that enables penetration of the peptide(s) within the site of interest for a period of at least 3-6 hours prior to surgery. This pre-procedural conditioning can improve the subsequent healing response to surgery, including reduced inflammatory response.

Viral vectors remain highly experimental tools that nonetheless show considerable potential in clinical applications. As such, caution is warranted in calculation of expected dosage regimes for viral vectors and will depend considerably on the type of vector used. For example, retroviral vectors infect dividing cells such as cancer cells efficiently, intercalating into the host cell genome and continuing expression of encoded proteins indefinitely. Typical dosages of retroviruses in an animal model setting are in the range of $10^7$ to $10^9$ infectious units per ml. By contrast, adenoviruses most efficiently target post-mitotic cells, but cells are quickly eliminated by the host immune system or virus is eventually lost if infected cells resume proliferation and subsequently dilute the viral episomal DNA. Indeed, this transient time course of infection may be useful for short-term delivery of the composition described herein in certain clinical situations, for example in amelioration of a small injury. In animal models, concentrations of $10^8$-$10^{11}$ infectious units per ml of adenovirus are typical for uses in research. Dose ranges of vectors based on data derived from animal models would be envisaged to be used eventually in clinical setting(s), pending the development of pharmaceutically acceptable formulation(s).

Two topical applications of ACT compositions at 0.02% w/v; one applied acutely and the second applied 24 hours later are sufficient to reduce inflammation, promote healing, reduce scarring, increase tensile strength, and promote tissue regeneration. However, in a clinical setting an increased frequency of up to 3 applications per day topically at a concentration of up to 5% is recommended until significant improvement is achieved as determined by a Doctor. For internal administration, for example, intravenously, intramuscularly, intracerebral, intracardicardiac and intraspinally and increased frequency of up to 3 dosages of 1% w/v or v/v per day is recommended until significant improvement is determined by the Doctor.

Following administration of a disclosed composition, such as a polypeptide, for promoting wound healing, the efficacy of the therapeutic composition can be assessed in various ways well known to the skilled practitioner. For instance, one of ordinary skill in the art will understand that a composition, such as a polypeptide, disclosed herein is efficacious in promoting wound healing in a subject by observing that the composition can reduce scar tissue formation, reduce fibrotic tissue formation, improve tissue regeneration, or reduce inflammation in the subject following tissue injury. Methods for measuring these criteria are known in the art and discussed herein.

Also provided are materials comprising the herein provided compositions (e.g., polypeptides, nucleic acids, or vectors). For example, provided are materials used to treat wounds, wherein the materials are coated with an ACT polypeptide. Non-limiting examples of materials used to treat wounds include bandages, steri-strip, sutures, staples, or grafts (e.g., skin grafts).

For example, the material (e.g., bandage, steri-strip, suture, staple, graft) can be soaked in the provided polypeptide at a concentration ranging from 10-200 µM. The material can then be dried and sealed in a sterile container. The material can also be immersed in liquid 10-30% pluronic gel at 4° C. containing polypeptide at 10-200 µM concentration. The material can then be brought to approximate room temperature so that the gel polymerizes, leaving a coat of polypeptide-impregnated gel surrounding the material, which can be sealed in a sterile container. The polypeptide can also be incorporated into a cross-linkable hydrogel system, such as the poly(lactic-co-glycolic acid) (PLGA) or polyurethane, which can then be fashioned into materials for treating wounds (e.g., bandage, steri-strip, suture, staple, graft). Thus, provided are composite hydrogel-peptide materials.

Also disclosed are medical implants coated with the provided polypeptide before implantation in a subject. For example, a common problem in such implant surgeries is the formation of a contraction capsule around the implant from scar tissue formation that leads to undue hardening, contraction and ultimately misshaping of the tissue of interest. The use of the present polypeptides in or on the implant can reduce or prevent this misshaping. Non-limiting examples of medical implants include: limb prostheses, breast implants, penile implants, testicular implants, artificial eyes, facial implants, artificial joints, heart valve prostheses, vascular prostheses, dental prostheses, facial prosthesis, tilted disc valve, caged ball valve, ear prosthesis, nose prosthesis, pacemakers, cochlear implants, and skin substitutes (e.g., porcine heterograft/pigskin, BIOBRANE, cultured keratinocytes).

A. Methods

Provided herein is a method of promoting wound healing following tissue injury in a subject, comprising administering to the subject one or more of the herein provided compositions (e.g., polypeptides, nucleic acids, or vectors) in a pharmaceutically acceptable carrier. Further provided is a method of treating a subject with tissue injury, comprising administering to the subject one or more of the herein provided compositions (e.g., polypeptides, nucleic acids, or vectors) in a pharmaceutically acceptable carrier.

"Promote," "promotion," and "promoting" refer to an increase in an activity, response, condition, disease, or other biological parameter. This can include but is not limited to the initiation of the activity, response, condition, or disease. This may also include, for example, a 10% increase in the activity, response, condition, or disease as compared to the native or control level. Thus, the increase can be a 10, 20, 30, 40, 50, 60, 70, 80, 90, 100%, or any amount of increase in between as compared to native or control levels.

By "treat" or "treatment" is meant a method of reducing the effects of a disease or condition. Treatment can also refer to a method of reducing the underlying cause of the disease or condition itself rather than just the symptoms. The treatment can be any reduction from native levels and can be but is not limited to the complete ablation of the disease, condition, or the symptoms of the disease or condition. For example, a disclosed method for promoting wound healing is considered to be a treatment if there is a 10% reduction in one or more symptoms of the disease in a subject with the disease when compared to native levels in the same subject or control subjects. Thus, the reduction can be a 10, 20, 30, 40, 50, 60, 70, 80, 90, 100%, or any amount of reduction in between as compared to native or control levels.

As used herein, "subject" includes, but is not limited to, animals, plants, bacteria, viruses, parasites and any other organism or entity that has nucleic acid. The subject may be a vertebrate, more specifically a mammal (e.g., a human, horse, pig, rabbit, dog, sheep, goat, non-human primate, cow, cat, guinea pig or rodent), a fish, a bird or a reptile or an amphibian. The subject can be an invertebrate, more specifically an arthropod (e.g., insects and crustaceans). The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

The provided method can reduce scar tissue formation in a subject following tissue injury. By "scar tissue" is meant the fibrous (fibrotic) connective tissue that forms at the site of injury or disease in any tissue of the body, caused by the overproduction of disorganized collagen and other connective tissue proteins, which acts to patch the break in the tissue. Scar tissue may replace injured skin and underlying muscle, damaged heart muscle, or diseased areas of internal organs such as the liver. Dense and thick, it is usually paler than the surrounding tissue because it is poorly supplied with blood, and although it structurally replaces destroyed tissue, it cannot perform the functions of the missing tissue. It is composed of collagenous fibers, which will often restrict normal elasticity in the tissue involved. Scar tissue may therefore limit the range of muscle movement or prevent proper circulation of fluids when affecting the lymphatic or circulatory system. Glial scar tissue following injury to the brain or spinal chord is one of the main obstacles to restoration of neural function following damage to the central nervous system. A reduction in scar tissue can be assessed by the population of cell types within the injured site. For example, a reduction in glial scar tissue can be estimated by an increased ratio of neuronal to astrocytic cells. A reduction in scar tissue formation can be measured by a simple measurement of scar width or area of scar tissue (Wilgus et al., 2003). In addition histological assessments can be made about the restoration of structural complexity within healed tissue in comparison to normal tissue.

In addition to reducing fibrotic tissue formation in a subject in following tissue injury, the provided compositions and methods can also be used to treat disorders associated with pathological increases in fibrotic tissue formation in a subject, such as for example, psoriasis, cutaneous and systemic mastocytosis, asthma, eczema, sinusitis, atherosclerosis, rheumatoid arthritis, inflammatory bowel disease, multiple sclerosis, pulmonary fibrosis and cystic fibrosis. A reduction in fibrotic tissue formation in a subject can be measured by clinical judgment of a doctor assessing whether a regain in normal structure and function of a given tissue and/or organ in a subject has resulted following a treatment. As an example, for psoriasis a doctor would assess the subject's skin to determine whether there has been a reduction in patches of raised red skin covered by flaky white buildup. Certain kinds of psoriasis, are characterized by a pimple-ish (pustular psoriasis) or burned (erythrodermic) appearance. In such cases, the doctor would determine whether treatment has resulted in the reduction of these symptoms. In the case of an tissue or organ in which a subject where a doctor judges that a biopsy is clinically available and/or necessary or in an animal model of the human disease, tissue fragments of biopsies would be prepared and tissue histological structure would be assessed by a clinical pathologist and/or trained histopathologist to determine if reduction in fibrosis and restoration of normal tissue structure and function has occurred. The area of fibrosis to normal tissue could also be quantitatively assessed on such histological preparations.

The provided method can restore normal tissue mechanical properties such as tensile strength following tissue injury in a subject. "Tensile strength" refers to the amount of stress or strain required to break the tissue or wound.

The tensile strength of treated wounds can be 60, 65, 70, 75, 80, 85, 90, 95, 100% that of uninjured tissue within 3 months after treatment. Thus, provided is a method of restoring tissue mechanical properties, including increasing tensile strength of a healed injury to approach or reach that of normal uninjured tissue, in a subject comprising administering to the subject one or more of the herein provided compositions (e.g., polypeptides, nucleic acids, or vectors) in a pharmaceutically acceptable carrier.

The type of wounds that would be important with respect to tensile strength/extensibility would include injuries to musculoskeletal structures/tissues, and the skin covering these structures. For example, the provided methods can improve tensile strength of articulating joints, bone, cartilage, tendons, or ligaments. The provided methods can also improve tensile strength of skin under higher degrees of stress/strain, such as the skin covering the elbow, knee, or foot. The most common problems associated with healing of joint injuries is that excessive scarring in these areas leads to contraction, and non-extensibility of the healed joint area. This has serious cosmetic and psychological consequences. The properties of the peptides will help modulate and lessen the formation of such scar tissue leading to greater mobility of the joint.

The provided method can improve tissue regeneration following tissue injury in a subject. By "regeneration" is meant the renewal, re-growth, or restoration of a body or a bodily part, tissue, or substance after injury or as a normal bodily process. In contrast to scarring, tissue regeneration involves the restoration of the tissue to its original structural, functional, and physiological condition. This is also referred to herein as tissue "complexity". The restoration can be partial or complete, meaning 10, 20, 30, 40, 50, 60, 70, 80, 90, 100% restoration, or any amount of restoration in between as compared to native or control levels. As an example, in the case of a skin injury, tissue regeneration can involve the restoration of hair follicles, glandular structures, blood vessels, muscle, or fat. In the case of a brain injury, tissue regeneration can involve maintenance or restoration of neurons. As an example in the case of skin an improvement in tissue regeneration can be assessed by measurements of the volume of fibrous scar tissue to normal regenerated skin as a ratio. As another example, counts can be made of discrete regenerating structures such as regenerating skin glands normalized to the volume of the wound area.

In one aspect, tissue regeneration involves the recruitment and differentiation of stem cells to replace the damaged cells. As used herein, a "stem cell" is an undifferentiated cell found among differentiated cells in a tissue or organ, or introduced from an external source for e.g., Embryonic stem cells, Adult Bone Marrow stem cells, that can renew itself and differentiate to yield the major specialized cell types of the tissue or organ. The primary roles of stem cells in a living organism are to maintain and repair the tissue in which they are found. By stem cell differentiation is meant the process whereby an unspecialized cell (e.g., stem cell) acquires the features of a specialized cell such as a skin, neural, heart, liver, or muscle cell. As an example, in the case of a skin injury, tissue regeneration can involve the differentiation of stem cells present in the epithelium into hair follicles (Alonso and Fuchs, 2003). In the case of a brain injury, tissue regeneration can involve the differentiation of stem cells into neurons. The provided method can enhance stem cell differentiation following tissue injury in a subject. Enhanced stem cell differentiation can be measured by providing a clinically acceptable genetic or other means of marking endogenous or engrafted stem cells and determining the frequency of differentiation and incorporation of marked stem cells into normal tissue structures. As another example, certain structures such as hair follicles are known to be regenerated from endogenous stem cells following tissue injury. As such, counts of hair follicles normalized to tissue injury area would serve as a quantitative assessment of enhanced stem cell differentiation.

The provided method can reduce inflammation in a subject. By "inflammation", "inflammatory response" or "immune response" is meant the reaction of living tissues to injury, infection or irritation characterized by redness, warmth, swelling, pain, and loss of function, produced as the result of increased blood flow and an influx of immune cells and secretions. Inflammation is the body's reaction to invading infectious microorganisms and results in an increase in blood flow to the affected area, the release of chemicals that draw white blood cells, an increased flow of plasma, and the arrival of monocytes (or astrocytes in the case of the brain) to clean up the debris. Anything that stimulates the inflammatory response is said to be inflammatory. Thus, in addition to reducing inflammation in a subject in response to tissue injury, the provided compositions and methods can also be used to treat disorders associated with pathological increases in levels of inflammatory cells, including, for example, asthma, eczema, sinusitis, atherosclerosis, rheumatoid arthritis, inflammatory bowel disease, cutaneous and systemic mastocytosis, psoriasis, and multiple sclerosis. Treatment with the provided polypeptide can also reduce itching, for example of healing wounds. Generally, itching results from histamine release by mast cells. The provided polypeptide can reduce mast cell de-granulation and histamine release. Thus, the provided polypeptide can be used to treat conditions involving histamine release, including, but not limited to, itching, scratching, sinus irritation, allergic cough, red eyes, asthma, and eczema.

A reduction in inflammation can be measured by a reduction in the density of inflammatory cell types such as, for example, monocytes or astrocytes. A reduction in inflammation can be measured by a reduction in the density of inflammatory cell types such as, for example, neutrophils, mast cells, basophils, and monocytes. A reduction in inflammation can be calculated by an in vivo measurement of neutrophil activity (Jones et al., 1994). In addition factors like frequency of mast cell degranulation or measurement of histamine levels or levels of reactive oxygen species can be used as measurements of reduction in inflammation. The level of inflammation can also be indirectly measured by checking for transcription levels of certain genes by qRT-PCR for e.g. genes like, Interferon-alpha, -beta and -gamma, Tumor Necrosis Factor-alpha, Interleukine 1beta, -2, -4, -5, -6, -8, -12, -18, -23, -27, CD4, CD28, CD80, CD86, MHCII, and iNOS. Measurement of pro-inflammatory cytokine levels in the tissues and or bodily fluids of the subject including plasma can measure a reduction in inflammation. It is noteworthy that a mechanism of ACT peptide action may be by inhibition of inflammatory cell migration and/or inhibition of pro-inflammatory chemicals (histamine, reactive oxygen species) and pro-inflammatory cytokines such as Interleukin (IL)-1, IL-6, IL-8 and tumor necrosis factor (TNF).

Figure 2:
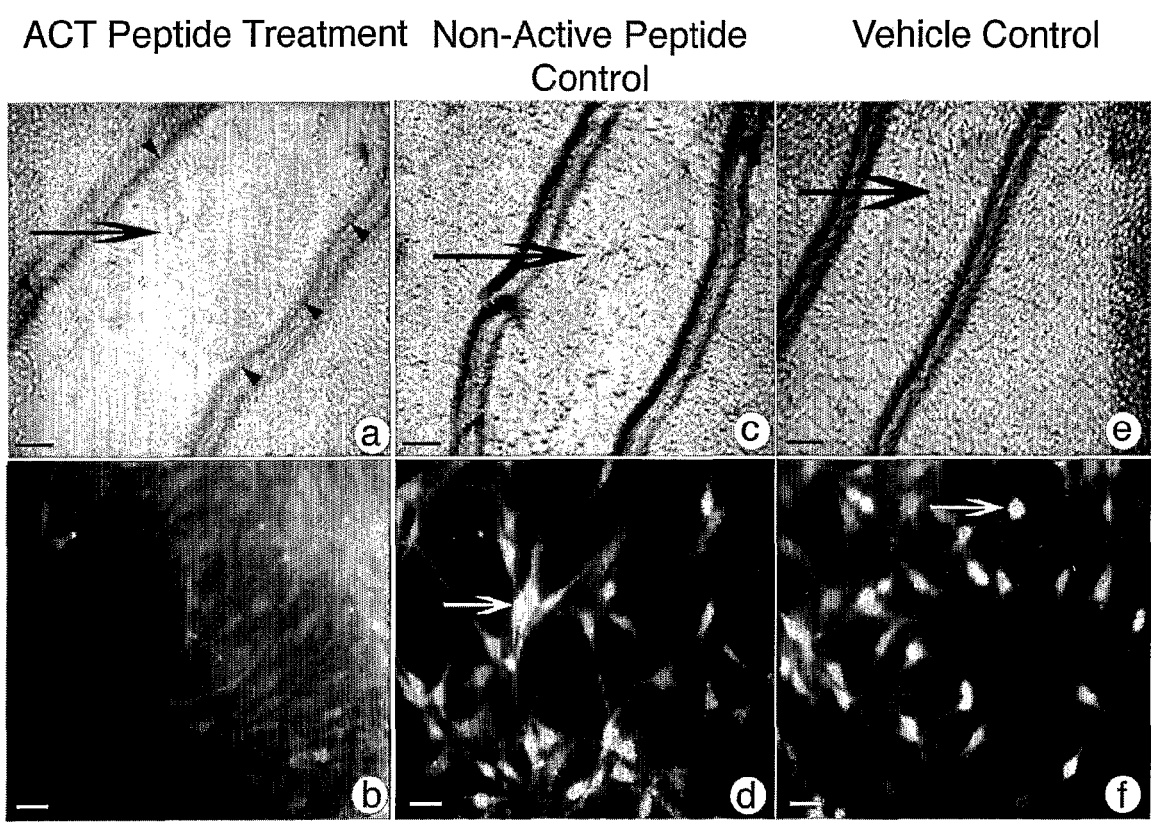
FIG. 2 shows that ACT peptide inhibits proliferation and migration of transformed fibroblasts (NIH-3T3 cells) injured by a scratch. An NIH-3T3 monolayer was pre-treated with ACT 1 peptide (SEQ ID NO:2) for 24 hrs, and "scratch-injured" with a p200 pipette tip. The "scratch injury" was subsequently allowed to "heal" for 24 hours in the presence of (a, b) 30 µM ACT 1 peptide (SEQ ID NO:2), (c, d) 30 µM non-active control peptide (SEQ ID NO: 55), or (e, f) vehicle control solution containing no ACT peptide or control peptide. The "scratch injury" of ACT peptide-treated cells remains relatively unhealed after 24 hours (a), with few cells (large arrow) repopulating the area within the initial "scratch injury" edges (i.e., within area marked by the small black arrowheads). By contrast, in the control conditions in (c) and (e), large numbers of cells (large arrows) have repopulated the area within the initial "scratch injury". The repopulation of the "scratch injury" occurs in part via migration of the transformed cells crawling into the "scratch injury" area. Figures (b), (d) and (f) show proliferating cell nuclear antigen (PCNA) immunolabeling of cells in the "scratch injury" or at the injury edge. ACT peptide treated cells (b) show only low luminosity consistent with background and non-proliferation. Only in the two control conditions shown in (d) and (f), are brightly labeled proliferating cells seen (white arrows). This indicates that the ACT peptide has also reduced proliferation of the transformed cells.

The provided method can inhibit proliferation of a transformed cell in a subject (see FIG. 2). By transformed cell is meant a neoplasm, cancer, or tumor cell that divides and reproduces abnormally with uncontrolled growth. Thus, inhibition of proliferation (i.e., hyperplasia) of said transformed cell results in a reduction in the growth and thus malignancy of the cancer. A representative but non-limiting list of cancers that the disclosed compositions and methods can be used to treat is the following: glioma, lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma, glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers, testicular cancer, colon and rectal cancers, prostatic cancer, or pancreatic cancer. Thus, the provided method can be used to treat cancer in a subject. For example, the provided method can be used to treat glioma in a subject.

An inhibition in transformed cell proliferation can be measured by a variety of cell proliferation markers and kits for e.g. Ki67/MIB-1 immunostaining, tritiated thymidine or bromodeoxyuridine labeling indices, DNA S-phase fraction, proliferating cell nuclear antigen expression, potential doubling time and analysis of the nucleolar organizer region associated proteins (AgNORs). Since the proliferative activity of the tumor depends both on the proportion of cells committed to the cycle (growth fraction) and the speed of the cell cycle, the actual proliferative activity of a tumor could well be measured by the equation [PA=Ki67 or MIB-1 scores×AgNORs] (Pich et al., 2004). In another example, histopathologists are skilled in assessing biopsy tissue sections using simple qualitative and quantitative indices of mitosis to determine proliferation in transformed cell populations Various mouse models have been developed for cancer research. There are specific mouse models for specific types of cancers. For example, Bladder cancer, Cervical cancer, Endometrial cancer, Gastrointestinal cancer, Genitourinary cancer, Head and Neck cancer, Hematopoietic cancer, Kidney cancer, Lung cancer, Mammary Gland cancer, Melanoma, Myeloma, Nervous System cancer, Oral cancer, Ovarian cancer, Pancreatic cancer, Prostate cancer, Sarcoma, Skin cancer. These models are well described and used. The favorable effects of the polypeptides, nucleic acids or vectors provided herein can be studied in any of these models. For example the skin cancer mouse model can be easily used for demonstration. Cancers can be cultivated applying the xenograft model of growing human cancerous tissues using the specific pathogen free, homo inbred mouse (a nude mouse) (Yoo, 2004). The polypeptides, nucleic acids or vectors provided herein can be locally administered for e.g. bioengineered materials such as a hollow fiber membranes (Orlandini and Margaria. 1983; Ming Chu et al., 1998) and microfibers, slow release beads, hypodermic needles, indwelling catheters, which can be inserted locally into the cancerous growth, or systemically administered to reach its target for e.g. intravenous infusions, intramuscularly, intraperitoneal injection. This treatment can be administered by itself or in combination with other therapeutic compounds for e.g. Chemotherapeutic agents.

The provided method can inhibit metastasis of a transformed cell in a subject. By "metastasis" is meant the transmission of cancer cells from an original site to one or more sites elsewhere in the body, usually by way of the blood vessels or lymphatics. Metastatis can be broken down into a series of events. First, cancer cell migration begins the process by which tumor cells leave the primary site of growth, often penetrating the basement membrane and moving towards the local vasculature. Intravasation describes the process of cancer cell entry into the vasculature, and distribution to distant sites. Extravasation refers to the process of cancer cell egression from the vasculature. Finally, proliferation of cancer cells at the distant site is profoundly influenced by localized growth factor availability, influences of stromal cells, and the surrounding extracellular matrix milieu (the so-called "soil") as well as the availability of nutrients and factors provided by the resultant vascularization of the growing tumor. Thus, the provided compositions and methods can inhibit metastasis of a transformed cell in a subject by inhibiting migration (i.e., metastatic migration) of said cell. Tumourigenesis is the result of cell cycle disorganization, leading to an uncontrolled cellular proliferation. Specific cellular processes-mechanisms that control cell cycle progression and checkpoint traversation through the intermitotic phases are deregulated. Normally, these events are highly conserved due to the existence of conservatory mechanisms and molecules such as cell cycle genes and their products. An inhibition in metastatic migration can be measured by the levels of such cell cycle genes and products for e.g. cyclins, cyclin dependent kinases (Cdks), Cdk inhibitors (CKI) and extra cellular factors (i.e. growth factors). Revolutionary techniques using laser cytometry and commercial software are available to quantify and evaluate cell cycle processes and cellular growth. S-phase fraction measurements, including ploidy values, using histograms and estimation of indices such as the mitotic index and tumour-doubling time indices, provide adequate information to the clinician to evaluate tumour aggressiveness.

As used herein, tissue injury can result from, for example, a scrape, cut, laceration wound, crush wound, compression wound, stretch injury, bite wound, graze, bullet wound, explosion injury, body piercing, stab wound, burn wound, wind burn, sun burn, chemical burn, surgical wound, surgical intervention, medical intervention, host rejection following cell, tissue or organ grafting, pharmaceutical effect, pharmaceutical side-effect, bed sore, radiation injury, cosmetic skin wound, internal organ injury, disease process (e.g., asthma, cancer), infection, infectious agent, developmental process, maturational process (e.g., acne), genetic abnormality, developmental abnormality, environmental toxin, allergen, scalp injury, facial injury, jaw injury, foot injury, toe injury, finger injury, bone injury, sex organ injury, joint injury, excretory organ injury, eye injury, corneal injury, muscle injury, adipose tissue injury, lung injury, airway injury, hernia, anus injury, piles, ear injury, retinal injury, skin injury, abdominal injury, arm injury, leg injury, athletic injury, back injury, birth injury, premature birth injury, toxic bite, sting, tendon injury, ligament injury, heart injury, heart valve injury, vascular system injury, cartilage injury, lymphatic system injury, craniocerebral trauma, dislocation, esophageal perforation, fistula, nail injury, foreign body, fracture, frostbite, hand injury, heat stress disorder, laceration, neck injury, self mutilation, shock, traumatic soft tissue injury, spinal cord injury, spinal injury, sprain, strain, tendon injury, ligament injury, cartilage injury, thoracic injury, tooth injury, trauma, nervous system injury, aging, aneurism, stroke, digestive tract injury, infarct, or ischemic injury.

The peptides and/or other formulations embodying the invention will modulate cell migration and proliferation, thereby reducing inflammation, accelerating wound healing, reduce scarring and ultimately promote repair, regeneration and restoration of structure and function in all tissues. Healing of wounds, post-peptide application will involve significantly reduced fibrosis, consequently reduced scarring in skin wounds and fibrous patches in internal tissue injuries, promoting tissue regeneration and restoring tissue and organ structure and function.

An additional embodiment of the invention comprises an in vitro scratch wound assay of cell migration that the peptide alters and modulates migration and proliferation of various cultured cell types, including but not limited to, fibroblasts/mesenchymal cells, tumor cells and epithelial cells.

Further, said peptides and/or formulations embodying the invention can be used to treat external wounds caused by, but not limited to scrapes, cuts, lacerated wounds, bite wounds, bullet wounds, stab wounds, burn wounds, sun burns, chemical burns, surgical wounds, bed sores, radiation injuries, all kinds of acute and chronic wounds, wounds or lesions created by cosmetic skin procedures and also ameliorate the effects of skin aging. The actions of said peptides and/or other formulations will accelerate wound healing in all kinds of external wounds and improve the cosmetic appearance of wounded areas, and skin subject to aging and disease. Said peptides and/or other formulations can be used to treat internal injury caused by, but not limited to, disease, surgery, gunshots, stabbing, accidents, infarcts, ischemic injuries, to organs and tissues including but not limited to heart, bone, brain, spinal cord, retina, peripheral nerves and other tissues and organs commonly subject to acute and chronic injury, disease, congenital and developmental malformation and aging processes. Injury to internal organs causes a fibrotic response, which leads to loss of structure and function in organ systems. In central nervous system (CNS) this response to injury is mediated by astrocytes (fibroblast-like cells in the CNS) and thus will subsequently be referred to as an astrocytic response. Embodiments of our invention will alleviate this fibrotic/astrocytic response hence helping in repair and regeneration of injured tissues and restoration of tissue and organ structure and function.

Further embodiments of the inventions include the use of said peptides and/or other formulations to improve angiogenesis by stimulating angiogenic factors like, but not limited to VEGF, and improve differentiation of vascular tissues thereby improving blood flow to the site of tissue injury.

Increased blood supply to the wound site stimulated by our treatments will result in reduced scarring in external and internal wounds and promote improved repair and regeneration of tissues and organs.

Additional embodiments of the invention comprises the use of said peptides and/or other formulations for tissue and organ regeneration, when administered in association with stem cells and/or drugs and/or other endogenous and/or clinical regimens promoting stem cell mobilization and/or tissue regeneration. Stem cells will help in tissue regeneration and our treatment will promote differentiation directly and/or indirectly by processes that include, but are not limited to reduced fibrotic/astrocytic scar formation, thereby restoring normal tissue structure and function. Our treatment will promote the generation of a permissive environment in vivo for regeneration and restoration of structure and function of tissues and organs. Regenerative processes aided by our peptide include, but are not limited to internal and external injury, regeneration of tissues, organs, or other body parts, healing and restoration of function following vascular occlusion and ischemia, brain stroke, myocardial infarction, spinal cord damage, brain damage, peripheral nerve damage, retinal damage, bone damage and other insults to tissues causing destruction, damage or otherwise resulting from, but not limited to, injury, surgery, cancer, congenital and developmental malformation, and diseases causing progressive loss of tissue structure and function, including but not limited to diabetes, bacterial, viral and prion-associated diseases, Alzheimer's disease, Parkinson's disease, AIDs and other genetically determined, environmentally determined or idiopathic disease processes causing loss of tissue/organ/body part structure and function. In addition, we claim that our peptide can be administered with drugs or other compounds promoting tissue and cellular regeneration including, but not limited to, trophic factors in processes including, but not limited to, brain, retina, spinal cord and peripheral nervous system regeneration (e.g., NGFs, FGFs, Neurtrophins, Neuregulins, Endothelins, GDNFs, BDNF. BMPs, TGFs, Wnts).

Said peptides and/or other formulations can be used in bioengineering approaches to tissue and organ repair, regeneration and restoration of structure and function, including but not limited to, application with bioengineered delivery vehicles. These include but are not limited to, nanoparticles, fibers, gels, polymers, polyethylene glycol and other bioengineered materials designed for the purpose of promoting tissue repair and/or targeted and/or sustained release of our peptide and tissue scaffolds, polymer matrices and other bioengineered surfaces or structures coated or otherwise treated to release, maintain or localize the effects of said peptides and/or other formulations in association with the other beneficial effects or otherwise of these bioengineered materials.

Additional embodiments of the invention comprise the use of said peptides and/or other formulations in vitro and/or in animal models humanized or otherwise to promote and/or assist in the regeneration of tissues, organs and body parts for use, but not limited to organ/tissue or body part transplantation.

A further embodiment of the invention comprises the use of said peptides and/or other formulations to alleviate the symptoms of Multiple Sclerosis (MS). MS is a chronic disease of the central nervous system. Pathologically, MS is characterized by the presence of areas of demyelination and T-cell predominant perivascular inflammation in the brain white matter. The anti-inflammatory and regenerative properties of our treatment will help in the treatment of MS and other conditions similar to it. Said peptide will help with conditions like, but not limited to psoriasis, scleroderma, acne, eczema and other diseases of skin and connective tissues. Psoriasis, a chronic, inflammatory skin disease characterized by an uncontrolled shedding of the skin and afflicts millions of people throughout the world. The effects of our treatment on fibroblasts and inflammatory response of the treatments, as stated in the claims above, will help alleviate Psoriasis. Eczema is characterized by painful swelling, oozing of the skin, bleeding cracks, severe scaling, itching and burning. As stated above, the effects of our treatment on fibroblasts and inflammatory response, combined with accelerated healing properties will relieve symptoms of eczema.

Said peptides and/or other formulations will help with repair after cosmetic and/or clinical procedures involving, but not limited to, controlled damage—e.g., corneal laser surgery, laser and dermabrasion/dermaplaning, skin resurfacing, and punch excision. Application of our treatment immediately after surgery or any cosmetic procedure will reduce or eliminate scarring. Uses of said peptides and/or other formulations will reduce keloid scar formation. Keloid scars are common in dark skin people of Asian, African, or Middle Eastern descent. Keloid scar is a thick, puckered, itchy cluster of scar tissue that grows beyond the edges of a wound or incision. Keloid scars are sometimes very nodular in nature, and they are often darker in color than surrounding skin. They occur when the body continues to produce tough, fibrous protein (known as collagen) after a wound has healed. Application of our treatment will ameliorate formation of these Keloid scars.

Additional uses of said peptides and/or other formulations will help correct other diseases and other conditions (e.g., congenital and developmental defects, aging) associated with inflammatory response, fibrosis and connective tissue disorders. Fibrosis is a common condition noted after trauma to any bodily organ or tissue. Excessive fibrosis results in loss of structure and function and scarring at the trauma site. Our treatment will reduce fibrosis and promote regeneration, and restoration of structure and function.

Said peptides and/or other formulations will modulate cell proliferation and can be used alone or in association with drugs used in the treatment of uncontrolled proliferation (e.g., anti-cancer drugs) and procedures (e.g., radiation therapy). Diseases of uncontrolled cell proliferation, or hyperplasias, are common health problems. Examples of diseases of cell over-proliferation include but are not limited to psoriasis, seborrhea, scleroderma, eczema, benign prostate hyperplasia, congenital adrenal hyperplasia, endometrial hyperplasia, squamous cell (vulvular) hyperplasia, sebaceous hyperplasia, Crohn's Disease, leukemia, carcinoma, lymphoma. Our peptides limits undesirable cellular proliferation and will thus improve prognosis of conditions associated with excessive cell proliferation.

Said peptides and/or other formulations will have effects on cell migration, proliferation and differentiation and thus will assist in preventing metastasis. Said peptides and/or other formulations can be administered alone or in association with drugs or procedures used in the treatment of metastasis like but not limited to, Altretamine, Asparaginase, Bleomycin, Busulfan, Carboplatin, Carmustine, Chlorambucil, Cisplatin, Cladribine, Cyclophosphamide, Cytarabine, Dacarbazine, Diethylstilbesterol, Ethinyl estradiol, Etoposide, Floxuridine, Fludarabine, Fluorouracil, Flutamide, Goserelin, Hydroxyurea, Idarubicin, Ifosfamide, Leuprolide, Levamisole, Lomustine, Mechlorethamine, Medroxyprogesterone, Megestrol, Melphalan, Mercaptopurine, Methotrexate, Mitomycin, Mitotane, Mitoxantrone, Paclitaxel, pentastatin, Pipobroman, Plicamycin, Prednisone, Procarbazine, Streptozocin, Tamoxifen, Teniposide, Vinblastine, Vincristine. Metastasis is the spread of cancer from its primary site to other places in the body. Cell migration is the movement of cells from one part of the body to another. Our treatments effects on cell migration demonstrates its ability to inhibit spread of tumors.

Additional embodiments of the invention comprise the delivery of said peptides and/or other formulations using techniques such as, but not limited to, all Antennapedia sequences, and related cell internalization vectors (e.g., TAT protein transduction domain, all TAT peptides, all TAT fusion proteins), viral gene delivery vectors, DNA expression vectors, and any other delivery method that can help get our peptide to the tissue and/or cellular site of action by itself or in association with other agents including but not limited to co-factors assisting this delivery (e.g., including but limited to TAT-HA2) and/or stem cells, drugs and other formulations which help in repair, regeneration and restoration of organ and tissue structure and function.

B. Methods of Making the Compositions

The compositions disclosed herein and the compositions necessary to perform the disclosed methods can be made using any method known to those of skill in the art for that particular reagent or compound unless otherwise specifically noted.

For example, the provided nucleic acids can be made using standard chemical synthesis methods or can be produced using enzymatic methods or any other known method. Such methods can range from standard enzymatic digestion followed by nucleotide fragment isolation (see for example, Sambrook et al., *Molecular Cloning: A Laboratory Manual*, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., *Ann. Rev. Biochem.* 53:323-356 (1984), (phosphotriester and phosphite-triester methods), and Narang et al., *Methods Enzymol.*, 65:610-620 (1980), (phosphotriester method). Protein nucleic acid molecules can be made using known methods such as those described by Nielsen et al., *Bioconjug. Chem.* 5:3-7 (1994).

One method of producing the disclosed polypeptides, such as SEQ ID NO:2, is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form a protein, or fragment thereof. (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide—thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol.

Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

Disclosed are processes for making the compositions as well as the intermediates leading to the compositions. There are a variety of methods that can be used for making these compositions, such as synthetic chemical methods and standard molecular biology methods. It is understood that the methods of making these and the other disclosed compositions are specifically disclosed. Disclosed are nucleic acid molecules produced by the process comprising linking in an operative way a nucleic acid encoding a polypeptide disclosed herein and a sequence controlling the expression of the nucleic acid. Disclosed are cells produced by the process of transforming the cell with any of the herein disclosed nucleic acids. Disclosed are any of the disclosed peptides produced by the process of expressing any of the herein disclosed nucleic acids. Disclosed are animals produced by the process of transfecting a cell within the animal with any of the nucleic acid molecules disclosed herein. Disclosed are animals produced by the process of transfecting a cell within the animal any of the nucleic acid molecules disclosed herein, wherein the animal is a mammal. Also disclosed are animals produced by the process of transfecting a cell within the animal any of the nucleic acid molecules disclosed herein, wherein the mammal is mouse, rat, rabbit, cow, sheep, pig, or primate. Also disclose are animals produced by the process of adding to the animal any of the cells disclosed herein.

C. Kits

The materials described above as well as other materials can be packaged together in any suitable combination as a kit useful for performing, or aiding in the performance of, the disclosed method. It is useful if the kit components in a given kit are designed and adapted for use together in the disclosed method. For example disclosed are kits for promoting wound healing, the kit comprising one or more of the polypeptides, nucleic acids or vectors provided herein in a pharmaceutically acceptable carrier. Such kits can also include gels, bandages, Millipore tapes, Medicated Q-tips, Sprays, props, Syrups, Liquids, Disposable tubes or pouches. The kits also can contain instructions for proper use and safety information of the product or formulation. The kits may contain dosage information based on the application and method of administration as determined by a doctor.

D. Uses

The disclosed methods and compositions are applicable to numerous areas including, but not limited to, laboratory research tools. These formulations play regulatory roles in several cellular processes for e.g. Cell Proliferation, Cell Migration. These formulations can be used in the laboratory in both in vitro and in vivo model systems for studying various cellular processes, cell cycle regulations, cell behavior, responses of cells, organs or tissues to test compounds etc. The formulations can be supplied by themselves or in combination with other compounds or as part of a kit, such as a kit for cell proliferation assay. The kit may contain the formulations mentioned herein by themselves or in combination with other compounds. Such a kit would include instructions designed to facilitate the experiment. Other uses are disclosed, apparent from the disclosure, and/or will be understood by those in the art.

EXAMPLES

Example 1

In Vitro Scratch Injury

Myocytes from neonatal rat hearts were grown until forming a near-confluent monolayer on a tissue culture dish according to standard protocols. The cultures were subsequently allowed to culture for a further 5 days culture medium comprising 30 µM ACT 1 peptide (SEQ ID NO:2), 30 µM non-active control peptide (SEQ ID NO:55), or phosphate buffered saline (PBS) containing no ACT peptide or control peptide. The non-active control peptide comprises a polypeptide with a carboxy terminus in which the ACT peptide sequence has been reversed. The amino terminus of ACT and control peptides are both biotinylated, enabling detection (i.e., assay) of the peptides in the cell cytoplasm using standard microscopic or biochemical methods based on high affinity streptavidin binding to biotin.

Figure 1:
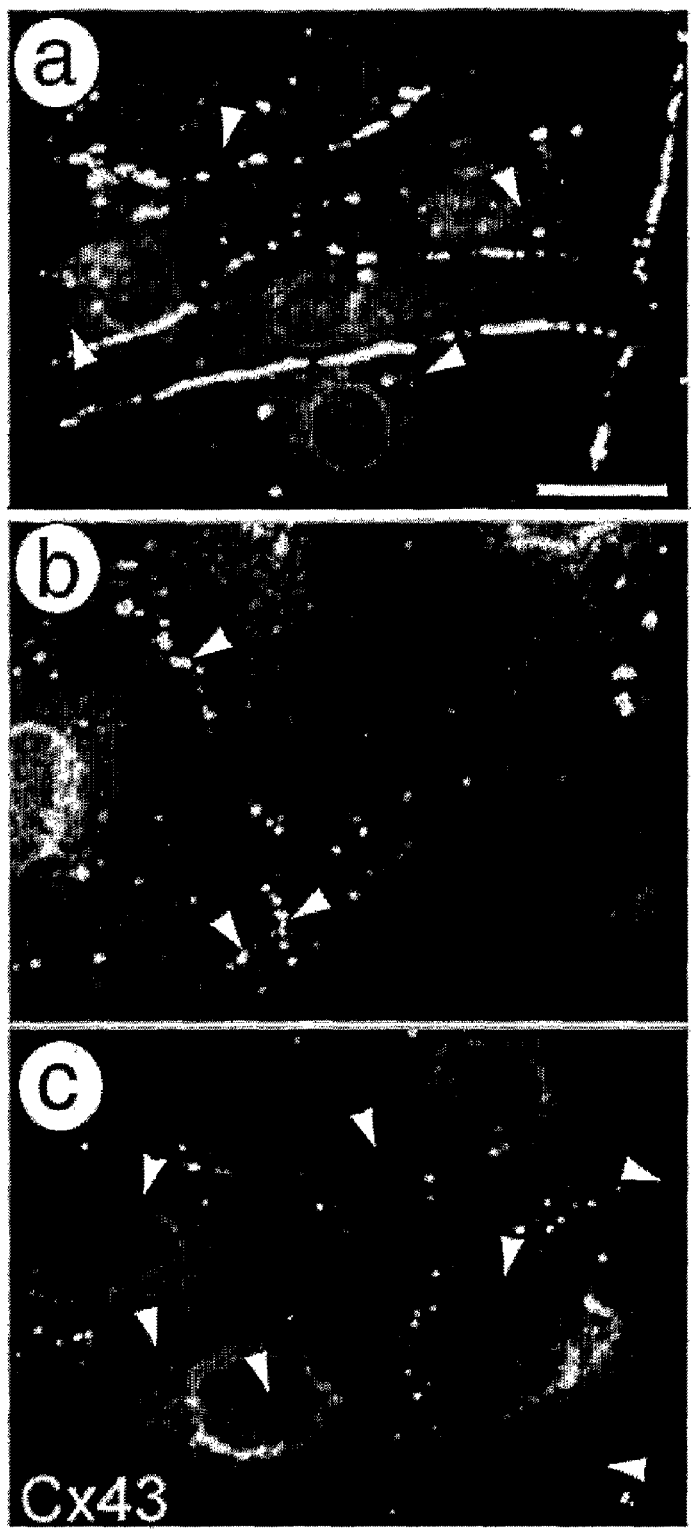
FIG. 1 shows that an alpha Connexin carboxy-Terminal (ACT) polypeptide increases the extent of Cx43 gap junction formation in cultured neonatal myocytes. Myocytes from neonatal rat hearts were grown until forming a near-confluent monolayer on a tissue culture dish according to standard protocols. The cultures were subsequently allowed to culture for a further 5 days in culture medium comprising (a) 30 µM ACT 1 peptide (SEQ ID NO:2), (b) 30 µM non-active control peptide (SEQ ID NO:55), or (c) phosphate buffered saline (PBS) containing no ACT peptide or control. Culture media with added peptides or vehicle control was changed every 24 hours during the experiment. (a) indicates that ACT peptide greatly increased the extent of Cx43 gap junction formation (dots and lines indicated by arrowheads) between myocytes relative to the control conditions (b) and (c). This increase in Cx43 gap junction formation in response to ACT peptide is shared by a number of cell types expressing Cx43.

Culture media with added peptides or vehicle control was changed every 24 hours during the experiment. FIG. 1a indicates that ACT peptide greatly increased the extent of Cx43 gap junction formation between myocytes relative to the control conditions (FIGS. 1b and 1c). As shown in FIG. 4, this increase in Cx43 gap junction formation in response to ACT peptide is shared by a number of cell types expressing CX43.

NIH-3T3 cells were grown over 2-3 days until forming a near-confluent monolayer on a tissue culture dish according to standard protocols and the monolayer was then pre-treated with ACT 1 peptide (SEQ ID NO:2) for 24 hrs, and "scratch-injured" with a p200 pipette tip. The "scratch injury" was subsequently allowed to repopulate for 24 hours in the presence of 30 µM ACT 1 peptide (SEQ ID NO:2) dissolved in the culture media (FIGS. 2a, b) or in presence of two control conditions (FIG. 2c-f). In the first control condition, the "scratch-injured" cells were allowed to repopulate for 24 hours in the presence of a non-active control peptide (as in FIG. 1) dissolved in the culture media at a concentration of 30 µM (FIGS. 2c, d). In the second control condition, phosphate buffered saline (PBS) was added to the culture media and the "scratch-injured" cells were allowed to repopulate in the presence of this vehicle control solution containing no ACT peptide or control peptide (FIGS. 2e, f). The "scratch injury" of ACT peptide-treated cells remains relatively repopulated after 24 hours (FIG. 2a), with few cells (large arrow) repopulating the area within the initial "scratch injury" edges (i.e., within area marked by the small black arrowheads). By contrast, in the control conditions in (FIGS. 2c, e), large numbers of cells (large arrows) have repopulated the area within the initial "scratch injury". The repopulation of the "scratch injury" occurs in part via migration of the transformed cells crawling into the "scratch injury" area. Figures (FIGS. 2b, d, and f) show proliferating cell nuclear antigen (PCNA) immunolabeling of cells in the "scatch injury" or at the injury edge. ACT peptide treated cells (FIG. 2b) show only low luminosity consistent with background and non-proliferation. Only in the two control conditions shown in figures (FIGS. 2d, f), are brightly labeled proliferating cells seen (white arrows). This indicates that the ACT peptide has also reduced proliferation of the transformed cells in this experimental cellular model.

Figure 3:
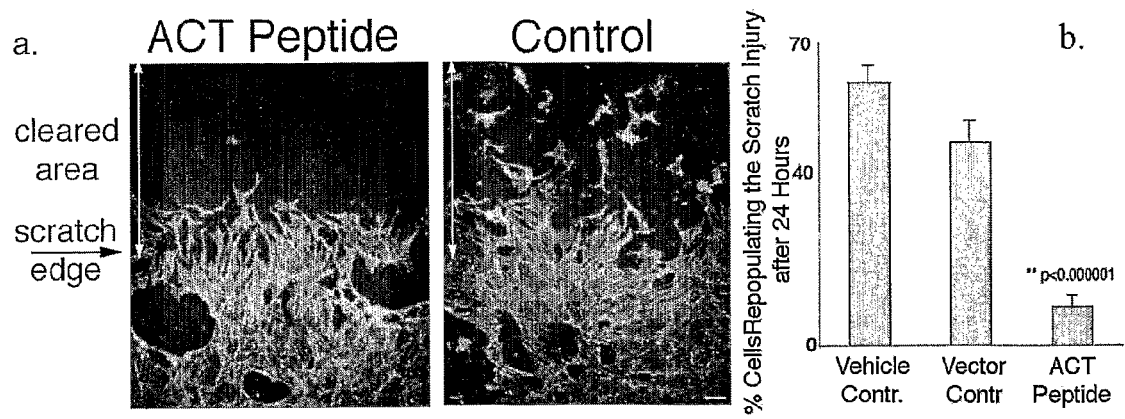
FIG. 3 shows quantification of the inhibition of migration by ACT peptides following injury in an experimental cellular model. NIH-3T3 fibroblasts were "scratch injured" and subject to the continuous presence of 30 µM ACT 1 peptide (SEQ ID NO:2) for 24 hours or the control conditions as outlined in FIG. 2. Figure (a) shows the injury edge of ACT peptide and non-active peptide-treated control cells at the end of the 24-hour period. The cells have been labeled with fluorescent phalloidin to aid visualization. ACT peptide-treated cells show low levels of repopulation of the scratch injury area (white double headed arrows). Figure (b) shows a bar graph of the % area of cells repopulating the scratch injury after 24 hours. The reduction of cells in the injury area in the presence of ACT peptide is dramatic, with a $p<0.000001$.

FIG. 3a shows the injury edge of ACT peptide and non-active peptide-treated control cells at the end of the 24-hour period. The cells were labeled with fluorescent phalloidin to aid visualization. ACT peptide-treated cells show low levels of repopulation of the scratch injury area (white double headed arrows). FIG. 3b shows a bar graph of the % area of cells repopulating the scratch injury after 24 hours. The reduction of cells in the injury area in the presence of ACT peptide is dramatic, with a p value of less than 0.000001.

WB-F344 cells are a transformed rat epithelial cell line derived by treatment of isolated rat liver cells with a cancer-causing agent (Tsao et al., 1984; Hayashi et al., 1997; Hayashi et al., 1998; Hayashi et al., 2001). WB-F344 cells were transfected with a cDNA expression plasmid construct and selected under antibiotic using standard protocols to generate cell lines that stably expressed an ACT-peptide-encoding-polynucleotide (SEQ ID NO:6) operably linked to a promoter sequence or a green fluorescent protein (GFP) polynucleotide operably linked to a promoter sequence as a control. The polynucleotide encoding the ACT peptide also encoded GFP. As such, expression of the ACT peptide could be assayed by standard GFP fluorescence optics on a light microscope. FIGS. 4a, b show high magnification images of GFP fluorescence in WB-F344 cell lines expressing GFP alone (FIG. 4a) or GFP plus the carboxy terminus ACT peptide sequence (FIG. 4a) or GFP alone (FIG. 4b). Near confluent monolayers of the WB-F344 cell lines were "scratch injured" and allowed to repopulate for 24 hours. Similar to the control cases of the NIH-3T3 cells treated with vehicle or non-active control peptide, the control epithelial cell line expressing GFP repopulated the scratch injury (FIG. 4c). However, in the epithelial cell line that stably expressed the ACT-peptide-encoding-polynucleotide operably linked to a promoter sequence, there was inhibited repopulation of the scratch injury (FIG. 4d). In addition to WB-F344 cells lines, NIH-3T3 cell lines have been made that stably express an ACT-peptide-encoding-polynucleotide operably linked to a promoter Example 2

In Vivo Wound Healing

Neonatal mouse pups were desensitized using hypothermia. A 4 mm long incisional skin injury was made using a scalpel through the entire thickness of the skin (down to the level of the underlying muscle) in the dorsal mid line between the shoulder blades. 30 µl of a solution of 20% pluronic (F-127) gel containing either no (control) or dissolved ACT 1 peptide (SEQ ID NO:2) at a concentration of 60 µM was then applied to the incisional injuries. Pluronic gel has mild surfactant properties that may aid in the uniform dispersion of the ACT peptide in micelles. More importantly, 20% pluronic gel stays liquid at temperatures below 15° C., but polymerizes at body temperature (37° C.). This property of pluronic gel probably aided in the controlled release of peptide into the tissue at the site of incisional injury, protecting the peptide from break-down in the protease-rich environment of the wound and also enabling active concentrations of the peptide to maintained over prolonged periods. Control or ACT peptide containing gel was applied subsequently 24 hours after the initial application. No further application of control and ACT peptide containing gel was made after the second application. By 48 hours it can be noted that the ACT peptide treated injury (FIG. 5a) is significantly more closed, less inflamed, less swollen (note ridges at the wound edge), and generally more healed in appearance than the control injury that received no ACT peptide (FIG. 5b). These differences in inflammation, swelling and healing between the control and ACT peptide and control treated injury persisted at the 72 (FIGS. 5c, d) and 96 (FIGS. 5e, f) hour time points. At 7 days, the ACT peptide wound (FIG. 5g), had a smoother and less scarred appearance than the control peptide-treated injury (FIG. 5h). Note that images of the same injury on the same animal are shown at the different time points during the healing time course.

Anesthetized adult mice had 8 mm wide circular excisional skin injuries made by fine surgical scissors down to the underlying muscle in the dorsal mid line between the shoulder blades (FIGS. 6a, b). The boundary of the injury was demarcated by an 8 mm wide circular template cut in a plastic sheet. 100 µl of a solution of 30% pluronic gel containing either no (control) or dissolved ACT 1 peptide (SEQ ID NO:2) at a concentration of 100 µM was then applied to the excisional injuries. Control or ACT peptide containing gel was applied subsequently 24 hours after the initial application. No further applications of control and ACT peptide containing gel were made after the second application. The ACT peptide-treated large excisional injury (FIGS. 6a, c, e, g, i) closed faster, was less inflamed in appearance, healed faster and scarred less than the control injury that received no ACT peptide (FIGS. 6b, d, f, h, j) over the 14 day time course. Indeed, the control injury at 14 days still shows a partial scab indicating that acute healing of the injury was incomplete (FIG. 6j).

Skin biopsies of the entire wound site were taken from some of the 24 hours following the excisional injury. These skin samples were fixed in 2% paraformaldehyde, paraffin-embedded, sectioned and Hemotoxylin and Eosin (H&E) histochemically stained using standard protocols. FIGS. 7a and 7b show low magnification survey views of cross-sections from near the center of the wound of ACT peptide and control treated injuries, respectively. The wound edge (marked by the small arrows), bounded by skin of normal histological appearance, can be seen in both cases. A black rectangle is placed over the images in FIGS. 7a and 7b at the left hand wound edge. The histological structures within the black rectangle placed over the left hand wound edges in FIGS. 7a and 7b are shown at higher magnification in FIGS. 7c and 7d for ACT peptide and control treated tissues, respectively. Of interest is a "collar-like" tissue of aligned fibrous material (arrowed) projecting from basal parts of the injury to or toward the wound edge and exterior surface of injury. Fibrous material serves as a substrate for migration of inflammatory cells moving to the injury surface (Elder et al., 1997). Interestingly, the aligned fibrous substrate has the appearance of being much more organized in the control injury (FIG. 7d) than in the ACT peptide treated injury (FIG. 7c). Also, there is a considerably lower density of inflammatory cells studding the fibrous substrate in the ACT peptide-treated tissue. This is confirmed in (FIG. 7f) and (FIG. 7e) where regions of histological section within the black rectangles shown in (FIG. 7d) and (FIG. 7c) are respectively shown at higher magnification. The inflammatory cells studding the aligned fibrous substrate include mast cells, neutrophils and macrophages. These inflammatory cells occur at much higher density in the control injury than in the ACT peptide treated injury.

At the end of the 14 day period, skin biopsies of the entire excisional injury were taken and histological sections from these skin samples were H&E histochemically stained. FIGS. 8a and 8b show low magnification survey views of cross-sections from near the center of the injury of ACT peptide and control, respectively. The wound edge (marked by the small arrows), bounded by skin of normal histological appearance, can be seen in both cases. A black rectangle is placed over the images in FIGS. 8a and 8b near the center of each injury. The histological structures within these two rectangles are shown at higher magnification in FIGS. 8c and 8d for the ACT peptide and control tissues, respectively. It is evident that tissue within the ACT peptide treated injury locus has considerably more complexity. At the external surface of the ACT treated wound, there is a continuous layer of epithelial cells indicating that re-epithelization of the injured surface is complete, albeit that the epithelium is as yet relatively thin near the center of the wound (FIG. 8c). Unusually, regenerating hair follicles can already be seen differentiating de novo from stem cells in the new epithelium covering the healed injury (FIG. 8c, small arrows). By comparison, re-epithelization of the injury surface is incomplete and there is no sign of regenerating hair follicles in the epithelium of the control injury. Beneath the reformed epithelium of the ACT peptide treated injured skin, considerable restoration of normal structural complexity is seen, with glandular structures, fibrous and connective tissues, vascular tissues, muscle and fat cells all in evidence (FIGS. 8a, c). As with the hair follicles, this tissue complexity was regenerated by differentiation of stem cells. By contrast, in the control injury the wound tissue is completely dominated by a uniform and large plug of fibrous scar tissue (FIGS. 8b, d), with other complexity of tissue structure not particularly in evidence within this scar tissue.

Anesthetized adult mice had 2 small (5 mm diameter) excisional skin wounds made by fine surgical scissors on the neck and (upper) back. The boundaries of the injuries were demarcated by a 5 mm wide circular template cut in a plastic sheet. 50-60 µl of a solution of 30% pluronic gel containing either no (control) or one of the ACT peptides (ACT 2—SEQ ID NO:1, ACT 1—SEQ ID NO:2, ACT 3—SEQ ID NO:3, ACT 4—SEQ ID NO:4, ACT 5—SEQ ID NO:5) dissolved at concentrations of 100 µM were then applied to the excisional injuries. Control or ACT peptide-containing gels were applied subsequently 24 hours after the initial application. No further applications of control and ACT peptide-containing gel were made after the second application. It can be noted in the case of ACT 1 (FIG. 9e-h), ACT 2 (FIG. 9i-l), ACT 3 (FIG. 9m-p), and ACT 5 (FIG. 9u-x) peptides that excisional injuries closed faster, were less inflamed in appearance, healed faster and scarred less than the control injury that received no ACT peptide (FIG. 9a-d) over the 240 hour time course (10 days). The ACT 4 peptide (FIG. 9q-t) also appeared to show modest improvement in healing over the control during the time course. Note that the same wound on the same animal is shown at the different time points during the healing time course.

The area of open wound was measured during the time course using NIH image according to standard protocols on multiple (~5 mice per control or treatment condition) adult mice. These individual area measurements were then normalized to (i.e., divided by) the average area measured for the control injuries for a given time point, multiplied by 100 to give a % of unclosed wound relative to the control and then plotted against time. A Mann-Whitney U-test was used to statistically assess the effects of ACT peptides over the time course. ACT 1, ACT 2, ACT 3, and ACT 5 peptides significantly improved wound closure rates following excisional injury. These treatments provided results with significant p values. The ACT 1 and ACT 3 quantifiably gave the most pronounced improvements over the control. A more modest, although consistent, improvement was also observed for the ACT 4 peptide over the control.

Anesthetized adult rats were positioned in a stereotaxic apparatus. A midline incision was made on the scalp to expose the skull. A stereotaxic drill was sighted 2 mm posterior to the bregma and 2 holes were drilled with a 1 mm spherical bit, each at 2.5 mm to the right and left of the bregma, and 3.5 mm below the dura. A cerebral lesion was made by inserting an 18-gauge needle. The coordinates were determined from the atlas by Paxinos and Watson (1986). The hollow fiber membrane (HFM) was inserted in the hole and external skin sutures were placed to cover the stab. The ACT peptide was dissolved at 100 µM concentration in a 2% collagen vehicle solution contained within the HFM. Studies of isolated HFMs indicated that these bioengineered constructs were capable of slow release of detectable levels of ACT peptide (as assayed by biotin-streptavidin reaction) in aqueous solutions for periods of at least 7 days. Reactive astrocytosis associated with inflammation and subsequently with glial scar formation follows a well characterized time course after brain injury in rodent models (Norenberg, 1994; Fawcett and Asher, 1999). Typically, the astrocytic response in rat brain peaks after a week, together with loss of neurons and other aspects of brain tissue complexity. Subsequently with the emergence of glial scar tissue, the density of GFAP-positive astrocytes decreases. FIGS. 10b and 10c show low magnification survey views of sections of brain tissue (cortex) surrounding HFM implants filled with ACT peptide plus vehicle gel or control collagen vehicle gel or ACT peptide plus vehicle gel a week following brain penetration injury. In the control tissue (FIG. 10c), a high density of immunolabeled GFAP-positive astrocytes is observed near the site of injury caused by the HFM. The density of these cells appears to diminish slightly distal from the injury. By contrast, a much lower density of GFAP-positive astrocytes is observed adjacent the HFM filled with ACT peptide (FIG. 10b). Indeed, the levels of GFAP positive cells are not dissimilar to those seen in normal uninjured brain tissue. The regions of tissue within the white rectangles in FIGS. 10b and 10c are shown at higher magnification in FIGS. 10d and 10e, respectively. In the brain injury treated by ACT peptide (FIG. 10d), it can be seen that GFAP-positive astrocytes are not only less numerous, but are also smaller than those seen in the control injury (FIG. 10e).

FIGS. 11a and 11b show low magnification survey views of sections of brain tissue (cortex) surrounding HFM implants (implant or injury border is shown by arrows) filled with control collagen vehicle gel (FIG. 11b) or ACT peptide plus vehicle gel (FIG. 11a) at 1 week following brain penetration injury. In the control tissue (FIG. 11b), a high density of immunolabeled GFAP-positive astrocytes and low density of NeuN immunolabeled neurons are observed near the site of injury caused by the HFM. The density of these cells appears to diminish and increase distal from the HFM, respectively. By contrast, a much lower density of GFAP-positive astrocytes and higher numbers NeuN immunolabeled neurons are observed proximal (as well as distal) to the HFM filled with ACT peptide ((FIG. 11a). The areas in FIGS. 11a and 11b proximal to the HFMs are shown at high magnification views of in FIGS. 11c and 11d, respectively. Again, in the control tissue (FIG. 1d) a striking increase in the density of GFAP-positive astrocytes and a reduced density of NeuN-positive neurons is observed compared to ACT peptide treated tissue seen (FIG. 11c). A complementary pattern is observed near the HFM containing ACT peptide, with NeuN positive neurons predominating over astrocytes (FIG. 11c). Interestingly, the high magnification view shown in FIG. 11d reveals a high frequency of neurons in the process of fission relative to the control (FIG. 11c). This suggests that the high density of neurons associated with ACT peptide treatment may be from generation of new neurons. ACT peptide can also increase neuronal density in part by sparing neurons from cell death following brain injury.

Example 3

Treatment of Acute Spinal Cord Injury

Subjects with acute spinal cord injuries represent a seriously problematic group for whom even a small neurological recovery of function can have a major influence on their subsequent independence. In one example, a subject with acute spinal cord injury receives a bolus infusion of a 0.02% to 0.1% solution of ACT peptide (e.g., SEQ ID NO:1) over 15 min within 8 h directly into the site of acute spinal cord injury, followed 45 min later by an infusion of 0.01% solution of ACT peptide for a subsequent 23 to 48 hours. In another example, ACT peptide is used to coat slow release nanoparticles loaded within 8 h directly into the site of acute spinal cord injury or tissue engineered bioscaffolds designed to promote neural reconnection across the zone of acute spinal cord lesion. Improvement in function are assessed by a doctor at intervals (e.g., 6, 12, 26 and 52 weeks) following treatment by neurological outcome tests including assessments designed to measure motor activity, pinprick skin sensitivity and recovery of sensation.

Example 4

Quantitative Assessment of Wound Closure, Tissue Regeneration, and Tensile Strength of Excisional Skin Wounds ACT peptide (n=12) and control (n=8) 5 mm-diameter excisional skin wounds were generated on adult mice as described above. Quantitative assessments of wound closure rate, counts of regenerated hair follicles and tensile strength measurements were then undertaken on the wounded skin at time points up to 90 days following the initial insult. Relative to control wounds, closure was significantly enhanced within 24 hours of peptide treatment. Similarly, at 10 days, when most wounds were nearing completion of closure, a highly significant difference was still maintained such that ACT peptide-treated wounds were on average 43% smaller than control wounds. At 10 days ACT peptide wounds showed a significant 3.2 fold increase in the number of regenerated hair follicles per unit area of the healed wound over control wounds.

Studies were undertaken of the mechanical properties of healed 5 mm diameter excisional wounds at 1 month and 3 months following injury. For mechanical property measurements, the skin samples were obtained after sacrificing the animal and evaluated using a MTS 858 Mini Bionix (MTS Systems Corporation, MN, USA) equipped with a 5 kg load cell. During measurement the skin sample was extended to break at a rate of 0.5 mm/s. Force and extension was measured at break. The tensile strength (stress) and extension to break (strain) was calculated as follows, Stress ($N/mm^2$)=Force at break (N)/cross-sectional area of sample ($mm^2$). Strain (%)= [Increase in length at break (mm)/Original length (mm)]× 100. Stress and strain calculations for each wounded skin sample was normalized to a normal skin sample from a nearby area collected from the same animal.

At 1 month, the stress (i.e., normalized force) required to break wounded skin was similar to that of control wounded skin. At 3 months, normalized stress to break of peptide-treated wound skin was on average double that of control wounded skin, although the high variance within the treatment group precluded significant mean separation from the control. This result demonstrates that the intrinsic tensile strength of peptide-treated wounds was as good or better than that of untreated wounds. Further, significant improvements in extensibility of peptide-treated wounds were found. The amount of strain (i.e., extensibility) required to break peptide-treated wounds was modestly improved over control wounds at 1 month. At 3 months, peptide-treated wounds showed a more striking improvement, increasing to a near normal 90% of unwounded skin. By contrast, control wounds at 3 months remained only 60% as extensible as normal skin.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a polypeptide" includes a plurality of such polypeptides, reference to "the polypeptide" is a reference to one or more polypeptides and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps.

Those skilled in the art will recognize, or be able to ascertain using no more than routine experimentation, many equivalents to the specific embodiments of the method and compositions described herein. Such equivalents are intended to be encompassed by the following claims.

E. References

Alonso L, Fuchs E. Stem cells of the skin epithelium. Proc Natl Acad Sci USA. 2003 Sep. 30; 100 Suppl 1:11830-5, 2003

Barker R J, Price R L, Gourdie R G. Increased association of ZO-1 with Connexin43 during remodeling of cardiac gap junctions. Circ Res. February 22; 90(3):317-24 (2002).

Bucci, M. et al. In vivo delivery of the caveolin-1 scaffolding domain inhibits nitric oxide synthesis and reduces inflammation. Nat. Med. 6, 1362-1367 (2000).

Chien K R. Stem cells: lost in translation. Nature. April 8; 428(6983):607-608 (2004).

Derossi, D., Joliot, A. H., Chassaing, G. & Prochiantz, A. The third helix of Antennapedia homeodomain translocates through biological membranes. J. Biol. 679-686 (2000).

Elmquist, A., Lindgren, M., Bartfai, T. & Langel, U. VE-cadherin-derived cell-penetrating peptide, pVEC, with carrier functions. Exp. Cell Res. 269, 237-244 (2001).

Elder D., Elenitsas R, Jawaorsky C, & Johnson B. Lever's histopathology of the skin. Lippincott-Raven Publishers, (1997).

Fawcett J W, Asher R A. The glial scar and central nervous system repair. Brain Res. Bull. 49:377-391 (1999).

Fischer, P. M. et al. Structure-activity relationship of truncated and substituted analogues of the intracellular delivery vector Penetratin. J. Pept. Res. 55, 163-172 (2000).

Frankel, A. D. & Pabo, C. O. Cellular uptake of the Tat protein from human immunodeficiency virus. Cell 55, 1189-1193 (1988).

Fu C T, Bechberger J F, Ozog M A, Perbal B, Naus C C. CCN3 (NOV) interacts with Connexin43 in C6 glioma cells: possible mechanism of Connexin-mediated growth suppression. J Biol. Chem. August 27; 279(35):36943-50 (2004).

Gao, C. et al. A cell-penetrating peptide from a novel pVII-pIX phage-displayed random peptide library. Bioorg. Med. Chem. 10, 4057-4065 (2002).

Giepmans B N. Gap junctions and Connexin-interacting proteins. Cardiovasc Res. May 1; 62(2):233-45 (2004).

Goodenough D A, Paul D L. Beyond the gap: functions of unpaired connexon channels. Nat Rev Mol Cell Biol. April; 4(4):285-94 (2003).

Green, M. & Loewenstein, P. M. Autonomous functional domains of chemically synthesized human immunodeficiency virus tat trans-activator protein. Cell 55, 1179-1188 (1988).

Hayashi T, Matesic D F, Nomata K, Kang K S, Chang C C, Trosko J E. Stimulation of cell proliferation and inhibition of gap junctional intercellular communication by linoleic acid. Cancer Lett. 112:103-111 (1997).

Hayashi T, Nomata K, Chang C C, Ruch R J, Trosko J E. Cooperative effects of v-myc and c-Ha-ras oncogenes on gap junctional intercellular communication and tumorigenicity in rat liver epithelial cells. Cancer Lett. 128:145-154 (1998).

Hayashi T, Trosko J E, Hamada K. Inhibition of gap junctional intercellular communication in rat liver epithelial cells with transforming RNA. FEBS Lett. 491:200-206 (2001).

Hong, F. D. & Clayman, G. L. Isolation of a peptide for targeted drug delivery into human head and neck solid tumors. Cancer Res. 60, 6551-6556 (2000).

Kajstura J, Rota M, Whang B, Cascapera S, Hosoda T, Bearzi C, Nurzynska D, Kasahara H, Zias E, Bonafe M, Nadal-Ginard B, Torella D, Nascimbene A, Quaini F, Urbanek K, Leri A, Anversa P. Bone marrow cells differentiate in cardiac cell lineages after infarction independently of cell fusion. Circ Res. January 7; 96(1):127-37 (2005).

Lin, Y. Z., Yao, S. Y., Veach, R. A., Torgerson, T. R. & Hawiger, J. Inhibition of nuclear translocation of transcription factor NF-κB by a synthetic peptide containing a cell membrane-permeable motif and nuclear localization sequence. J. Biol. Chem. 270, 14255-14258 (1995).

Lundberg, P. et al. Cell membrane translocation of the N-terminal (1-28) part of the prion protein. Biochem. Biophys. Res. Commun. 299, 85-90 (2002).

Matsushita M, Noguchi H, Lu Y F, Tomizawa K, Michiue H, Li S T, Hirose K, Bonner-Weir S, Matsui H. Photo-acceleration of protein release from endosome in the protein transduction system. FEBS Lett. 13; 572(1-3):221-6. (2004).

Morris, M. C., Depollier, J., Mery, J., Heitz, F. & Divita, G. A peptide carrier for the delivery of biologically active proteins into mammalian cells. Nature Biotechnol. 19, 1173-1176 (2001).

Norenberg M D. Astrocyte responses to CNS injury. J. Neuropathol. Exp. Neurol. 53:213-220 (1994).

Oehlke, J. et al. Cellular uptake of an α-helical amphipathic model peptide with the potential to deliver polar compounds into the cell interior non-endocytically. Biochim. Biophys. Acta. 1414, 127-139 (1998).

Park, C. B., Yi, K. S., Matsuzaki, K., Kim, M. S. & Kim, S. C. Structure-activity analysis of buforin II, a histone H2A-derived antimicrobial peptide: the proline hinge is responsible for the cell-penetrating ability of buforin II. Proc. Natl. Acad. Sci. USA 97, 8245-8250 (2000).

Paxinos G, Watson C. The Rat Brain in Stereotaxic Coordinates. 2nd ed. San Diego, Calif.: Academic; 1986.

Pich A, Chiusa L, Navone R. Prognostic relevance of cell proliferation in head and neck tumors Annals of Oncology 2004 15(9):1319-1329.

Pooga, M., Hallbrink, M., Zorko, M. & Langel, U. Cell penetration by transportan. FASEB J. 12, 67-77 (1998).

Poss K D, Wilson L G, Keating M T. Heart regeneration in zebrafish. Science. December 13; 298(5601):2188-90 (2002).

Rousselle, C. et al. New advances in the transport of doxorubicin through the blood-brain barrier by a peptide vector-mediated strategy. Mol. Pharmacol. 57(4):679-86 (2000).

Sawada, M., Hayes, P. & Matsuyama, S. Cytoprotective membrane-permeable peptides designed from the Bax-binding domain of Ku70. Nature Cell Biol. 5, 352-357 (2003).

Silver J, Miller J H. Regeneration beyond the glial scar. Nat Rev Neurosci. February; 5(2):146-56 (2004).

Songyang, Z. et al. Recognition of unique carboxyl-terminal motifs by distinct PDZ domains. Science 275, 73-77 (1997).

Tsao M S, Smith J D, Nelson K G, Grisham J W. A diploid epithelial cell line from normal adult rat liver with phenotypic properties of 'oval' cells. Exp. Cell Res. 154:38-52 (1984).

Vigneron, J. P. et al. Guanidinium-cholesterol cationic lipids: Efficient vectors for the transfection of eukaryotic cells. Proc. Natl. Acad. Sci. USA. 93, 9682-9686 (1998).

Wadia J S, Stan R V, Dowdy S F. Transducible TAT-HA fusogenic peptide enhances escape of TAT-fusion proteins after lipid raft macropinocytosis. Nat. Med. 10(3):310-5. (2004).

Ming Y. W. Chu[a], Milton H. Lipsky[a], Lorrin K. Yee[a,c], John Epstein[a], Katharine A. Whartenby[a], Scott Freeman[e], Tian M. Chen[a], Edward Chu[c,d], Edwin N. Forman[b], Paul Calabresi[a] Predictive Sensitivity of Human Cancer Cells in vivo Using Semipermeable Polysulfone Fibers *Pharmacology* 1998; 56:318-326

Orlandini G C, Margaria R. Evaluation of the efficiency of a new hollow fiber plasmapheresis filter. Int J Artif Organs. 1983 July; 6 Suppl 1:103-6.

Wilgus T A, Vodovotz Y, Vittadini E, Clubbs E A, Oberysztn T M. Reduction of scar formation in full-thickness wounds with topical celecoxib treatment. Wound Rep Reg 2003; 11:25-34.

Yoo D S. The dielectric properties of cancerous tissues in a nude mouse xenograft model. Bioelectromagnetics. 2004 October; 25(7):492-7.

Sequences

SEQ ID NO:1 (ACT2)
PSSRASSRASSRPRPDDLEI

SEQ ID NO:2 (ACT 1)
RPRPDDLEI

SEQ ID NO:3 (ACT 3)
RPRPDDLEV

SEQ ID NO:4 (ACT 4)
RPRPDDVPV

SEQ ID NO:5 (ACT 5)
KARSDDLSV

SEQ ID NO:6
aga cct cgg cct gat gac ctg gag att

SEQ ID NO:7 (Antp)
RQPKIWFPNRRKPWKK

SEQ ID NO:8 (Antp/ ACT 2)
RQPKIWFPNRRKPWKKPSSRASSRASSRPRPDDLEI

SEQ ID NO:9 (Antp/ ACT 1)
RQPKIWFPNRRKPWKKRPRPDDLEI

SEQ ID NO:10 (Antp/ ACT 3)
RQPKIWFPNRRKPWKKRPRPDDLEV

SEQ ID NO:11 (Antp/ACT4)
RQPKIWFPNRRKPWKKRPRPDDVPV

SEQ ID NO:12 (Antp/ ACT 5)
RQPKIWFPNRRKPWKKKARSDDLSV

SEQ ID NO:13 (encodes polypeptide of SEQ ID NO 9)
cgg cag ccc aag atc tgg ttc ccc aac cgg cgg aag ccc tgg aag aag cgg ccc ggc ccg acg acc tgg aga tc SEQ ID NO:14 (HIV-Tat)
GRKKRRQRPPQ SEQ ID NO:15 (Penetratin)
RQIKIWFQNRRMKWKK -continued Sequences SEQ ID NO:16 (Antp-3A)
RQIAIWFQNRRMKWAA SEQ ID NO:17 (Tat)
RKKRRQRRR SEQ ID NO:18 (Buforin II)
TRSSRAGLQFPVGRVHRLLRK SEQ ID NO:19 (Transportan)
GWTLNSAGYLLGKINKALAALAKKIL SEQ ID NO:20 (model amphipathic peptide)
KLALKLALKALKAALKLA

SEQ ID NO:21 (K-FGF)
AAVALLPAVLLALLAP

SEQ ID NO:22 (Ku70)
VPMLK-PMLKE

SEQ ID NO:23 (Prion)
MANLGYWLLALFVTMWTDVGLCKKRPKP

SEQ ID NO:24 (pVEC)
LLIILRRRIRKQAHAHSK

SEQ ID NO:25 (Pep-1)
KETWWETWWTEWSQPKKKRKV

SEQ ID NO:26 (SynB1)
RGGRLSYSRRRFSTSTGR

SEQ ID NO:27 (Pep-7)
SDLWEMMMVSLACQY

SEQ ID NO:28 (HN-1)
TSPLNIHNGQKL

SEQ ID NO:29 (Chick alpha Cx43 ACT)
PSRASSRASSRPRPDDLEI

SEQ ID NO:30 (Human alpha Cx45)
GSNKSTASSKSPDPKNSVWI

SEQ ID NO:31 (Chick alpha Cx45)
GSNKSSASSKSGDGKNSVWI

SEQ ID: 32 (Human alpha Cx46)
GRASKASRASSGRARPEDLAI

SEQ ID: 33 (Human alpha Cx46.6)
GSASSRDGKTVWI

SEQ ID NO:34 (Chimp alpha Cx36)
PRVSVPNFGRTQSSDSAYV

SEQ ID NO:35 (Chick alpha Cx36)
PRMSMPNFGRTQSSDSAYV

SEQ ID NO:36 (Human alpha Cx47)
PRAGSEKGSASSRDGKTTVWI

SEQ ID NO:37 (Human alpha Cx40)
GYHSDKRRLSKASSKARSDDLSV

SEQ ID NO:38 (Human alpha Cx50)
PLSRLSKASSRARSDDLTV

SEQ ID NO:39 (Human alpha Cx59)
PNHVVSLTNNLIGRRVPTDLQI

SEQ ID NO:40 (Rat alpha Cx33)
PSCVSSSAVLTTICSSDQVVPVGLSSFYM

-continued

Sequences

SEQ ID NO:41 (Sheep alpha Cx44)
GRSSKASKSSGGRARAADLAI

SEQ ID NO:42 (Human beta Cx26)
LCYLLIRYCSGKSKKPV

SEQ ID: 43 (Human alpha Cx37)
G QK PP SRP SSSAS K KQ*YV

SEQ ID 44: (conservative Cx43 variant)
SSRASSRASSRPRPDDLEV

SEQ ID 45: (conservative Cx43 variant)
RPKPDDLEI,

SEQ ID 46: (conservative Cx43 variant)
SSRASSRASSRPKPDDLEI,

SEQ ID 47: (conservative Cx43 variant)
RPKPDDLDI

SEQ ID 48: (conservative Cx43 variant)
SSRASSRASSRPRPDDLDI

SEQ ID 49: (conservative Cx43 variant)
SSRASTRASSRPRPDDLEI

SEQ ID 50: (conservative Cx43 variant)
RPRPEDLEI

SEQ ID 51: (conservative Cx43 variant)
SSRASSRASSRPRPEDLEI,

SEQ ID 52: (conservative Cx45 variant)
GDGKNSVWV

SEQ ID 53: (conservative Cx45 variant)
SKAGSNKSTASSKSGDGKNSVWV

SEQ ID 54: (conservative Cx37 variant)
GQKPPSRPSSSASKKLYV

SEQ ID NO: 55 (non-active control peptide)
RQPKIWFPNRRKPWKIELDDPRPR

SEQ ID NO:56 (HIV-Tat/ ACT 1)
GRKKRRQRPPQ RPRPDDLEI

SEQ ID NO:57 (Penetratin/ ACT 1)
RQIKIWFQNRRMKWKK RPRPDDLEI

SEQ ID NO:58 (Antp-3A/ ACT 1)
RQIAIWFQNRRMKWAA RPRPDDLEI

SEQ ID NO:59 (Tat/ ACT 1)
RKKRRQRRR RPRPDDLEI

SEQ ID NO:60 (Buforin II/ ACT 1)
TRSSRAGLQFPVGRVHRLLRK RPRPDDLEI

SEQ ID NO:61 (Transportan/ ACT 1)
GWTLNSAGYLLGKINKALAALAKKIL RPRPDDLEI

SEQ ID NO:62 (MAP/ ACT 1)
KLALKLALKALKAALKLA RPRPDDLEI

SEQ ID NO:63 (K-FGF/ ACT 1)
AAVALLPAVLLALLAP RPRPDDLEI

SEQ ID NO:64 (Ku70/ ACT 1)
VPMLKPMLKE RPRPDDLEI

SEQ ID NO:65 (Prion/ ACT 1)
MANLGYWLLALFVTMWTDVGLCKKRPKP RPRPDDLEI

SEQ ID NO:66 (pVEC/ ACT 1)
LLIILRRRIRKQAHAHSK RPRPDDLEI

SEQ ID NO:67 (Pep-1/ ACT 1)
KETWWETWWTEWSQPKKKRKV RPRPDDLEI

SEQ ID NO:68 (SynB1/ ACT 1)
RGGRLSYSRRRFSTSTGR RPRPDDLEI

SEQ ID NO:69 (Pep-7/ ACT 1)
SDLWEMMMVSLACQY RPRPDDLEI

SEQ ID NO:70 (HN-1/ ACT 1)
TSPLNIHNGQKL RPRPDDLEI

SEQ ID NO:72 (20 to 120 residues flanking amino
acid 363 of human Cx43)
KGKSDPYHATSGALSPAKDCGSQKYAYFNGCSSPTAPLSPMSPPGYKLVT

GDRNNSSCRNYNKQASEQNWANYSAEQNRMGQAGSTISNSHAQPFDFPDD

NQNSKKLAAGHELQPLAIVD

SEQ ID NO:73 (20 to 120 residues flanking amino
acid 362 of chick Cx43)
KTDPYSHSGTMSPSKDCGSPKYAYYNGCSSPTAPLSPMSPPGYKLVTGDR

NNSSCRNYNKQASEQNWANYSAEQNRMGQAGSTISNSHAQPFDFADEHQN

TKKLASGHELQPLTIVDQRP

SEQ ID NO:74 (20 to 120 residues flanking amino
acid 377 of human Cx45)
LGFGTIRDSLNSKRRELEDPGAYNYPFTWNTPSAPPGYNIAVKPDQIQYT

ELSNAKIAYKQNKANTAQEQQYGSHEENLPADLEALQREIRMAQERLDLA

VQAYSHQNNPHGPREKKAKV

SEQ ID NO:75 (20 to 120 residues flanking amino
acid 375 of chick Cx45)
GFGTIRDTLNNKRKELEDSGTYNYPFTWNTPSAPPGYNIAVKPDQMQYTE

LSNAKMAYKQNKANIAQEQQYGSNEENIPADLENLQREIKVAQERLDMAI

QAYNNQNNPGSSSREKKSKA.

SEQ ID NO:76 (20 to 120 residues flanking amino
acid 313 of human Cx37)
PYLVDCFVSRPTEKTIFIIFMLVVGLISLVLNLLELVHLLCRCLSRGMRA

RQGQDAPPTQGTSSDPYTDQVFFYLPVGQGPSSPPCPTYNGLSSSEQNWA

NLTTEERLASSRPPLFLDPP

SEQ ID NO:77 (20 to 120 residues flanking amino
acid 258 of rat Cx33)
CGSKEHGNRKMRGRLLLTYMASIFFKSVFEVAFLLIQWYLYGFTLSAVYI

CEQSPCPHRVDCFLSRPTEKTIFILFMLVVSMVSFVLNVIELFYVLFKAI

KNHLGNEKEEVYCNPVELQK.

SEQ ID NO:78 (enhanced green fluorescent protein)
MVSKGEELFTGVVPILVELDGDVNGHKFSVSGEGEGDATYGKLTLKFICT

TGKLPVPWPTLVTTLTYGVQCFSRYPDHMKQHDFFKSAMPEGYVQERTIF

FKDDGNYKTRAEVKFEGDTLVNRIELKGIDFKEDGNILGHKLEYNYNSHN

VYIMADKQKNGIKVNFKIRHNIEDGSVQLADHYQQNTPIGDGPVLLPDNH

YLSTQSALSKDPNEKRDHMVLLEFVTAAGITLGMDELYK

-continued

Sequences

SEQ ID NO:79 (ACT 2)
CCCTCCTCCCGGGCCTCCTCCCGGGCCTCCTCCCGGCCCCGGCCCGAC G
ACCTGGAGATC

SEQ ID NO:80 (ACT 1)
CGGCCCCGGCCCGACGACCTGGAGATC

SEQ ID NO:81 (ACT 3)
CGGCCCCGGCCCGACGACCTGGAGGTG

SEQ ID NO:82 (ACT 4)
CGGCCCCGGCCCGACGACGTGCCCGTG

SEQ ID NO:83 (ACT 5)
AAGGCCCGGTCCGACGACCTGTCCGTG

SEQ ID NO:84 (Antp)
CGGCAGCCCAAGATCTGGTTCCCCAACCGGCGGAAGCCCTGGAAG AAG

SEQ ID NO:85 (Antp/ ACT 2)
CGGCAGCCCAAGATCTGGTTCCCCAACCGGCGGAAGCCCTGGAAGAAGCC
CTCCTCCCGGGCCTCCTCCCGGCCTCCTCCCGGCCCCGGCCCGACGACC
TGGAGATC SEQ ID NO:86 (Antp/ ACT 1)
CGGCAGCCCAAGATCTGGTTCCCCAACCGGCGGAAGCCCTGGAAGAAGCG
GCCCCGGCCCGACGACCTGGAGATC SEQ ID NO:87 (Antp/ ACT 3)
CGGCAGCCCAAGATCTGGTTCCCCAACCGGCGGAAGCCCTGGAAGAAGCG
GCCCCGGCCCGACGACCTGGAGGTG SEQ ID NO:88 (Antp/ ACT 4)
CGGCAGCCCAAGATCTGGTTCCCCAACCGGCGGAAGCCCTGGAAGAAGCG
GCCCCGGCCCGACGACGTGCCCGTG SEQ ID NO:89 (Antp/ ACT 5)
CGGCAGCCCAAGATCTGGTTCCCCAACCGGCGGAAGCCCTGGAAGAAGAA
GGCCCGGTCCGACGACCTGTCCGTG SEQ ID NO:90 (Zebrafish alpha Cx43)
PCSRASSRMSSRARPDDLDV SEQ ID NO:91 (Chick alpha Cx36)
PRVSVPNFGRTQSSDSAYV

---

We claim:

1. A composition comprising at least one polypeptide consisting of the carboxy-terminal most 4 to 30 contiguous amino acids of an alpha connexin protein or conservative variant thereof, wherein said at least one alpha connexin polypeptide is linked at its amino terminus to a cellular internalization transporter.

2. The composition of claim 1, wherein the cellular internalization transporter is an antennapedia sequence.

3. The composition of claim 2, wherein the antennapedia sequence is penetratin or Antp-3A.

4. The composition of claim 2, wherein the antennapedia sequence is SEQ ID NO: 7.

5. The composition of claim 1, wherein the alpha connexin protein is Connexin 37, Connexin 40, Connexin 43, or Connexin 45.

6. The composition of claim 1, wherein the at least one polypeptide consists of the carboxy-terminal most 5 to 19 contiguous amino acids of an alpha connexin protein.

7. The composition of claim 1, wherein the alpha connexin polypeptide consists of the carboxy-terminal most 9 contiguous amino acids of an alpha connexin protein.

8. The composition of claim 1, wherein the alpha connexin polypeptide has a sequence selected from the group consisting of SEQ ID NO: 1, SEQ ID NO: 2, SEQ ID NO: 3, SEQ ID NO: 4, SEQ ID NO: 5, and SEQ ID NO: 43.

9. The composition of claim 1, wherein the alpha connexin polypeptide consists of the carboxy-terminal most 8 contiguous amino acids of of an alpha connexin protein.

10. The composition of claim 1, wherein the alpha connexin polypeptide consists of the carboxy-terminal most 5 contiguous amino acids of an alpha connexin protein.

11. A composition formulated for topical administration comprising a polypeptide consisting of a contiguous sequence of amino acids from the carboxyl terminus of an alpha connexin protein or a conservative variant thereof, wherein said carboxyl terminus includes the sequence up to a transmembrane domain.

12. The composition of claim 11, wherein the alpha connexin polypeptide consists of between 4 and 30 contiguous carboxy-terminal most amino acids of an alpha connexin protein.

13. The composition of claim 11, wherein the alpha connexin protein is Connexin 37, Connexin 40, Connexin 43, or Connexin 45.

14. The composition of claim 11, wherein the alpha connexin polypeptide has a sequence selected from the group consisting of SEQ ID NO: 1, SEQ ID NO: 2, SEQ ID NO: 3, SEQ ID NO: 4, SEQ ID NO: 5, and SEQ ID NO: 43.

15. The composition of claim 14, wherein the alpha connexin polypeptide is linked at its amino terminus to a cellular internalization transporter.

16. The composition of claim 15, wherein the cellular internalization transporter is an antennapedia sequence.

17. The composition of claim 16, wherein the antennapedia sequence is penetratin or Antp-3A.

18. The composition of claim 16, wherein the antennapedia sequence is SEQ ID NO: 7.

19. The composition of claim 15, wherein the alpha connexin polypeptide and the cellular internalization transporter together contain the sequence of SEQ ID NO: 9.

20. The composition of claim 14, wherein the alpha connexin polypeptide has 2 to 5 conservative substitutions as compared to a polypeptide having the sequence of SEQ ID NO: 2.

21. The composition of claim 11, wherein said formulation for topical administration is an ointment, lotion, spray, cream, or gel.

22. The composition of claim 21, wherein said gel is a pluronic gel.

23. The composition of claim 21, wherein said formulation is a poloxamer.

24. The composition of claim 11 further comprising a collagen polymer.

25. The composition of claim 11 further comprising an antibiotic, steroid, analgesic, anti-inflammatory agent, antihistaminic agent, chemotherapy agent, or other therapeutic peptide, or combination thereof.

26. The composition of claim 11, wherein said composition comprises between 0.01% w/v or v/v and 2-5% w/v or v/v alpha connexin peptide.

27. The composition of claim 11, wherein said composition comprises between 10 and 200 μM alpha connexin peptide.

28. A composition comprising a wound-treating material coated with a polypeptide consisting of a contiguous sequence of amino acids from the carboxyl terminus of an alpha connexin protein, wherein said carboxyl terminus includes the sequence up to a transmembrane domain.

29. The wound-treating material of claim 28, wherein the polypeptide consists of the carboxy terminal most 4 to 30 contiguous amino acids of the alpha connexin protein.

30. The wound-treating material of claim 28, wherein the material is selected from the group consisting of a bandage, steri-strip, suture, staple, and graft.

31. The wound-treating material of claim 28, wherein the material is a medical implant.

32. The wound-treating material of claim 28, wherein the material is a bio-engineered material.

33. The wound-treating material of claim 28, wherein the material is a tissue engineered scaffold.

34. A method of promoting healing following tissue injury in a subject, comprising administering to the subject a composition of claim 1, claim 11 or claim 28.

* * * * *

SEQUENCE LISTING

<160> NUMBER OF SEQ IDS NOS: 90

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 1

Pro Ser Ser Arg Ala Ser Ser Arg Ala Ser Ser Arg Pro Arg Pro Asp
1               5                   10                  15

Asp Leu Glu Ile
            20

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 2

Arg Pro Arg Pro Asp Asp Leu Glu Ile
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequences; note =
      synthetic construct

```
<400> SEQUENCE: 3

Arg Pro Arg Pro Asp Asp Leu Glu Val
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 4

Arg Pro Arg Pro Asp Asp Val Pro Val
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 5

Lys Ala Arg Ser Asp Asp Leu Ser Val
1               5

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 6
agacctcggc ctgatgacct ggagatt                                           27

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 7

Arg Gln Pro Lys Ile Trp Phe Pro Asn Arg Arg Lys Pro Trp Lys Lys
1               5                   10                  15

<210> SEQ ID NO 8
<211> LENGTH: 36
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 8

Arg Gln Pro Lys Ile Trp Phe Pro Asn Arg Arg Lys Pro Trp Lys Lys
1               5                   10                  15

Pro Ser Ser Arg Ala Ser Ser Arg Ala Ser Ser Arg Pro Arg Pro Asp
                20                  25                  30

Asp Leu Glu Ile
            35
```

```
<210> SEQ ID NO 9
<211> LENGTH: 25
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 9

Arg Gln Pro Lys Ile Trp Phe Pro Asn Arg Arg Lys Pro Trp Lys Lys
1               5                   10                  15

Arg Pro Arg Pro Asp Asp Leu Glu Ile
            20                  25

<210> SEQ ID NO 10
<211> LENGTH: 25
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 10

Arg Gln Pro Lys Ile Trp Phe Pro Asn Arg Arg Lys Pro Trp Lys Lys
1               5                   10                  15

Arg Pro Arg Pro Asp Asp Leu Glu Val
            20                  25

<210> SEQ ID NO 11
<211> LENGTH: 25
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 11

Arg Gln Pro Lys Ile Trp Phe Pro Asn Arg Arg Lys Pro Trp Lys Lys
1               5                   10                  15

Arg Pro Arg Pro Asp Asp Val Pro Val
            20                  25

<210> SEQ ID NO 12
<211> LENGTH: 25
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 12

Arg Gln Pro Lys Ile Trp Phe Pro Asn Arg Arg Lys Pro Trp Lys Lys
1               5                   10                  15

Lys Ala Arg Ser Asp Asp Leu Ser Val
            20                  25

<210> SEQ ID NO 13
<211> LENGTH: 74
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 13
```

```
cggcagccca agatctggtt ccccaaccgg cggaagccct ggaagaagcg gcccggcccg    60
acgacctgga gatc                                                     74
```

```
<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 14
```

```
Gly Arg Lys Lys Arg Arg Gln Arg Pro Pro Gln
1               5                   10
```

```
<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 15
```

```
Arg Gln Ile Lys Ile Trp Phe Gln Asn Arg Arg Met Lys Trp Lys Lys
1               5                   10                  15
```

```
<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 16
```

```
Arg Gln Ile Ala Ile Trp Phe Gln Asn Arg Arg Met Lys Trp Ala Ala
1               5                   10                  15
```

```
<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 17
```

```
Arg Lys Lys Arg Arg Gln Arg Arg Arg
1               5
```

```
<210> SEQ ID NO 18
<211> LENGTH: 21
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 18
```

```
Thr Arg Ser Ser Arg Ala Gly Leu Gln Phe Pro Val Gly Arg Val His
1               5                   10                  15

Arg Leu Leu Arg Lys
            20
```

```
<210> SEQ ID NO 19
<211> LENGTH: 26
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 19

Gly Trp Thr Leu Asn Ser Ala Gly Tyr Leu Leu Gly Lys Ile Asn Lys
1               5                   10                  15

Ala Leu Ala Ala Leu Ala Lys Lys Ile Leu
            20                  25

<210> SEQ ID NO 20
<211> LENGTH: 18
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 20

Lys Leu Ala Leu Lys Leu Ala Leu Lys Ala Leu Lys Ala Ala Leu Lys
1               5                   10                  15

Leu Ala

<210> SEQ ID NO 21
<211> LENGTH: 16
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 21

Ala Ala Val Ala Leu Leu Pro Ala Val Leu Leu Ala Leu Leu Ala Pro
1               5                   10                  15

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 22

Val Pro Met Leu Lys Pro Met Leu Lys Glu
1               5                   10

<210> SEQ ID NO 23
<211> LENGTH: 28
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 23

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 24
```

```
<211> LENGTH: 18
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 24

Leu Leu Ile Ile Leu Arg Arg Arg Ile Arg Lys Gln Ala His Ala His
1               5                   10                  15

Ser Lys

<210> SEQ ID NO 25
<211> LENGTH: 21
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 25

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 26
<211> LENGTH: 18
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 26

Arg Gly Gly Arg Leu Ser Tyr Ser Arg Arg Arg Phe Ser Thr Ser Thr
1               5                   10                  15

Gly Arg

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 27

Ser Asp Leu Trp Glu Met Met Met Val Ser Leu Ala Cys Gln Tyr
1               5                   10                  15

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 28

Thr Ser Pro Leu Asn Ile His Asn Gly Gln Lys Leu
1               5                   10

<210> SEQ ID NO 29
<211> LENGTH: 19
<212> TYPE: PRT
```

```
<213> ORGANISM: Artificial Sequence
<220> FEATURE:
<223> OTHER INFORMATION: Description of Artificial Sequences; note =
      synthetic construct

<400> SEQUENCE: 29

Pro Ser Arg Ala Ser Ser Arg Ala Ser Ser Arg Pro Arg Pro Asp Asp
1               5                   10                  15

Leu Glu Ile

<210> SEQ ID NO 30
<211> LENGTH: 20
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 30

Gly Ser Asn Lys Ser Thr Ala Ser Ser Lys Ser Pro Asp Pro Lys Asn
1               5                   10                  15

Ser Val Trp Ile
            20

<210> SEQ ID NO 31
<211> LENGTH: 20
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 31

Gly Ser Asn Lys Ser Ser Ala Ser Ser Lys Ser Gly Asp Gly Lys Asn
1               5                   10                  15

Ser Val Trp Ile
            20

<210> SEQ ID NO 32
<211> LENGTH: 21
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 32

Gly Arg Ala Ser Lys Ala Ser Arg Ala Ser Ser Gly Arg Ala Arg Pro
1               5                   10                  15

Glu Asp Leu Ala Ile
            20

<210> SEQ ID NO 33
<211> LENGTH: 13
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 33

Gly Ser Ala Ser Ser Arg Asp Gly Lys Thr Val Trp Ile
1               5                   10

<210> SEQ ID NO 34
```

```
<211> LENGTH: 19
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 34

Pro Arg Val Ser Val Pro Asn Phe Gly Arg Thr Gln Ser Ser Asp Ser
1               5                   10                  15

Ala Tyr Val

<210> SEQ ID NO 35
<211> LENGTH: 19
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 35

Pro Arg Met Ser Met Pro Asn Phe Gly Arg Thr Gln Ser Ser Asp Ser
1               5                   10                  15

Ala Tyr Val

<210> SEQ ID NO 36
<211> LENGTH: 21
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 36

Pro Arg Ala Gly Ser Glu Lys Gly Ser Ala Ser Ser Arg Asp Gly Lys
1               5                   10                  15

Thr Thr Val Trp Ile
            20

<210> SEQ ID NO 37
<211> LENGTH: 23
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 37

Gly Tyr His Ser Asp Lys Arg Arg Leu Ser Lys Ala Ser Ser Lys Ala
1               5                   10                  15

Arg Ser Asp Asp Leu Ser Val
            20

<210> SEQ ID NO 38
<211> LENGTH: 19
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 38

Pro Leu Ser Arg Leu Ser Lys Ala Ser Ser Arg Ala Arg Ser Asp Asp
1               5                   10                  15

Leu Thr Val
```

<210> SEQ ID NO 39
<211> LENGTH: 22
<212> TYPE: PRT
<213> ORGANISM: Artificial Sequence
<220> FEATURE:
<223> OTHER INFORMATION: Description of Artificial Sequences; note = synthetic construct

<400> SEQUENCE: 39

```
Pro Asn His Val Val Ser Leu Thr Asn Asn Leu Ile Gly Arg Arg Val
1               5                   10                  15

Pro Thr Asp Leu Gln Ile
            20
```

<210> SEQ ID NO 40
<211> LENGTH: 29
<212> TYPE: PRT
<213> ORGANISM: Artificial Sequence
<220> FEATURE:
<223> OTHER INFORMATION: Description of Artificial Sequences; note = synthetic construct

<400> SEQUENCE: 40

```
Pro Ser Cys Val Ser Ser Ser Ala Val Leu Thr Thr Ile Cys Ser Ser
1               5                   10                  15

Asp Gln Val Val Pro Val Gly Leu Ser Ser Phe Tyr Met
            20                  25
```

<210> SEQ ID NO 41
<211> LENGTH: 21
<212> TYPE: PRT
<213> ORGANISM: Artificial Sequence
<220> FEATURE:
<223> OTHER INFORMATION: Description of Artificial Sequences; note = synthetic construct

<400> SEQUENCE: 41

```
Gly Arg Ser Ser Lys Ala Ser Lys Ser Ser Gly Gly Arg Ala Arg Ala
1               5                   10                  15

Ala Asp Leu Ala Ile
            20
```

<210> SEQ ID NO 42
<211> LENGTH: 17
<212> TYPE: PRT
<213> ORGANISM: Artificial Sequence
<220> FEATURE:
<223> OTHER INFORMATION: Description of Artificial Sequences; note = synthetic construct

<400> SEQUENCE: 42

```
Leu Cys Tyr Leu Leu Ile Arg Tyr Cys Ser Gly Lys Ser Lys Lys Pro
1               5                   10                  15

Val
```

<210> SEQ ID NO 43
<211> LENGTH: 18
<212> TYPE: PRT
<213> ORGANISM: Artificial Sequence
<220> FEATURE:
<223> OTHER INFORMATION: Description of Artificial Sequences; note = synthetic construct

<400> SEQUENCE: 43

-continued

```
Gly Gln Lys Pro Pro Ser Arg Pro Ser Ser Ala Ser Lys Lys Gln
1               5                   10                  15

Tyr Val

<210> SEQ ID NO 44
<211> LENGTH: 19
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 44

Ser Ser Arg Ala Ser Ser Arg Ala Ser Ser Arg Pro Arg Pro Asp Asp
1               5                   10                  15

Leu Glu Val

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 45

Arg Pro Lys Pro Asp Asp Leu Glu Ile
1               5

<210> SEQ ID NO 46
<211> LENGTH: 19
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 46

Ser Ser Arg Ala Ser Ser Arg Ala Ser Ser Arg Pro Lys Pro Asp Asp
1               5                   10                  15

Leu Glu Ile

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 47

Arg Pro Lys Pro Asp Asp Leu Asp Ile
1               5

<210> SEQ ID NO 48
<211> LENGTH: 19
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 48

Ser Ser Arg Ala Ser Ser Arg Ala Ser Ser Arg Pro Arg Pro Asp Asp
1               5                   10                  15
```

Leu Asp Ile

<210> SEQ ID NO 49
<211> LENGTH: 19
<212> TYPE: PRT
<213> ORGANISM: Artificial Sequence
<220> FEATURE:
<223> OTHER INFORMATION: Description of Artificial Sequences; note = synthetic construct

<400> SEQUENCE: 49

Ser Ser Arg Ala Ser Thr Arg Ala Ser Ser Arg Pro Arg Pro Asp Asp
1               5                   10                  15

Leu Glu Ile

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequences; note = synthetic construct

<400> SEQUENCE: 50

Arg Pro Arg Pro Glu Asp Leu Glu Ile
1               5

<210> SEQ ID NO 51
<211> LENGTH: 19
<212> TYPE: PRT
<213> ORGANISM: Artificial Sequence
<220> FEATURE:
<223> OTHER INFORMATION: Description of Artificial Sequences; note = synthetic construct

<400> SEQUENCE: 51

Ser Ser Arg Ala Ser Ser Arg Ala Ser Ser Arg Pro Arg Pro Glu Asp
1               5                   10                  15

Leu Glu Ile

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequences; note = synthetic construct

<400> SEQUENCE: 52

Gly Asp Gly Lys Asn Ser Val Trp Val
1               5

<210> SEQ ID NO 53
<211> LENGTH: 23
<212> TYPE: PRT
<213> ORGANISM: Artificial Sequence
<220> FEATURE:
<223> OTHER INFORMATION: Description of Artificial Sequences; note = synthetic construct

<400> SEQUENCE: 53

Ser Lys Ala Gly Ser Asn Lys Ser Thr Ala Ser Ser Lys Ser Gly Asp
1               5                   10                  15

Gly Lys Asn Ser Val Trp Val
            20

```
<210> SEQ ID NO 54
<211> LENGTH: 18
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 54

Gly Gln Lys Pro Pro Ser Arg Pro Ser Ser Ser Ala Ser Lys Lys Leu
1               5                   10                  15

Tyr Val

<210> SEQ ID NO 55
<211> LENGTH: 24
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 55

Arg Gln Pro Lys Ile Trp Phe Pro Asn Arg Arg Lys Pro Trp Lys Ile
1               5                   10                  15

Glu Leu Asp Asp Pro Arg Pro Arg
            20

<210> SEQ ID NO 56
<211> LENGTH: 20
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 56

Gly Arg Lys Lys Arg Arg Gln Arg Pro Pro Gln Pro Arg Pro Arg Asp
1               5                   10                  15

Asp Leu Glu Ile
            20

<210> SEQ ID NO 57
<211> LENGTH: 25
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 57

Arg Gln Ile Lys Ile Trp Phe Gln Asn Arg Arg Met Lys Trp Lys Lys
1               5                   10                  15

Arg Pro Arg Pro Asp Asp Leu Glu Ile
            20                  25

<210> SEQ ID NO 58
<211> LENGTH: 25
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 58

Arg Gln Ile Ala Ile Trp Phe Gln Asn Arg Arg Met Lys Trp Ala Ala
```

```
1               5                   10                  15

Arg Pro Arg Pro Asp Asp Leu Glu Ile
            20                  25

<210> SEQ ID NO 59
<211> LENGTH: 18
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 59

Arg Lys Lys Arg Arg Gln Arg Arg Arg Pro Arg Pro Asp Asp Leu
1               5                   10                  15

Glu Ile

<210> SEQ ID NO 60
<211> LENGTH: 30
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 60

Thr Arg Ser Ser Arg Ala Gly Leu Gln Phe Pro Val Gly Arg Val His
1               5                   10                  15

Arg Leu Leu Arg Lys Arg Pro Arg Pro Asp Asp Leu Glu Ile
            20                  25                  30

<210> SEQ ID NO 61
<211> LENGTH: 35
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 61

Gly Trp Thr Leu Asn Ser Ala Gly Tyr Leu Leu Gly Lys Ile Asn Lys
1               5                   10                  15

Ala Leu Ala Ala Leu Ala Lys Lys Ile Leu Arg Pro Arg Pro Asp Asp
            20                  25                  30

Leu Glu Ile
        35

<210> SEQ ID NO 62
<211> LENGTH: 27
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 62

Lys Leu Ala Leu Lys Leu Ala Leu Lys Ala Leu Lys Ala Ala Leu Lys
1               5                   10                  15

Leu Ala Arg Pro Arg Pro Asp Asp Leu Glu Ile
            20                  25

<210> SEQ ID NO 63
<211> LENGTH: 25
<212> TYPE: PRT
```

<213> ORGANISM: Artificial Sequence
<220> FEATURE:
<223> OTHER INFORMATION: Description of Artificial Sequences; note = synthetic construct

<400> SEQUENCE: 63

Ala Ala Val Ala Leu Leu Pro Ala Val Leu Ala Leu Leu Ala Pro
1               5                   10                  15

Arg Pro Arg Pro Asp Asp Leu Glu Ile
            20                  25

<210> SEQ ID NO 64
<211> LENGTH: 19
<212> TYPE: PRT
<213> ORGANISM: Artificial Sequence
<220> FEATURE:
<223> OTHER INFORMATION: Description of Artificial Sequences; note = synthetic construct

<400> SEQUENCE: 64

Val Pro Met Leu Lys Pro Met Leu Lys Glu Arg Pro Arg Pro Asp Asp
1               5                   10                  15

Leu Glu Ile

<210> SEQ ID NO 65
<211> LENGTH: 37
<212> TYPE: PRT
<213> ORGANISM: Artificial Sequence
<220> FEATURE:
<223> OTHER INFORMATION: Description of Artificial Sequences; note = synthetic construct

<400> SEQUENCE: 65

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro Arg Pro Arg Pro
            20                  25                  30

Asp Asp Leu Glu Ile
        35

<210> SEQ ID NO 66
<211> LENGTH: 27
<212> TYPE: PRT
<213> ORGANISM: Artificial Sequence
<220> FEATURE:
<223> OTHER INFORMATION: Description of Artificial Sequences; note = synthetic construct

<400> SEQUENCE: 66

Leu Leu Ile Ile Leu Arg Arg Arg Ile Arg Lys Gln Ala His Ala His
1               5                   10                  15

Ser Lys Arg Pro Arg Pro Asp Asp Leu Glu Ile
            20                  25

<210> SEQ ID NO 67
<211> LENGTH: 30
<212> TYPE: PRT
<213> ORGANISM: Artificial Sequence
<220> FEATURE:
<223> OTHER INFORMATION: Description of Artificial Sequences; note = synthetic construct

<400> SEQUENCE: 67

Lys Glu Thr Trp Trp Glu Thr Trp Trp Thr Glu Trp Ser Gln Pro Lys
1               5                   10                  15

```
Lys Lys Arg Lys Val Arg Pro Arg Pro Asp Asp Leu Glu Ile
            20                  25                  30

<210> SEQ ID NO 68
<211> LENGTH: 27
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 68

Arg Gly Gly Arg Leu Ser Tyr Ser Arg Arg Phe Ser Thr Ser Thr
1               5                   10                  15

Gly Arg Arg Pro Arg Pro Asp Asp Leu Glu Ile
            20                  25

<210> SEQ ID NO 69
<211> LENGTH: 24
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 69

Ser Asp Leu Trp Glu Met Met Met Val Ser Leu Ala Cys Gln Tyr Arg
1               5                   10                  15

Pro Arg Pro Asp Asp Leu Glu Ile
            20

<210> SEQ ID NO 70
<211> LENGTH: 21
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 70

Thr Ser Pro Leu Asn Ile His Asn Gly Gln Lys Leu Arg Pro Arg Pro
1               5                   10                  15

Asp Asp Leu Glu Ile
            20

<210> SEQ ID NO 71
<211> LENGTH: 120
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 71

Lys Gly Lys Ser Asp Pro Tyr His Ala Thr Ser Gly Ala Leu Ser Pro
1               5                   10                  15

Ala Lys Asp Cys Gly Ser Gln Lys Tyr Ala Tyr Phe Asn Gly Cys Ser
            20                  25                  30

Ser Pro Thr Ala Pro Leu Ser Pro Met Ser Pro Pro Gly Tyr Lys Leu
        35                  40                  45

Val Thr Gly Asp Arg Asn Asn Ser Ser Cys Arg Asn Tyr Asn Lys Gln
    50                  55                  60

Ala Ser Glu Gln Asn Trp Ala Asn Tyr Ser Ala Glu Gln Asn Arg Met
```

```
                65                  70                  75                  80
Gly Gln Ala Gly Ser Thr Ile Ser Asn Ser His Ala Gln Pro Phe Asp
                    85                  90                  95

Phe Pro Asp Asp Asn Gln Asn Ser Lys Lys Leu Ala Ala Gly His Glu
            100                 105                 110

Leu Gln Pro Leu Ala Ile Val Asp
        115                 120

<210> SEQ ID NO 72
<211> LENGTH: 120
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 72

Lys Thr Asp Pro Tyr Ser His Ser Gly Thr Met Ser Pro Ser Lys Asp
1               5                   10                  15

Cys Gly Ser Pro Lys Tyr Ala Tyr Tyr Asn Gly Cys Ser Ser Pro Thr
            20                  25                  30

Ala Pro Leu Ser Pro Met Ser Pro Gly Tyr Lys Leu Val Thr Gly
        35                  40                  45

Asp Arg Asn Asn Ser Ser Cys Arg Asn Tyr Asn Lys Gln Ala Ser Glu
    50                  55                  60

Gln Asn Trp Ala Asn Tyr Ser Ala Glu Gln Asn Arg Met Gly Gln Ala
65                  70                  75                  80

Gly Ser Thr Ile Ser Asn Ser His Ala Gln Pro Phe Asp Phe Ala Asp
                85                  90                  95

Glu His Gln Asn Thr Lys Lys Leu Ala Ser Gly His Glu Leu Gln Pro
            100                 105                 110

Leu Thr Ile Val Asp Gln Arg Pro
        115                 120

<210> SEQ ID NO 73
<211> LENGTH: 120
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 73

Leu Gly Phe Gly Thr Ile Arg Asp Ser Leu Asn Ser Lys Arg Arg Glu
1               5                   10                  15

Leu Glu Asp Pro Gly Ala Tyr Asn Tyr Pro Phe Thr Trp Asn Thr Pro
            20                  25                  30

Ser Ala Pro Pro Gly Tyr Asn Ile Ala Val Lys Pro Asp Gln Ile Gln
        35                  40                  45

Tyr Thr Glu Leu Ser Asn Ala Lys Ile Ala Tyr Lys Gln Asn Lys Ala
    50                  55                  60

Asn Thr Ala Gln Glu Gln Tyr Gly Ser His Glu Glu Asn Leu Pro
65                  70                  75                  80

Ala Asp Leu Glu Ala Leu Gln Arg Glu Ile Arg Met Ala Gln Glu Arg
                85                  90                  95

Leu Asp Leu Ala Val Gln Ala Tyr Ser His Gln Asn Asn Pro His Gly
            100                 105                 110

Pro Arg Glu Lys Lys Ala Lys Val
```

<210> SEQ ID NO 74
<211> LENGTH: 120
<212> TYPE: PRT
<213> ORGANISM: Artificial Sequence
<220> FEATURE:
<223> OTHER INFORMATION: Description of Artificial Sequences; note = synthetic construct

<400> SEQUENCE: 74

```
Gly Phe Gly Thr Ile Arg Asp Thr Leu Asn Asn Lys Arg Lys Glu Leu
1               5                   10                  15

Glu Asp Ser Gly Thr Tyr Asn Tyr Pro Phe Thr Trp Asn Thr Pro Ser
            20                  25                  30

Ala Pro Pro Gly Tyr Asn Ile Ala Val Lys Pro Asp Gln Met Gln Tyr
        35                  40                  45

Thr Glu Leu Ser Asn Ala Lys Met Ala Tyr Lys Gln Asn Lys Ala Asn
    50                  55                  60

Ile Ala Gln Glu Gln Gln Tyr Gly Ser Asn Glu Glu Asn Ile Pro Ala
65                  70                  75                  80

Asp Leu Glu Asn Leu Gln Arg Glu Ile Lys Val Ala Gln Glu Arg Leu
                85                  90                  95

Asp Met Ala Ile Gln Ala Tyr Asn Asn Gln Asn Asn Pro Gly Ser Ser
            100                 105                 110

Ser Arg Glu Lys Lys Ser Lys Ala
        115                 120
```

<210> SEQ ID NO 75
<211> LENGTH: 120
<212> TYPE: PRT
<213> ORGANISM: Artificial Sequence
<220> FEATURE:
<223> OTHER INFORMATION: Description of Artificial Sequences; note = synthetic construct

<400> SEQUENCE: 75

```
Pro Tyr Leu Val Asp Cys Phe Val Ser Arg Pro Thr Glu Lys Thr Ile
1               5                   10                  15

Phe Ile Ile Phe Met Leu Val Val Gly Leu Ile Ser Leu Val Leu Asn
            20                  25                  30

Leu Leu Glu Leu Val His Leu Leu Cys Arg Cys Leu Ser Arg Gly Met
        35                  40                  45

Arg Ala Arg Gln Gly Gln Asp Ala Pro Pro Thr Gln Gly Thr Ser Ser
    50                  55                  60

Asp Pro Tyr Thr Asp Gln Val Phe Phe Tyr Leu Pro Val Gly Gln Gly
65                  70                  75                  80

Pro Ser Ser Pro Pro Cys Pro Thr Tyr Asn Gly Leu Ser Ser Ser Glu
                85                  90                  95

Gln Asn Trp Ala Asn Leu Thr Thr Glu Glu Arg Leu Ala Ser Ser Arg
            100                 105                 110

Pro Pro Leu Phe Leu Asp Pro Pro
        115                 120
```

<210> SEQ ID NO 76
<211> LENGTH: 120
<212> TYPE: PRT
<213> ORGANISM: Artificial Sequence
<220> FEATURE:
<223> OTHER INFORMATION: Description of Artificial Sequences; note = synthetic construct

<400> SEQUENCE: 76

Cys Gly Ser Lys Glu His Gly Asn Arg Lys Met Arg Gly Arg Leu Leu
1               5                   10                  15

Leu Thr Tyr Met Ala Ser Ile Phe Phe Lys Ser Val Phe Glu Val Ala
            20                  25                  30

Phe Leu Leu Ile Gln Trp Tyr Leu Tyr Gly Phe Thr Leu Ser Ala Val
        35                  40                  45

Tyr Ile Cys Glu Gln Ser Pro Cys Pro His Arg Val Asp Cys Phe Leu
    50                  55                  60

Ser Arg Pro Thr Glu Lys Thr Ile Phe Ile Leu Phe Met Leu Val Val
65                  70                  75                  80

Ser Met Val Ser Phe Val Leu Asn Val Ile Glu Leu Phe Tyr Val Leu
                85                  90                  95

Phe Lys Ala Ile Lys Asn His Leu Gly Asn Glu Lys Glu Val Tyr
            100                 105                 110

Cys Asn Pro Val Glu Leu Gln Lys
        115                 120

<210> SEQ ID NO 77
<211> LENGTH: 239
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 77

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe

-continued

```
                210             215             220
Val Thr Ala Ala Gly Ile Thr Leu Gly Met Asp Glu Leu Tyr Lys
225                 230                 235
```

<210> SEQ ID NO 78
<211> LENGTH: 60
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 78
ccctcctccc gggcctcctc ccgggcctcc tcccggcccc ggcccgacga cctggagatc    60

<210> SEQ ID NO 79
<211> LENGTH: 27
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 79
cggccccggc ccgacgacct ggagatc                                         27

<210> SEQ ID NO 80
<211> LENGTH: 27
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 80
cggccccggc ccgacgacct ggaggtg                                         27

<210> SEQ ID NO 81
<211> LENGTH: 27
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 81
cggccccggc ccgacgacgt gcccgtg                                         27

<210> SEQ ID NO 82
<211> LENGTH: 27
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 82
aaggcccggt ccgacgacct gtccgtg                                         27

<210> SEQ ID NO 83
<211> LENGTH: 48
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 83
cggcagccca agatctggtt ccccaaccgg cggaagccct ggaagaag    48

<210> SEQ ID NO 84
<211> LENGTH: 108
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 84
cggcagccca agatctggtt ccccaaccgg cggaagccct ggaagaagcc ctcctcccgg    60
gcctcctccc gggcctcctc ccggccccgg cccgacgacc tggagatc    108

<210> SEQ ID NO 85
<211> LENGTH: 75
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 85
cggcagccca agatctggtt ccccaaccgg cggaagccct ggaagaagcg ccccggccc    60 gacgacctgg agatc    75

<210> SEQ ID NO 86
<211> LENGTH: 75
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 86
cggcagccca agatctggtt ccccaaccgg cggaagccct ggaagaagcg ccccggccc    60 gacgacctgg aggtg    75

<210> SEQ ID NO 87
<211> LENGTH: 75
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 87
cggcagccca agatctggtt ccccaaccgg cggaagccct ggaagaagcg ccccggccc    60 gacgacgtgc ccgtg    75

<210> SEQ ID NO 88
<211> LENGTH: 75
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 88
cggcagccca agatctggtt ccccaaccgg cggaagccct ggaagaagaa ggcccggtcc    60
gacgacctgt ccgtg    75

```
<210> SEQ ID NO 89
<211> LENGTH: 20
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 89

Pro Cys Ser Arg Ala Ser Ser Arg Met Ser Ser Arg Ala Arg Pro Asp
1               5                   10                  15

Asp Leu Asp Val
            20

<210> SEQ ID NO 90
<211> LENGTH: 19
<212> TYPE: PRT
<213> ORGANISM: Artificial Sequence
<220> FEATURE:
<223> OTHER INFORMATION: Description of Artificial Sequences; note =
      synthetic construct

<400> SEQUENCE: 90

Pro Arg Val Ser Val Pro Asn Phe Gly Arg Thr Gln Ser Ser Asp Ser
1               5                   10                  15

Ala Tyr Val
```